(12) United States Patent
Kowalewsky et al.

(10) Patent No.: US 10,899,845 B2
(45) Date of Patent: Jan. 26, 2021

(54) ANTI-VARIANT FC-REGION ANTIBODIES AND METHOD OF USE

(71) Applicant: Hoffmann-La Roche Inc., Little Falls, NJ (US)

(72) Inventors: Frank Kowalewsky, Munich (DE); Mirko Ritter, Bernried (DE); Kay-Gunnar Stubenrauch, Penzberg (DE); Uwe Wessels, Penzberg (DE)

(73) Assignee: Hoffmann-La Roche Inc., Little Falls, NJ (US)

( * ) Notice: Subject to any disclaimer, the term of this patent is extended or adjusted under 35 U.S.C. 154(b) by 364 days.

(21) Appl. No.: 15/962,429

(22) Filed: Apr. 25, 2018

(65) Prior Publication Data
US 2018/0346602 A1    Dec. 6, 2018

Related U.S. Application Data

(63) Continuation of application No. PCT/EP2016/075884, filed on Oct. 27, 2016.

(30) Foreign Application Priority Data

Oct. 29, 2015 (EP) .................................... 15192195

(51) Int. Cl.
| | | |
|---|---|---|
| G01N 33/53 | (2006.01) | |
| C07K 16/46 | (2006.01) | |
| C07K 16/28 | (2006.01) | |
| C07K 16/22 | (2006.01) | |
| C07K 16/42 | (2006.01) | |
| C07K 16/00 | (2006.01) | |

(52) U.S. Cl.
CPC ............ *C07K 16/462* (2013.01); *C07K 16/00* (2013.01); *C07K 16/22* (2013.01); *C07K 16/283* (2013.01); *C07K 16/2854* (2013.01); *C07K 16/2863* (2013.01); *C07K 16/42* (2013.01); *G01N 33/5306* (2013.01); *C07K 2317/24* (2013.01); *C07K 2317/52* (2013.01); *C07K 2317/524* (2013.01); *C07K 2317/526* (2013.01); *C07K 2317/565* (2013.01)

(58) Field of Classification Search
CPC .... C07K 16/462; C07K 16/283; C07K 16/22; C07K 16/2854; C07K 16/42; C07K 16/00; C07K 16/2863; C07K 2317/526; C07K 2317/524; C07K 2317/24; C07K 2317/52; C07K 2317/565; G01N 33/5306
See application file for complete search history.

(56) References Cited

FOREIGN PATENT DOCUMENTS

| WO | 89/12231 A1 | 12/1989 |
|---|---|---|
| WO | 2014/009474 A1 | 1/2014 |
| WO | 2014/177459 A2 | 11/2014 |
| WO | 2015/107025 A1 | 7/2015 |

OTHER PUBLICATIONS

Bautista et al., "Impact of matrix-associated soluble factors on the specificity of the immunogenicity assessment" Bioanalysis 2:721-731 ( 2010).
International Search Report and Written Opinion for International Patent Application No. PCT/EP2016/075884 completed on Apr. 4, 2017.
Geng et al., "Validation of immunoassays used to assess immunogenicity to therapeutic monoclonal antibodies" J Pharmaceutical and Biomedical Analysis 39:364-375 ( 2005).
Mikulskis et al., "Solution ELISA as a platform of choice for development of robust, drug tolerant immunogenicity assays in support of drug development" J Immunol Meth 365:38-49 ( 2011).
Mire-Sluis et al., "Recommendations for the design and optimization of immunoassays used in the detection of host antibodies against biotechnology products" J Immunol Methods 289:1-16 ( 2004).
Thway et al., "Impact of anti-drug antibiotics in preclinical pharmacokinetic assessment" The AAPS J 15(3):856-863 (Jul. 2013).
Weeraratne et al., "Development of a biosensor-based immunogenicity assay capable of blocking soluble drug target interference" J Immunol Methods 396:44-55 ( 2013).
Zhong et al., "Identification and inhibition of drug target interference in" J Immunol Meth 355:21-28 ( 2010).

*Primary Examiner* — Carmencita M Belei

(57) ABSTRACT

The invention provides anti-variant Fc-region antibodies which specifically bind to an antibody that has the mutation P329G or the mutations P329G/L234A/L235A or the mutations I253A/H310A/H435A in the Fc-region, and methods of using the same.

6 Claims, 8 Drawing Sheets

Specification includes a Sequence Listing.

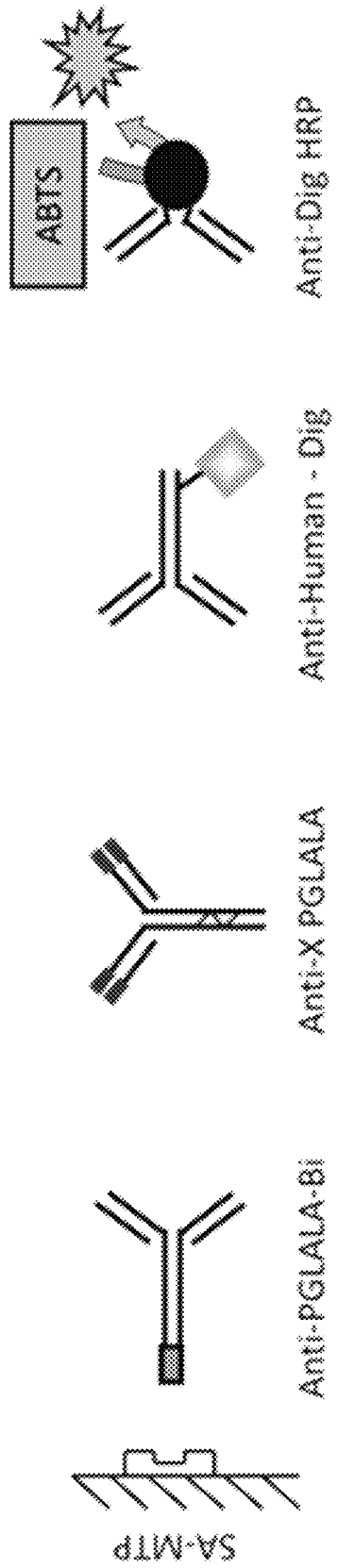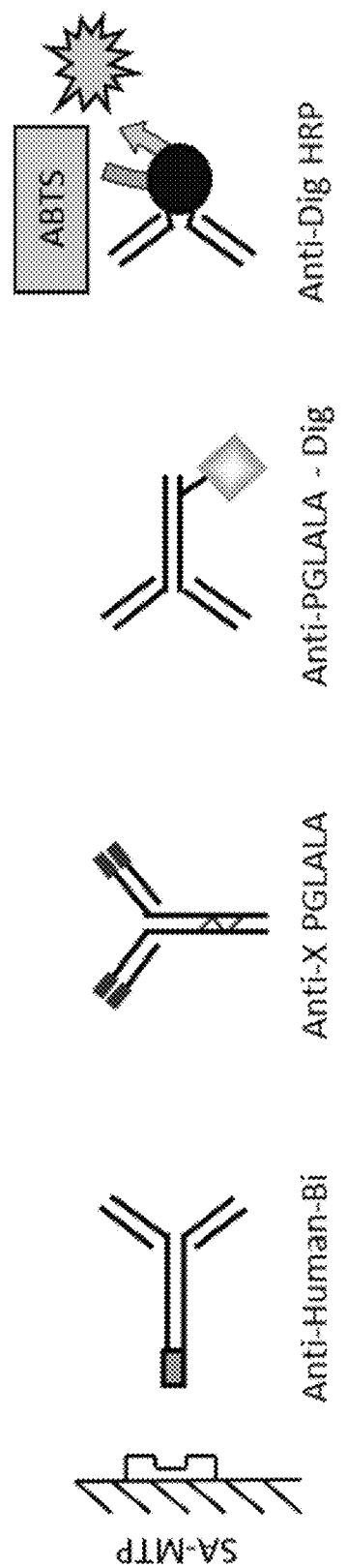

Figure 5
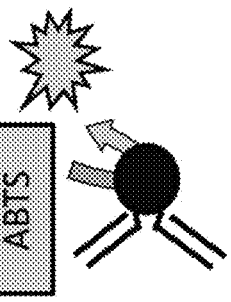
Anti-Dig HRP
H-FCγRI-Dig (CD64-Dig)
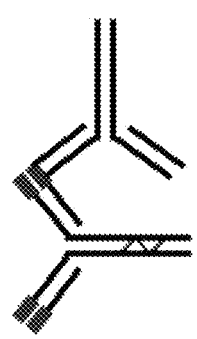
Anti-X PGLALA with ADA (Human IgG)
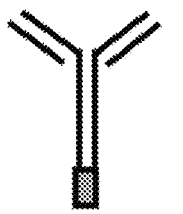
Anti-PGLALA-Bi
SA-MTP

```
                         SEQUENCE LISTING

<160> NUMBER OF SEQ ID NOS: 35

<210> SEQ ID NO 1
<211> LENGTH: 137
<212> TYPE: PRT
<213> ORGANISM: Mus musculus

<400> SEQUENCE: 1

Met Asp Phe Gly Leu Ile Phe Phe Ile Val Ala Leu Leu Lys Gly Val
1               5                   10                  15

Leu Cys Glu Val Arg Leu Leu Glu Ser Gly Gly Gly Leu Val Gln Pro
                20                  25                  30

Gly Gly Ser Leu Lys Leu Ser Cys Ala Ala Ser Gly Phe Asp Phe Ser
            35                  40                  45

Arg Tyr Trp Met Ser Trp Val Arg Gln Ala Pro Gly Lys Gly Leu Glu
    50                  55                  60

Trp Ile Gly Glu Ile Asn Pro Asp Ser Arg Pro Ile Asn Ser Ser Pro
65                  70                  75                  80

Ser Leu Lys Asp Lys Phe Ile Ile Ser Arg Asp Asn Val Lys Asn Thr
                85                  90                  95

Leu Tyr Leu Gln Met Asn Glu Leu Gly Ser Glu Asp Thr Ala Leu Tyr
            100                 105                 110

Tyr Cys Ala Arg Pro Leu Asp Tyr Gly Ala Trp Phe Ala Asn Trp Gly
        115                 120                 125

Gln Gly Thr Leu Val Ser Val Ser Ala
    130                 135

<210> SEQ ID NO 2
<211> LENGTH: 128
<212> TYPE: PRT
<213> ORGANISM: Mus musculus

<400> SEQUENCE: 2

Met Ala Trp Thr Ser Leu Phe Leu Ser Leu Leu Ala Leu Ser Ser Gly
1               5                   10                  15

Ala Ile Ser Gln Ala Val Val Thr Gln Glu Ser Ala Leu Thr Thr Ser
                20                  25                  30

Pro Gly Glu Thr Val Thr Leu Thr Cys Arg Ser Ser Thr Gly Ala Val
            35                  40                  45

Thr Thr Ser Asn Tyr Ala Asn Trp Val Gln Glu Lys Pro Asp His Val
    50                  55                  60

Phe Ser Gly Leu Ile Gly Gly Thr Asn Lys Arg Ala Pro Gly Phe Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Val Leu Trp
            100                 105                 110

Tyr Ser Asn His Trp Val Phe Gly Gly Gly Thr Lys Leu Thr Val Leu
        115                 120                 125
```

<210> SEQ ID NO 3
<211> LENGTH: 137
<212> TYPE: PRT
<213> ORGANISM: Mus musculus

<400> SEQUENCE: 3

```
Met Asp Phe Gly Leu Ile Phe Phe Ile Val Ala Leu Leu Lys Gly Val
1               5                   10                  15

Gln Cys Glu Val Lys Leu Leu Glu Ser Gly Gly Gly Leu Val Gln Pro
            20                  25                  30

Gly Gly Ser Leu Lys Leu Ser Cys Ala Ala Ser Gly Ile Asp Phe Arg
        35                  40                  45

Arg Tyr Trp Met Asn Trp Val Arg Gln Ala Pro Gly Lys Gly Leu Glu
    50                  55                  60

Trp Ile Gly Glu Ile Asp Pro Asp Ser Ser Thr Ile Asn Tyr Thr Pro
65                  70                  75                  80

Ser Leu Lys Asp Lys Phe Ile Ile Ser Arg Asp Asn Ala Lys Asn Thr
                85                  90                  95

Met Tyr Leu Gln Met Arg Lys Val Arg Ser Glu Asp Thr Ala Leu Tyr
            100                 105                 110

Tyr Cys Ala Arg Pro Tyr Asp Tyr Gly Ala Trp Phe Ala Tyr Trp Gly
        115                 120                 125

Gln Gly Thr Leu Val Thr Val Ser Ala
    130                 135
```

<210> SEQ ID NO 4
<211> LENGTH: 128
<212> TYPE: PRT
<213> ORGANISM: Mus musculus

<400> SEQUENCE: 4

```
Met Ala Trp Ile Ser Leu Leu Phe Ser Leu Leu Ala Leu Ser Ser Gly
1               5                   10                  15

Ala Ile Ser Gln Ala Val Val Thr Gln Glu Ser Ala Leu Thr Thr Ser
            20                  25                  30

Pro Gly Glu Thr Val Thr Leu Thr Cys Arg Ser Thr Thr Gly Ala Val
        35                  40                  45

Thr Thr Ser Asn Tyr Ala Asn Trp Val Gln Glu Lys Pro Asp His Leu
    50                  55                  60

Phe Thr Gly Leu Ile Gly Gly Thr Asn Lys Arg Ala Pro Gly Val Pro
65                  70                  75                  80

Ala Arg Phe Ser Gly Ser Leu Ile Gly Asp Lys Ala Ala Leu Thr Ile
                85                  90                  95

Thr Gly Ala Gln Thr Glu Asp Glu Ala Ile Tyr Phe Cys Ala Leu Trp
            100                 105                 110

Tyr Ser Asp His Trp Val Phe Gly Gly Gly Thr Lys Leu Thr Val Leu
        115                 120                 125
```

<210> SEQ ID NO 5
<211> LENGTH: 140
<212> TYPE: PRT
<213> ORGANISM: Mus musculus

<400> SEQUENCE: 5

```
Met Asn Phe Gly Leu Ser Leu Val Phe Leu Ala Leu Ile Leu Lys Gly
1               5                   10                  15
```

```
Val Gln Cys Glu Val Gln Leu Val Glu Ser Gly Gly Asp Leu Val Lys
             20                  25                  30

Pro Gly Gly Ser Leu Lys Leu Ser Cys Ala Ala Ser Gly Phe Thr Phe
         35                  40                  45

Ser Ser Tyr Gly Met Ser Trp Val Arg Gln Thr Pro Asp Lys Arg Leu
 50                  55                  60

Glu Trp Val Ala Thr Ile Ser Ser Gly Gly Ser Tyr Ile Tyr Tyr Pro
 65                  70                  75                  80

Asp Ser Val Lys Gly Arg Phe Thr Ile Ser Arg Asp Asn Ala Lys Asn
             85                  90                  95

Thr Leu Tyr Leu Gln Met Ser Ser Leu Lys Ser Glu Asp Thr Ala Met
            100                 105                 110

Tyr Tyr Cys Ala Arg Leu Gly Met Ile Thr Thr Gly Tyr Ala Met Asp
        115                 120                 125

Tyr Trp Gly Gln Gly Thr Ser Val Thr Val Ser Ser
        130                 135                 140
```

<210> SEQ ID NO 6
<211> LENGTH: 112
<212> TYPE: PRT
<213> ORGANISM: Mus musculus

<400> SEQUENCE: 6

```
Asp Val Leu Met Thr Gln Thr Pro Leu Ser Leu Pro Val Ser Leu Gly
 1               5                  10                  15

Asp Gln Ala Ser Ile Ser Cys Arg Ser Ser Gln Thr Ile Val His Ser
             20                  25                  30

Thr Gly His Thr Tyr Leu Glu Trp Phe Leu Gln Lys Pro Gly Gln Ser
         35                  40                  45

Pro Lys Leu Leu Ile Tyr Lys Val Ser Asn Arg Phe Ser Gly Val Pro
 50                  55                  60

Asp Arg Phe Ser Gly Ser Gly Ser Gly Thr Asp Phe Thr Leu Lys Ile
 65                  70                  75                  80

Ser Arg Val Glu Ala Glu Asp Leu Gly Val Tyr Tyr Cys Phe Gln Gly
             85                  90                  95

Ser His Val Pro Tyr Thr Phe Gly Gly Gly Thr Lys Leu Glu Ile Lys
            100                 105                 110
```

<210> SEQ ID NO 7
<211> LENGTH: 137
<212> TYPE: PRT
<213> ORGANISM: Mus musculus

<400> SEQUENCE: 7

```
Met Asp Phe Gly Leu Ile Phe Phe Ile Val Ala Leu Leu Lys Gly Val
 1               5                  10                  15

Gln Cys Glu Val Lys Leu Leu Glu Ser Gly Gly Gly Leu Val Gln Pro
             20                  25                  30

Gly Gly Ser Leu Lys Leu Ser Cys Ala Ala Ser Gly Phe Asp Phe Ser
         35                  40                  45

Arg Tyr Trp Met Asn Trp Val Arg Gln Ala Pro Gly Lys Gly Leu Glu
 50                  55                  60

Trp Ile Gly Glu Ile Thr Pro Asp Ser Ser Thr Ile Asn Tyr Thr Pro
 65                  70                  75                  80

Ser Leu Lys Asp Lys Phe Ile Ile Ser Arg Asp Asn Ala Lys Asn Thr
             85                  90                  95
```

-continued

Leu Tyr Leu Gln Met Ile Lys Val Arg Ser Glu Asp Thr Ala Leu Tyr
                100                 105                 110

Tyr Cys Val Arg Pro Tyr Asp Tyr Gly Ala Trp Phe Ala Ser Trp Gly
            115                 120                 125

Gln Gly Thr Leu Val Thr Val Ser Ala
    130                 135

<210> SEQ ID NO 8
<211> LENGTH: 109
<212> TYPE: PRT
<213> ORGANISM: Mus musculus

<400> SEQUENCE: 8

Gln Ala Val Val Thr Gln Glu Ser Ala Leu Thr Thr Ser Pro Gly Glu
1               5                   10                  15

Thr Val Thr Leu Thr Cys Arg Ser Ser Thr Gly Ala Val Thr Thr Ser
            20                  25                  30

Asn Tyr Ala Asn Trp Val Gln Glu Lys Pro Asp His Leu Phe Thr Gly
        35                  40                  45

Leu Ile Gly Gly Thr Asn Lys Arg Ala Pro Gly Val Pro Ala Arg Phe
    50                  55                  60

Ser Gly Ser Leu Ile Gly Asp Lys Ala Ala Leu Thr Ile Thr Gly Ala
65                  70                  75                  80

Gln Thr Glu Asp Glu Ala Ile Tyr Phe Cys Ala Leu Trp Tyr Ser Asn
                85                  90                  95

His Trp Val Phe Gly Gly Gly Thr Lys Leu Thr Val Leu
                100                 105

<210> SEQ ID NO 9
<211> LENGTH: 5
<212> TYPE: PRT
<213> ORGANISM: Mus musculus

<400> SEQUENCE: 9

Arg Tyr Trp Met Ser
1               5

<210> SEQ ID NO 10
<211> LENGTH: 5
<212> TYPE: PRT
<213> ORGANISM: Mus musculus

<400> SEQUENCE: 10

Arg Tyr Trp Met Asn
1               5

<210> SEQ ID NO 11
<211> LENGTH: 5
<212> TYPE: PRT
<213> ORGANISM: Artificial sequence
<220> FEATURE:
<223> OTHER INFORMATION: HVR-H1 consensus sequence
<220> FEATURE:
<221> NAME/KEY: MISC_FEATURE
<222> LOCATION: (5)..(5)
<223> OTHER INFORMATION: X denotes a neutral hydrophilic amino acid
      residue

<400> SEQUENCE: 11

Arg Tyr Trp Met Xaa
1               5

```
<210> SEQ ID NO 12
<211> LENGTH: 17
<212> TYPE: PRT
<213> ORGANISM: Mus musculus

<400> SEQUENCE: 12

Glu Ile Asn Pro Asp Ser Arg Pro Ile Asn Ser Ser Pro Ser Leu Lys
1               5                   10                  15

Asp

<210> SEQ ID NO 13
<211> LENGTH: 17
<212> TYPE: PRT
<213> ORGANISM: Mus musculus

<400> SEQUENCE: 13

Glu Ile Asp Pro Asp Ser Ser Thr Ile Asn Tyr Thr Pro Ser Leu Lys
1               5                   10                  15

Asp

<210> SEQ ID NO 14
<211> LENGTH: 17
<212> TYPE: PRT
<213> ORGANISM: Mus musculus

<400> SEQUENCE: 14

Glu Ile Thr Pro Asp Ser Ser Thr Ile Asn Tyr Thr Pro Ser Leu Lys
1               5                   10                  15

Asp

<210> SEQ ID NO 15
<211> LENGTH: 17
<212> TYPE: PRT
<213> ORGANISM: Artificial sequence
<220> FEATURE:
<223> OTHER INFORMATION: HVR-H2 consensus sequence
<220> FEATURE:
<221> NAME/KEY: MISC_FEATURE
<222> LOCATION: (3)..(3)
<223> OTHER INFORMATION: X = neutral hydrophilic or acidic amino acid
      residue
<220> FEATURE:
<221> NAME/KEY: MISC_FEATURE
<222> LOCATION: (7)..(7)
<223> OTHER INFORMATION: X = neutral hydrophilic or basic amino aicd
      residue
<220> FEATURE:
<221> NAME/KEY: MISC_FEATURE
<222> LOCATION: (8)..(8)
<223> OTHER INFORMATION: X = neutral hydrophilic or chain influencing
      amino aicd residue
<220> FEATURE:
<221> NAME/KEY: MISC_FEATURE
<222> LOCATION: (11)..(11)
<223> OTHER INFORMATION: X = neutral hydrophilic or aromatic amino aicd
      residue
<220> FEATURE:
<221> NAME/KEY: MISC_FEATURE
<222> LOCATION: (12)..(12)
<223> OTHER INFORMATION: X = neutral hydrophilic amino aicd residue

<400> SEQUENCE: 15

Glu Ile Xaa Pro Asp Ser Xaa Xaa Ile Asn Xaa Xaa Pro Ser Leu Lys
1               5                   10                  15

Asp

<210> SEQ ID NO 16
```

<210> SEQ ID NO 16
<211> LENGTH: 10
<212> TYPE: PRT
<213> ORGANISM: Mus musculus

<400> SEQUENCE: 16

Pro Leu Asp Tyr Gly Ala Trp Phe Ala Asn
1               5                   10

<210> SEQ ID NO 17
<211> LENGTH: 10
<212> TYPE: PRT
<213> ORGANISM: Mus musculus

<400> SEQUENCE: 17

Pro Tyr Asp Tyr Gly Ala Trp Phe Ala Tyr
1               5                   10

<210> SEQ ID NO 18
<211> LENGTH: 10
<212> TYPE: PRT
<213> ORGANISM: Mus musculus

<400> SEQUENCE: 18

Pro Tyr Asp Tyr Gly Ala Trp Phe Ala Ser
1               5                   10

<210> SEQ ID NO 19
<211> LENGTH: 10
<212> TYPE: PRT
<213> ORGANISM: Artificial sequence
<220> FEATURE:
<223> OTHER INFORMATION: HVR-H3 consensus sequence
<220> FEATURE:
<221> NAME/KEY: MISC_FEATURE
<222> LOCATION: (2)..(2)
<223> OTHER INFORMATION: X=hydrophobic or aromatic amino acid residue
<220> FEATURE:
<221> NAME/KEY: MISC_FEATURE
<222> LOCATION: (10)..(10)
<223> OTHER INFORMATION: X=neutral hydrophilic or aromatic amino acid
      residue

<400> SEQUENCE: 19

Pro Xaa Asp Tyr Gly Ala Trp Phe Ala Xaa
1               5                   10

<210> SEQ ID NO 20
<211> LENGTH: 5
<212> TYPE: PRT
<213> ORGANISM: Mus musculus

<400> SEQUENCE: 20

Ser Tyr Gly Met Ser
1               5

<210> SEQ ID NO 21
<211> LENGTH: 17
<212> TYPE: PRT
<213> ORGANISM: Mus musculus

<400> SEQUENCE: 21

Thr Ile Ser Ser Gly Gly Ser Tyr Ile Tyr Tyr Pro Asp Ser Val Lys
1               5                   10                  15

Gly

<210> SEQ ID NO 22

```
<211> LENGTH: 12
<212> TYPE: PRT
<213> ORGANISM: Mus musculus

<400> SEQUENCE: 22

Leu Gly Met Ile Thr Thr Gly Tyr Ala Met Asp Tyr
1               5                   10

<210> SEQ ID NO 23
<211> LENGTH: 14
<212> TYPE: PRT
<213> ORGANISM: Mus musculus

<400> SEQUENCE: 23

Arg Ser Ser Thr Gly Ala Val Thr Thr Ser Asn Tyr Ala Asn
1               5                   10

<210> SEQ ID NO 24
<211> LENGTH: 14
<212> TYPE: PRT
<213> ORGANISM: Mus musculus

<400> SEQUENCE: 24

Arg Ser Thr Thr Gly Ala Val Thr Thr Ser Asn Tyr Ala Asn
1               5                   10

<210> SEQ ID NO 25
<211> LENGTH: 14
<212> TYPE: PRT
<213> ORGANISM: Artificial sequence
<220> FEATURE:
<223> OTHER INFORMATION: HVR-L1 consensus sequence
<220> FEATURE:
<221> NAME/KEY: MISC_FEATURE
<222> LOCATION: (3)..(3)
<223> OTHER INFORMATION: X=neutral hydrophilic amino acid residue
<220> FEATURE:
<221> NAME/KEY: MISC_FEATURE
<222> LOCATION: (14)..(14)
<223> OTHER INFORMATION: X=neutral hydrophilic or acidic amino acid
      residue

<400> SEQUENCE: 25

Arg Ser Xaa Thr Gly Ala Val Thr Thr Ser Asn Tyr Ala Xaa
1               5                   10

<210> SEQ ID NO 26
<211> LENGTH: 7
<212> TYPE: PRT
<213> ORGANISM: Mus musculus

<400> SEQUENCE: 26

Gly Thr Asn Lys Arg Ala Pro
1               5

<210> SEQ ID NO 27
<211> LENGTH: 7
<212> TYPE: PRT
<213> ORGANISM: Artificial sequence
<220> FEATURE:
<223> OTHER INFORMATION: HVR-L2 consensus sequence
<220> FEATURE:
<221> NAME/KEY: MISC_FEATURE
<222> LOCATION: (4)..(4)
<223> OTHER INFORMATION: X=acidic or basic amino acid residue

<400> SEQUENCE: 27

Gly Thr Asn Xaa Arg Ala Pro
```

```
<210> SEQ ID NO 28
<211> LENGTH: 9
<212> TYPE: PRT
<213> ORGANISM: Mus musculus

<400> SEQUENCE: 28

Val Leu Trp Tyr Ser Asn His Trp Val
1               5

<210> SEQ ID NO 29
<211> LENGTH: 9
<212> TYPE: PRT
<213> ORGANISM: Mus musculus

<400> SEQUENCE: 29

Ala Leu Trp Tyr Ser Asp His Trp Val
1               5

<210> SEQ ID NO 30
<211> LENGTH: 9
<212> TYPE: PRT
<213> ORGANISM: Mus musculus

<400> SEQUENCE: 30

Ala Leu Trp Tyr Ser Asn His Trp Val
1               5

<210> SEQ ID NO 31
<211> LENGTH: 9
<212> TYPE: PRT
<213> ORGANISM: Artificial sequence
<220> FEATURE:
<223> OTHER INFORMATION: HVR-L3 consensus sequence
<220> FEATURE:
<221> NAME/KEY: misc_feature
<222> LOCATION: (1)..(1)
<223> OTHER INFORMATION: Xaa can be any naturally occurring amino acid
<220> FEATURE:
<221> NAME/KEY: misc_feature
<222> LOCATION: (6)..(6)
<223> OTHER INFORMATION: Xaa can be any naturally occurring amino acid

<400> SEQUENCE: 31

Xaa Leu Trp Tyr Ser Xaa His Trp Val
1               5

<210> SEQ ID NO 32
<211> LENGTH: 16
<212> TYPE: PRT
<213> ORGANISM: Mus musculus

<400> SEQUENCE: 32

Arg Ser Ser Gln Thr Ile Val His Ser Thr Gly His Thr Tyr Leu Glu
1               5                   10                  15

<210> SEQ ID NO 33
<211> LENGTH: 16
<212> TYPE: PRT
<213> ORGANISM: Artificial sequence
<220> FEATURE:
<223> OTHER INFORMATION: HVR-L1 consensus sequence
<220> FEATURE:
<221> NAME/KEY: MISC_FEATURE
<222> LOCATION: (9)..(9)
<223> OTHER INFORMATION: X=neutral or chain orientation influencing
      amino acid residue
```

```
<400> SEQUENCE: 33

Arg Ser Ser Gln Thr Ile Val His Xaa Thr Gly His Thr Tyr Leu Glu
1               5                   10                  15

<210> SEQ ID NO 34
<211> LENGTH: 7
<212> TYPE: PRT
<213> ORGANISM: Mus musculus

<400> SEQUENCE: 34

Lys Val Ser Asn Arg Phe Ser
1               5

<210> SEQ ID NO 35
<211> LENGTH: 9
<212> TYPE: PRT
<213> ORGANISM: Mus musculus

<400> SEQUENCE: 35

Phe Gln Gly Ser His Val Pro Tyr Thr
1               5
```

ANTI-VARIANT FC-REGION ANTIBODIES AND METHOD OF USE

CROSS REFERENCE TO RELATED APPLICATIONS

This application is a continuation of PCT International Application No. PCT/EP2016/075884, filed on Oct. 27, 2016, which is hereby incorporated by reference in its entirety, and which claims the benefit of priority of EP Application No. 15192195.4, filed Oct. 29, 2015.

SEQUENCE LISTING

The instant application contains a sequence listing which has been submitted via EFS-Web and is hereby incorporated by reference in its entirety. Said ASCII copy, created on Apr. 19, 2018, is named P33184-US_Sequence_Listing.txt and is 15,982 bytes in size.

FIELD OF THE INVENTION

The present invention relates to antibodies against variant Fc-regions (anti-variant Fc-region antibodies) which specifically bind to variant Fc-regions while not binding to the corresponding wild-type Fc-region. Also reported herein are methods for their production and uses thereof.

BACKGROUND

Since the development of the first monoclonal antibodies by Koehler and Milstein in 1974 a lot of efforts have been dedicated to the development of antibodies which are appropriate for therapy in humans. The first monoclonal antibodies which became available had been developed in mice and rats. These antibodies when used for therapy of a human being caused unwanted side effects due to anti-rodent antibodies. A lot of efforts have been dedicated to the reduction or even elimination of such unwanted side effects.

In the past years an ever growing number of human monoclonal antibodies or humanized monoclonal antibodies have reached the market. Well-known examples include for example Herceptin® and MabThera® from Hoffmann-La Roche, Basel.

A quite significant number of human or humanized monoclonal antibodies is under investigation and needs to be studied in experimental animals, before entry into human can be considered for the first trial purposes.

Important criteria like bio-availability and antibody clearance just to mention two of them have to be studied by the aid of experimental animals. Many of these studies require the quantification of the therapeutic antibody in the background of the host's own antibodies. In most cases mammals are used as experimental animals. Toxicology often is first assessed in rodents like mice or rats. In the more advanced stages of drug development, especially before entry of the drug into human beings, even monkeys have to be included into such pre-clinical studies.

Mammals usually have between about 10 to about 30 milligram of immunoglobulin per ml in the circulation.

Therapeutic monoclonal antibodies typically have to be tested with serum levels ranging from about between 1 nanogram per ml to about 100 microgram per ml. The therapeutic antibody thus has to be detected against a background of host antibodies which is in an excess of about 100-fold to 10 million-fold. The detection of a human or humanized therapeutic antibody in the background of host immunoglobulin represents quite a significant task to the pharmacologist. In addition it will be appreciated that different therapeutic antibodies may require different reagents and assay formats. The detection of a human or humanized antibody becomes more and more difficult the closer the therapeutic antibody is related to wild-type human antibodies.

Presently, the enzyme linked immunosorbent sandwich assay (ELISA) bridging assay (FIG. 1A) represents the state of the art assay format for immunogenicity testing due to its high throughput and sensitivity and its easy applicability to different projects (Mikulskis, A., et al., J. Immunol. Meth. 365 (2011) 38-49). However, reliability of this assay is challenged by both the interference due to oligomeric target leading to false positive results (Bautista, A. C., et al., Bioanal. 2 (2010) 721-731; Mire-Sluis, A. R., et al., J. Immunol. Meth. 289 (2004) 1-16 (2004); Weeraratne, D. K., et al., J. Immunol. Meth. 396 (2013) 44-55; Zhong, Z. D., et al., J. Immunol. Meth. 355 (2010) 21-28) and the presence of high drug concentrations in clinical samples that competes with labelled drug molecules and thus prevents ADAs from generating signals, thereby leading to false negative results (Mire-Sluis, A. R., et al., J. Immunol. Meth. 289 (2004) 1-16 (2004); Geng, D., et al., J. Pharm. Biomed. Anal. 39 (2005) 364-375). In particular, the detection of ADA bound in drug immune-complexes is significantly restricted in traditional bridging assays (Mire-Sluis, A. R., et al., J. Immunol. Meth. 289 (2004) 1-16 (2004); Geng, D., et al., J. Pharm. Biomed. Anal. 39 (2005) 364-375).

SUMMARY

Since bridging assays for detection of anti-drug antibodies (ADAs) are often hampered by oligomeric targets and high drug concentrations, improved approaches are required. For therapeutic antibodies lacking Fc effector functions, e.g. by introduction of a Pro329Gly (PG) substitution within the Fc-region, a drug- and target-tolerant immune complex assay is reported herein, employing a capture antibody specific for the substitution within the Fc-region, e.g. an anti-PG antibody, and a human soluble Fcγ receptor for detection. The assay as reported herein has increased drug an oligomeric target tolerance compared to the conventional bridging assay (Wessels, U., et al., Bioanalysis 8 (2016) 2135-2145). Even in the presence of high drug concentrations this method allows the determination of anti-drug antibodies because the human soluble Fcgamma receptor, such as e.g. the human soluble FcγRI, specifically binds to wild-type (wt) IgG but no to Fc-region modified IgG.

In combination with a bridging assay a detailed ADA characterization of clinical samples is now possible, because both assays differentially recognize ADA Ig-subtypes. With the assay as reported herein conventional bridging assay are complemented for in-depth characterization of individual ADA-responses against Fc-region-modified therapeutic antibodies.

One aspect as reported herein is an assay for the determination of the presence and/or amount of anti-drug antibodies in a (serum containing) sample comprising the following steps:

incubating the sample with an antibody specifically binding to an antibody lacking Fc effector function (by introduction of one or more substitution(s) within the Fc-region) to capture the antibody lacking Fc effector function from the sample (including free and ADA complexed antibody), detecting the captured antibody by incubating the captured antibody with human soluble FcγRI, and determining the presence and/or amount of anti-drug antibody in the sample.

One aspect as reported herein is a method for the in vitro determination of the presence and/or the amount of a binding partner, which can be specifically bound by a first binding specificity of a multispecific binder, wherein binding partner bound to the multispecific binder is depleted prior to the detection of the binding partner by incubating the sample with a monospecific binder specifically binding to a second binding specificity of the multispecific binder, comprising the following steps:

incubating a sample comprising binding partner and multispecific binder with an monospecific binder that specifically binds to a second binding specificity of the multispecific binder which is different from the first binding specificity, depleting the monospecific binder-multispecific binder-complex from the sample prior to the determination of the presence or the amount of free binding partner, and determining the amount of the binding partner in the multispecific binder-depleted sample with a method as reported in the previous aspect.

One aspect as reported herein is an isolated antibody that specifically binds to an Fc-region comprising at positions 253, 310 and 435 each the amino acid residue alanine (numbering according to Kabat EU index) comprising (a) a HVR-H1 comprising the amino acid sequence of SEQ ID NO: 09 or 10; (b) a HVR-H2 comprising the amino acid sequence of SEQ ID NO: 12, 13 or 14; (c) a HVR-H3 comprising the amino acid sequence of SEQ ID NO: 16, 17 or 18; (d) a HVR-L1 comprising the amino acid sequence of SEQ ID NO: 23 or 24; (e) a HVR-L2 comprising the amino acid sequence of SEQ ID NO: 26; and (f) a HVR-L3 comprising the amino acid sequence of SEQ ID NO: 28, 29 or 30.

This antibody is denoted as anti-AAA antibody in the following.

One aspect as reported herein is an isolated antibody that that specifically binds to an Fc-region comprising at position 329 the amino acid residue glycine (and optionally at positions 234 and 235 each the amino acid residue alanine) (numbering according to Kabat EU index) comprising (a) a HVR-H1 comprising the amino acid sequence of SEQ ID NO: 20; (b) a HVR-H2 comprising the amino acid sequence of SEQ ID NO: 21; (c) a HVR-H3 comprising the amino acid sequence of SEQ ID NO: 22; (d) a HVR-L1 comprising the amino acid sequence of SEQ ID NO: 32; (e) a HVR-L2 comprising the amino acid sequence of SEQ ID NO: 34; and (f) a HVR-L3 comprising the amino acid sequence of SEQ ID NO: 35.

This antibody is denoted as anti-PG antibody in the following.

In one embodiment the antibody is a monoclonal antibody.

In one embodiment the antibody is a human, humanized, or chimeric antibody.

In one embodiment the antibody is an antibody fragment that specifically binds to the respective mutated Fc-region.

One aspect as reported herein is an isolated nucleic acid encoding an antibody as reported herein.

One aspect as reported herein is a host cell comprising the nucleic acid as reported herein.

In one embodiment the host cell is a eukaryotic cell. In one embodiment the eukaryotic cell is a mammalian cell. In one preferred embodiment the mammalian cell is a CHO cell or a HEK cell.

One aspect is a method of producing an antibody comprising culturing the host cell as reported herein so that the antibody is produced.

In one embodiment comprises the method the steps of cultivating the cell as reported herein comprising the nucleic acid encoding the antibody as reported herein and recovering the antibody from the cell or the cultivation medium.

One aspect as reported herein is a conjugate comprising the antibody as reported herein conjugated to a detectable label.

One aspect as reported herein is the use of an antibody as reported herein in an immunoassay either as capture antibody or as tracer antibody for the determination of a therapeutic antibody of the IgG1 or IgG4 subclass comprising the mutation P329G or the mutations P329G/L234A/L235A or the mutations I253A/H310A/H435A in the Fc-region (in a sample) (numbering according to Kabat EU index).

One aspect as reported herein is the use of two different antibodies as reported herein in an immunoassay as capture antibody and as tracer antibody for the determination of a therapeutic antibody of the IgG1 or IgG4 subclass comprising the mutations I253A/H310A/H435A in a sample whereby the capture antibody and the tracer antibody differ in their HVR sequences (numbering according to Kabat EU index).

One aspect as reported herein is the use of an antibody as reported herein in an immunoassay either as capture antibody or as tracer antibody for the determination of anti-drug antibodies against a therapeutic antibody of the IgG1 or IgG4 subclass wherein the Fc-region of the therapeutic antibody comprises the mutation P329G or the mutations P329G/L234A/L235A or the mutations I253A/H310A/H435A (in a sample) (numbering according to Kabat EU index).

BRIEF DESCRIPTION OF THE FIGURES

FIG. 1 Scheme of an immunoassay using the antibody as reported herein as capture reagent.

FIG. 2 Scheme of an immunoassay using the antibody as reported herein as tracer reagent.

FIG. 5 Scheme of an immunoassay using the antibody as reported herein as capture antibody and a soluble Fcgamma receptor as tracer molecule.

DETAILED DESCRIPTION OF EMBODIMENTS OF THE INVENTION

I. Definitions

Figure 3:
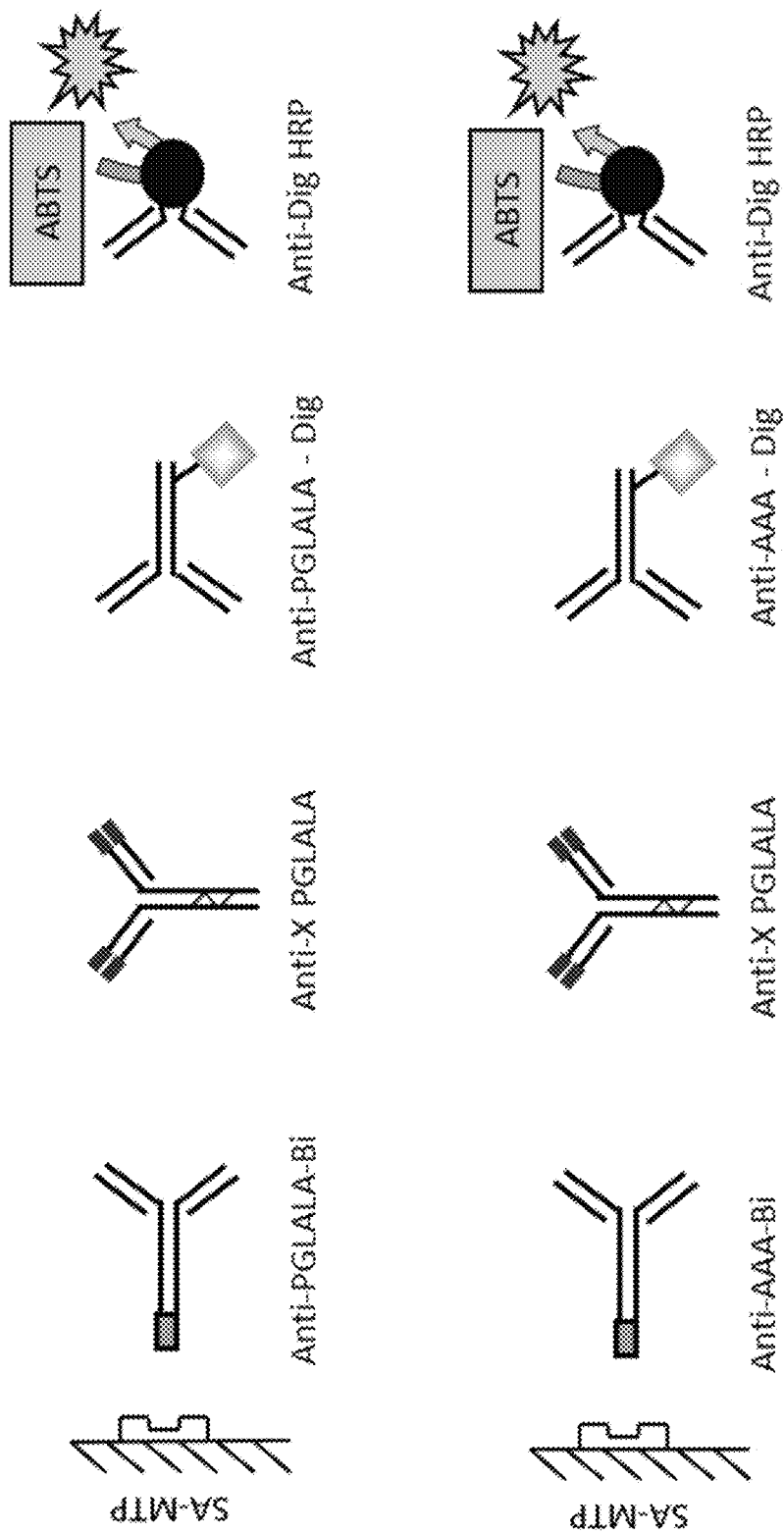
FIG. 3 Scheme of an immunoassay using the antibody as reported herein as capture and as tracer reagent.
Figure 4:
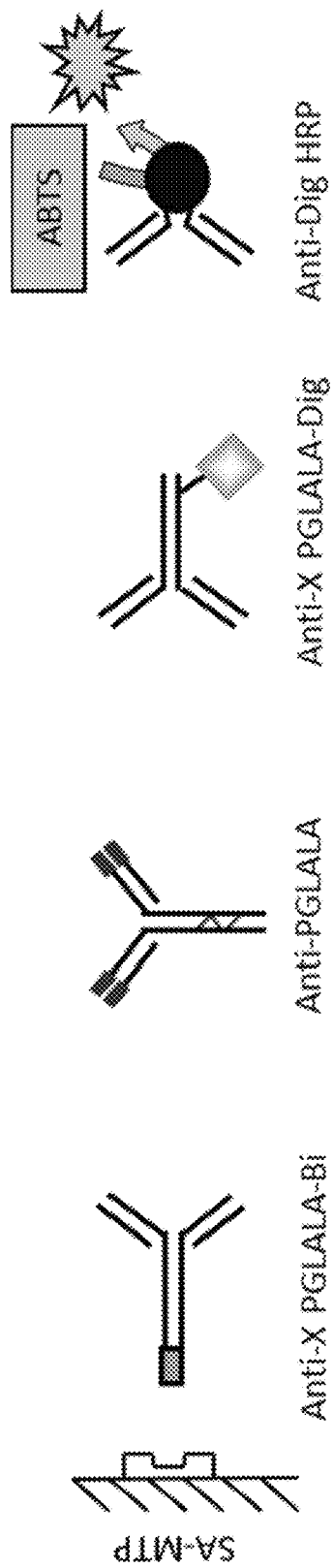
FIG. 4 Scheme of an immunoassay using the antibody as reported herein as standard.

As used herein, the amino acid positions of all constant regions and domains of the heavy and light chain are numbered according to the Kabat numbering system described in Kabat, et al., Sequences of Proteins of Immunological Interest, 5th ed., Public Health Service, National Institutes of Health, Bethesda, Md. (1991) and is referred to as "numbering according to Kabat" herein. Specifically the Kabat numbering system (see pages 647-660) of Kabat, et al., Sequences of Proteins of Immunological Interest, 5th ed., Public Health Service, National Institutes of Health, Bethesda, Md. (1991) is used for the light chain constant domain CL of kappa and lambda isotype and the Kabat EU index numbering system (see pages 661-723) is used for the constant heavy chain domains (CH1, Hinge, CH2 and CH3).

An "acceptor human framework" for the purposes herein is a framework comprising the amino acid sequence of a light chain variable domain (VL) framework or a heavy chain variable domain (VH) framework derived from a human immunoglobulin framework or a human consensus framework, as defined below. An acceptor human framework "derived from" a human immunoglobulin framework or a human consensus framework may comprise the same amino acid sequence thereof, or it may contain amino acid sequence changes. In some embodiments, the number of amino acid changes are 10 or less, 9 or less, 8 or less, 7 or less, 6 or less, 5 or less, 4 or less, 3 or less, or 2 or less. In some embodiments, the VL acceptor human framework is identical in sequence to the VL human immunoglobulin framework sequence or human consensus framework sequence.

"Affinity" refers to the strength of the sum total of non-covalent interactions between a single binding site of a molecule (e.g., an antibody) and its binding partner (e.g., an antigen). Unless indicated otherwise, as used herein, "binding affinity" refers to intrinsic binding affinity which reflects a 1:1 interaction between members of a binding pair (e.g., antibody and antigen). The affinity of a molecule X for its partner Y can generally be represented by the dissociation constant ($k_d$). Affinity can be measured by common methods known in the art, including those described herein.

An "affinity matured" antibody refers to an antibody with one or more alterations in one or more hypervariable regions (HVRs), compared to a parent antibody which does not possess such alterations, such alterations resulting in an improvement in the affinity of the antibody for antigen.

The term "alteration" denotes the mutation, addition, or deletion of one or more amino acid residues in a parent amino acid sequence, e.g. of an antibody or fusion polypeptide comprising at least an FcRn binding portion of an Fc-region, to obtain a variant antibody or fusion polypeptide.

The term "amino acid mutation" denotes a modification in the amino acid sequence of a parent amino acid sequence. Exemplary modifications include amino acid substitutions, insertions, and/or deletions. In one embodiment the amino acid mutation is a substitution. The term "amino acid mutations at the position" denotes the substitution or deletion of the specified residue, or the insertion of at least one amino acid residue adjacent the specified residue. The term "insertion adjacent to a specified residue" denotes the insertion within one to two residues thereof. The insertion may be N-terminal or C-terminal to the specified residue.

The term "amino acid substitution" denotes the replacement of at least one amino acid residue in a predetermined parent amino acid sequence with a different "replacement" amino acid residue. The replacement residue or residues may be a "naturally occurring amino acid residue" (i.e. encoded by the genetic code) and selected from the group consisting of: alanine (Ala); arginine (Arg); asparagine (Asn); aspartic acid (Asp); cysteine (Cys); glutamine (Gln); glutamic acid (Glu); glycine (Gly); histidine (His); isoleucine (Ile): leucine (Leu); lysine (Lys); methionine (Met); phenylalanine (Phe); proline (Pro); serine (Ser); threonine (Thr); tryptophan (Trp); tyrosine (Tyr); and valine (Val). In one embodiment the replacement residue is not cysteine. Substitution with one or more non-naturally occurring amino acid residues is also encompassed by the definition of an amino acid substitution herein. A "non-naturally occurring amino acid residue" denotes a residue, other than those naturally occurring amino acid residues listed above, which is able to covalently bind adjacent amino acid residues(s) in a polypeptide chain. Examples of non-naturally occurring amino acid residues include norleucine, ornithine, norvaline, homoserine, aib and other amino acid residue analogues such as those described in Ellman, et al., Meth. Enzym. 202 (1991) 301-336. To generate such non-naturally occurring amino acid residues, the procedures of Noren, et al. (Science 244 (1989) 182) and/or Ellman, et al. (supra) can be used. Briefly, these procedures involve chemically activating a suppressor tRNA with a non-naturally occurring amino acid residue followed by in vitro transcription and translation of the RNA. Non-naturally occurring amino acids can also be incorporated into peptides via chemical peptide synthesis and subsequent fusion of these peptides with recombinantly produced polypeptides, such as antibodies or antibody fragments.

The term "amino acid insertion" denotes the incorporation of at least one additional amino acid residue into a predetermined parent amino acid sequence. While the insertion will usually consist of the insertion of one or two amino acid residues, the present application contemplates larger "peptide insertions", e.g. insertion of about three to about five or even up to about ten amino acid residues. The inserted residue(s) may be naturally occurring or non-naturally occurring as defined above.

The term "amino acid deletion" denotes the removal of at least one amino acid residue at a predetermined position in an amino acid sequence.

Within this application whenever an amino acid alteration is mentioned it is a deliberated amino acid alteration and not a random amino acid modification.

The terms "anti-variant (human) Fc-region antibody" and "an antibody that specifically binds to a variant (human) Fc-region" refer to an antibody that is capable of binding a variant (human) Fc-region with sufficient affinity such that the antibody is useful as a diagnostic agent in targeting a variant (human) Fc-region. In one embodiment, the extent of binding of an anti-variant (human) Fc-region antibody to the corresponding wild-type (human) Fc-region is less than about 10% of the binding of the antibody to the variant (human) Fc-region. This can be determined e.g. using Surface Plasmon Resonance. In certain embodiments, an antibody that specifically binds to a variant (human) Fc-region has a dissociation constant ($K_D$) of $10^{-8}$ M or less, e.g. from $10^{-8}$ M to $10^{-13}$ M, e.g., from $10^{-9}$ M to $10^{-13}$ M).

The term "antibody" herein is used in the broadest sense and encompasses various antibody structures, including but not limited to monoclonal antibodies, polyclonal antibodies, multispecific antibodies (e.g., bispecific antibodies), and antibody fragments so long as they exhibit the desired antigen-binding activity.

An "antibody fragment" refers to a molecule other than an intact antibody that comprises a portion of an intact antibody that binds the antigen to which the intact antibody binds. Examples of antibody fragments include but are not limited to Fv, Fab, Fab', Fab'-SH, F(ab')$_2$; diabodies; linear antibodies; single-chain antibody molecules (e.g. scFv); and multispecific antibodies formed from antibody fragments.

The term "binding to" denotes the binding of a first entity to a second entity, such as e.g. of an antibody to its antigen. This binding can be determined using, for example, a BIAcore® assay (GE Healthcare, Uppsala, Sweden).

For example, in one possible embodiment of the BIAcore® assay the antigen is bound to a surface and binding of the antibody is measured by surface plasmon resonance (SPR). The affinity of the binding is defined by the terms $k_a$ (association constant: rate constant for the association to form a complex), $k_d$ (dissociation constant; rate constant for the dissociation of the complex), and $K_D$ ($k_d/k_a$). Alternatively, the binding signal of a SPR sensorgram can be compared directly to the response signal of a reference, with respect to the resonance signal height and the dissociation behaviors.

The term "CH2 domain" denotes the part of an antibody heavy chain polypeptide that extends approximately from EU position 231 to EU position 340 (EU numbering system according to Kabat). The CH2 domain is unique in that it is not closely paired with another domain. Rather, two N-linked branched carbohydrate chains are interposed between the two CH2 domains of an intact native Fc-region. It has been speculated that the carbohydrate may provide a substitute for the domain-domain pairing and help stabilize the CH2 domain. Burton, Mol. Immunol. 22 (1985) 161-206.

The term "CH3 domain" denotes the part of an antibody heavy chain polypeptide that extends approximately from EU position 341 to EU position 446.

The term "chimeric" antibody refers to an antibody in which a portion of the heavy and/or light chain is derived from a particular source or species, while the remainder of the heavy and/or light chain is derived from a different source or species.

The "class" of an antibody refers to the type of constant domain or constant region possessed by its heavy chain. There are five major classes of antibodies: IgA, IgD, IgE, IgG, and IgM, and several of these may be further divided into subclasses (isotypes), e.g., IgG$_1$, IgG$_2$, IgG$_3$, IgG$_4$, IgA$_1$, and IgA$_2$. The heavy chain constant domains that correspond to the different classes of immunoglobulins are called α, δ, ε, γ, and μ, respectively.

The term "complement-dependent cytotoxicity (CDC)" refers to lysis of cells induced by the antibody as reported herein in the presence of complement. CDC is found if the antibody induces lysis of 20% or more of the target cells at a concentration of 30 µg/ml. Binding to the complement factor C1q can be measured in an ELISA. In such an assay in principle an ELISA plate is coated with concentration ranges of the antibody, to which purified human C1q or human serum is added. C1q binding is detected by an antibody directed against C1q followed by a peroxidase-labeled conjugate. Detection of binding (maximal binding Bmax) is measured as optical density at 405 nm (OD405) for peroxidase substrate ABTS® (2,2'-azino-di-[3-ethylbenzthiazoline-6-sulfonate (6)]).

"Effector functions" refer to those biological activities attributable to the Fc-region of an antibody, which vary with the antibody class. Examples of antibody effector functions include: C1q binding and complement dependent cytotoxicity (CDC); Fc receptor binding; antibody-dependent cell-mediated cytotoxicity (ADCC); phagocytosis; down regulation of cell surface receptors (e.g. B cell receptor); and B cell activation.

Fc receptor binding dependent effector functions can be mediated by the interaction of the Fc-region of an antibody with Fc receptors (FcRs), which are specialized cell surface receptors on hematopoietic cells. Fc receptors belong to the immunoglobulin superfamily, and have been shown to mediate both the removal of antibody-coated pathogens by phagocytosis of immune complexes, and the lysis of erythrocytes and various other cellular targets (e.g. tumor cells) coated with the corresponding antibody, via antibody dependent cell mediated cytotoxicity (ADCC) (see e.g. Van de Winkel, J. G. and Anderson, C. L., J. Leukoc. Biol. 49 (1991) 511-524). FcRs are defined by their specificity for immunoglobulin isotypes: Fc receptors for IgG antibodies are referred to as FcγR. Fc receptor binding is described e.g. in Ravetch, J. V. and Kinet, J. P., Annu. Rev. Immunol. 9 (1991) 457-492; Capel, P. J., et al., Immunomethods 4 (1994) 25-34; de Haas, M., et al., J. Lab. Clin. Med. 126 (1995) 330-341; Gessner, J. E., et al., Ann. Hematol. 76 (1998) 231-248.

Cross-linking of receptors for the Fc-region of IgG antibodies (FcγR) triggers a wide variety of effector functions including phagocytosis, antibody-dependent cellular cytotoxicity, and release of inflammatory mediators, as well as immune complex clearance and regulation of antibody production. In humans, three classes of FcγR have been characterized, which are:

FcγRI (CD64) binds monomeric IgG with high affinity and is expressed on macrophages, monocytes, neutrophils and eosinophils. Modification in the Fc-region IgG at least at one of the amino acid residues E233-G236, P238, D265, N297, A327 and P329 (numbering according to EU index of Kabat) reduce binding to FcγRI. IgG2 residues at positions 233-236, substituted into IgG1 and IgG4, reduced binding to FcγRI by $10^3$-fold and eliminated the human monocyte response to antibody-sensitized red blood cells (Armour, K. L., et al., Eur. J. Immunol. 29 (1999) 2613-2624).

FcγRII (CD32) binds complexed IgG with medium to low affinity and is widely expressed. This receptor can be divided into two sub-types, FcγRIIA and FcγRIIB FcγRIIA is found on many cells involved in killing (e.g. macrophages, monocytes, neutrophils) and seems able to activate the killing process. FcγRIIB seems to play a role in inhibitory processes and is found on B-cells, macrophages and on mast cells and eosinophils. On B-cells it seems to function to suppress further immunoglobulin production and isotype switching to, for example, the IgE class. On macrophages, FcγRIIB acts to inhibit phagocytosis as mediated through FcγRIIA. On eosinophils and mast cells the B-form may help to suppress activation of these cells through IgE binding to its separate receptor. Reduced binding for FcγRIIA is found e.g. for antibodies comprising an IgG Fc-region with mutations at least at one of the amino acid residues E233-G236, P238, D265, N297, A327, P329, D270, Q295, A327, R292, and K414 (numbering according to EU index of Kabat).

FcγRIII (CD16) binds IgG with medium to low affinity and exists as two types. FcγRIIIA is found on NK cells, macrophages, eosinophils and some monocytes and T cells and mediates ADCC. FcγRIIIB is highly expressed on neutrophils. Reduced binding to FcγRIIIA is found e.g. for antibodies comprising an IgG Fc-region with mutation at least at one of the amino acid residues E233-G236, P238, D265, N297, A327, P329, D270, Q295, A327, S239, E269, E293, Y296, V303, A327, K338 and D376 (numbering according to EU index of Kabat).

Mapping of the binding sites on human IgG1 for Fc receptors, the above mentioned mutation sites and methods for measuring binding to FcγRI and FcγRIIA are described in Shields, R. L., et al. J. Biol. Chem. 276 (2001) 6591-6604.

The term "Fc receptor" as used herein refers to activation receptors characterized by the presence of a cytoplasmatic ITAM sequence associated with the receptor (see e.g. Ravetch, J. V. and Bolland, S., Annu. Rev. Immunol. 19 (2001) 275-290). Such receptors are FcγRI, FcγRIIA and FcγRIIIA The term "no binding of FcγR" denotes that at an antibody concentration of 10 μg/ml the binding of an antibody as reported herein to NK cells is 10% or less of the binding found for anti-OX40L antibody LC.001 as reported in WO 2006/029879.

While IgG4 shows reduced FcR binding, antibodies of other IgG subclasses show strong binding. However Pro238, Asp265, Asp270, Asn297 (loss of Fc carbohydrate), Pro329 and 234, 235, 236 and 237 Ile253, Ser254, Lys288, Thr307, Gln311, Asn434, and His435 are residues which provide if altered also reduce FcR binding (Shields, R. L., et al. J. Biol. Chem. 276 (2001) 6591-6604; Lund, J., et al., FASEB J. 9 (1995) 115-119; Morgan, A., et al., Immunology 86 (1995) 319-324; and EP 0 307 434). In one embodiment the antibody as reported herein is of IgG1 or IgG2 subclass and comprises the mutation PVA236, GLPSS331, and/or L234A/L235A. In one embodiment the antibody as reported herein is of IgG4 subclass and comprises the mutation L235E. In one embodiment the antibody further comprises the mutation S228P.

The term "Fc-region" herein is used to define a C-terminal region of an immunoglobulin heavy chain that contains at least a portion of the constant region. The term includes native sequence Fc-regions and variant Fc-regions. In one embodiment, a human IgG heavy chain Fc-region extends from Cys226, or from Pro230, to the carboxyl-terminus of the heavy chain. However, the C-terminal lysine (Lys447) of the Fc-region may or may not be present. Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242.

The antibodies as reported herein comprise as Fc-region, in one embodiment an Fc-region derived from human origin. In one embodiment the Fc-region comprises all parts of the human constant region. The Fc-region of an antibody is directly involved in complement activation, C1q binding, C3 activation and Fc receptor binding. While the influence of an antibody on the complement system is dependent on certain conditions, binding to C1q is caused by defined binding sites in the Fc-region. Such binding sites are known in the state of the art and described e.g. by Lukas, T. J., et al., J. Immunol. 127 (1981) 2555-2560; Brunhouse, R., and Cebra, J. J., Mol. Immunol. 16 (1979) 907-917; Burton, D. R., et al., Nature 288 (1980) 338-344; Thommesen, J. E., et al., Mol. Immunol. 37 (2000) 995-1004; Idusogie, E. E., et al., J. Immunol. 164 (2000) 4178-4184; Hezareh, M., et al., J. Virol. 75 (2001) 12161-12168; Morgan, A., et al., Immunology 86 (1995) 319-324; and EP 0 307 434. Such binding sites are e.g. L234, L235, D270, N297, E318, K320, K322, P331 and P329 (numbering according to EU index of Kabat; Unless otherwise specified herein, numbering of amino acid residues in the Fc-region or constant region is according to the EU numbering system, also called the EU index, as described in Kabat, E. A. et al., Sequences of Proteins of Immunological Interest, 5th ed., Public Health Service, National Institutes of Health, Bethesda, Md. (1991), NIH Publication 91-3242). Antibodies of subclass IgG1, IgG2 and IgG3 usually show complement activation, C1q binding and C3 activation, whereas IgG4 do not activate the complement system, do not bind C1q and do not activate C3. An "Fc-region of an antibody" is a term well known to the skilled artisan and defined on the basis of papain cleavage of antibodies. In one embodiment the Fc-region is a human Fc-region. In one embodiment the Fc-region is of the human IgG4 subclass comprising the mutations S228P and/or L235E (numbering according to EU index of Kabat). In one embodiment the Fc-region is of the human IgG1 subclass comprising the mutations L234A and L235A (numbering according to EU index of Kabat).

"Framework" or "FR" refers to variable domain residues other than hypervariable region (HVR) residues. The FR of a variable domain generally consists of four FR domains: FR1, FR2, FR3, and FR4. Accordingly, the HVR and FR sequences generally appear in the following sequence in VH (or VL): FR1-H1(L1)-FR2-H2(L2)-FR3-H3(L3)-FR4.

The terms "full length antibody", "intact antibody", and "whole antibody" are used herein interchangeably to refer to an antibody having a structure substantially similar to a native antibody structure or having heavy chains that contain an Fc-region as defined herein.

The terms "host cell", "host cell line", and "host cell culture" are used interchangeably and refer to cells into which exogenous nucleic acid has been introduced, including the progeny of such cells. Host cells include "transformants" and "transformed cells," which include the primary transformed cell and progeny derived therefrom without regard to the number of passages. Progeny may not be completely identical in nucleic acid content to a parent cell, but may contain mutations. Mutant progeny that have the same function or biological activity as screened or selected for in the originally transformed cell are included herein.

A "human consensus framework" is a framework which represents the most commonly occurring amino acid residues in a selection of human immunoglobulin VL or VH framework sequences. Generally, the selection of human immunoglobulin VL or VH sequences is from a subgroup of variable domain sequences. Generally, the subgroup of sequences is a subgroup as in Kabat, E. A. et al., Sequences of Proteins of Immunological Interest, 5th ed., Bethesda Md. (1991), NIH Publication 91-3242, Vols. 1-3. In one embodiment, for the VL, the subgroup is subgroup kappa I as in Kabat et al., supra. In one embodiment, for the VH, the subgroup is subgroup III as in Kabat et al., supra.

A "humanized" antibody refers to a chimeric antibody comprising amino acid residues from non-human HVRs and amino acid residues from human FRs. In certain embodiments, a humanized antibody will comprise substantially all of at least one, and typically two, variable domains, in which all or substantially all of the HVRs (e.g., CDRs) correspond to those of a non-human antibody, and all or substantially all of the FRs correspond to those of a human antibody. A humanized antibody optionally may comprise at least a portion of an antibody constant region derived from a human antibody. A "humanized form" of an antibody, e.g., a non-human antibody, refers to an antibody that has undergone humanization.

The term "hypervariable region" or "HVR", as used herein, refers to each of the regions of an antibody variable domain comprising the amino acid residue stretches which are hypervariable in sequence ("complementarity determining regions" or "CDRs") and/or form structurally defined loops ("hypervariable loops"), and/or contain the antigen-contacting residues ("antigen contacts"). Generally, antibodies comprise six HVRs; three in the VH (H1, H2, H3), and three in the VL (L1, L2, L3).

HVRs include
(a) hypervariable loops occurring at amino acid residues 26-32 (L1), 50-52 (L2), 91-96 (L3), 26-32 (H1), 53-55 (H2), and 96-101 (H3) (Chothia, C. and Lesk, A. M., J. Mol. Biol. 196 (1987) 901-917);
(b) CDRs occurring at amino acid residues 24-34 (L1), 50-56 (L2), 89-97 (L3), 31-35b (H1), 50-65 (H2), and 95-102 (H3) (Kabat, E. A. et al., Sequences of Proteins of Immunological Interest, 5th ed. Public Health Service, National Institutes of Health, Bethesda, Md. (1991), NIH Publication 91-3242);
(c) antigen contacts occurring at amino acid residues 27c-36 (L1), 46-55 (L2), 89-96 (L3), 30-35b (H1), 47-58 (H2), and 93-101 (H3) (MacCallum et al. J. Mol. Biol. 262: 732-745 (1996)); and
(d) combinations of (a), (b), and/or (c), including amino acid residues 46-56 (L2), 47-56 (L2), 48-56 (L2), 49-56 (L2), 26-35 (H1), 26-35b (H1), 49-65 (H2), 93-102 (H3), and 94-102 (H3).

Unless otherwise indicated, HVR residues and other residues in the variable domain (e.g., FR residues) are numbered herein according to Kabat et al., supra.

The term "hinge region" denotes the part of an antibody heavy chain polypeptide that joins in a wild-type antibody heavy chain the CH1 domain and the CH2 domain, e. g. from about position 216 to about position 230 according to the EU number system of Kabat, or from about position 226 to about position 230 according to the EU number system of Kabat. The hinge regions of other IgG subclasses can be determined by aligning with the hinge-region cysteine residues of the IgG1 subclass sequence.

The hinge region is normally a dimeric molecule consisting of two polypeptides with identical amino acid sequence. The hinge region generally comprises about 25 amino acid residues and is flexible allowing the antigen binding regions to move independently. The hinge region can be subdivided into three domains: the upper, the middle, and the lower hinge domain (see e.g. Roux, et al., J. Immunol. 161 (1998) 4083).

In one embodiment the hinge region has the amino acid sequence DKTHTCPX4CP, wherein X4 is either S or P. In one embodiment the hinge region has the amino acid sequence HTCPX4CP, wherein X4 is either S or P. In one embodiment the hinge region has the amino acid sequence CPX4CP, wherein X4 is either S or P.

The term "lower hinge region" of an Fc-region denotes the stretch of amino acid residues immediately C-terminal to the hinge region, i.e. residues 233 to 239 of the Fc-region according to the EU numbering of Kabat.

An "individual" or "subject" is a mammal. Mammals include, but are not limited to, domesticated animals (e.g. cows, sheep, cats, dogs, and horses), primates (e.g., humans and non-human primates such as monkeys), rabbits, and rodents (e.g., mice and rats). In certain embodiments, the individual or subject is a human.

An "isolated" antibody is one which has been separated from a component of its natural environment. In some embodiments, an antibody is purified to greater than 95% or 99% purity as determined by, for example, electrophoretic (e.g., SDS-PAGE, isoelectric focusing (IEF), capillary electrophoresis) or chromatographic (e.g., ion exchange or reverse phase HPLC). For review of methods for assessment of antibody purity, see, e.g., Flatman, S. et al., J. Chromatogr. B 848 (2007) 79-87.

An "isolated" nucleic acid refers to a nucleic acid molecule that has been separated from a component of its natural environment. An isolated nucleic acid includes a nucleic acid molecule contained in cells that ordinarily contain the nucleic acid molecule, but the nucleic acid molecule is present extrachromosomally or at a chromosomal location that is different from its natural chromosomal location.

"Isolated nucleic acid encoding an anti-variant (human) Fc-region antibody" refers to one or more nucleic acid molecules encoding antibody heavy and light chains (or fragments thereof), including such nucleic acid molecule(s) in a single vector or separate vectors, and such nucleic acid molecule(s) present at one or more locations in a host cell.

The term "monoclonal antibody" as used herein refers to an antibody obtained from a population of substantially homogeneous antibodies, i.e., the individual antibodies comprising the population are identical and/or bind the same epitope, except for possible variant antibodies, e.g., containing naturally occurring mutations or arising during production of a monoclonal antibody preparation, such variants generally being present in minor amounts. In contrast to polyclonal antibody preparations, which typically include different antibodies directed against different determinants (epitopes), each monoclonal antibody of a monoclonal antibody preparation is directed against a single determinant on an antigen. Thus, the modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including but not limited to the hybridoma method, recombinant DNA methods, phage-display methods, and methods utilizing transgenic animals containing all or part of the human immunoglobulin loci, such methods and other exemplary methods for making monoclonal antibodies being described herein.

"Native antibodies" refer to naturally occurring immunoglobulin molecules with varying structures. For example, native IgG antibodies are heterotetrameric glycoproteins of about 150,000 daltons, composed of two identical light chains and two identical heavy chains that are disulfide-bonded. From N- to C-terminus, each heavy chain has a variable region (VH), also called a variable heavy domain or a heavy chain variable domain, followed by three constant domains (CH1, CH2, and CH3), whereby between the first and the second constant domain a hinge region is located. Similarly, from N- to C-terminus, each light chain has a variable region (VL), also called a variable light domain or a light chain variable domain, followed by a constant light (CL) domain. The light chain of an antibody may be assigned to one of two types, called kappa (κ) and lambda (λ), based on the amino acid sequence of its constant domain.

"Percent (%) amino acid sequence identity" with respect to a reference polypeptide sequence is defined as the percentage of amino acid residues in a candidate sequence that are identical with the amino acid residues in the reference polypeptide sequence, after aligning the sequences and introducing gaps, if necessary, to achieve the maximum percent sequence identity, and not considering any conservative substitutions as part of the sequence identity. Alignment for purposes of determining percent amino acid sequence identity can be achieved in various ways that are within the skill in the art, for instance, using publicly available computer software such as BLAST, BLAST-2, ALIGN or Megalign (DNASTAR) software. Those skilled in the art can determine appropriate parameters for aligning sequences, including any algorithms needed to achieve maximal alignment over the full length of the sequences being compared. For purposes herein, however, % amino acid sequence identity values are generated using the sequence comparison computer program ALIGN-2. The ALIGN-2 sequence comparison computer program was authored by Genentech, Inc., and the source code has been filed with user documentation in the U.S. Copyright Office, Washington D.C., 20559, where it is registered under U.S. Copyright Registration No. TXU510087. The ALIGN-2 program is publicly available from Genentech, Inc., South San Francisco, Calif., or may be compiled from the source code. The ALIGN-2 program should be compiled for use on a UNIX operating system, including digital UNIX V4.0D. All sequence comparison parameters are set by the ALIGN-2 program and do not vary.

In situations where ALIGN-2 is employed for amino acid sequence comparisons, the % amino acid sequence identity of a given amino acid sequence A to, with, or against a given amino acid sequence B (which can alternatively be phrased as a given amino acid sequence A that has or comprises a certain % amino acid sequence identity to, with, or against a given amino acid sequence B) is calculated as follows:

100 times the fraction X/Y where X is the number of amino acid residues scored as identical matches by the sequence alignment program ALIGN-2 in that program's alignment of A and B, and where Y is the total number of amino acid residues in B. It will be appreciated that where the length of amino acid sequence A is not equal to the length of amino acid sequence B, the % amino acid sequence identity of A to B will not equal the % amino acid sequence identity of B to A. Unless specifically stated otherwise, all % amino acid sequence identity values used herein are obtained as described in the immediately preceding paragraph using the ALIGN-2 computer program.

The terms "native Fc-region" and "wild-type Fc-region" as used herein, refers to any native or wild-type Fc-region from any vertebrate source, including mammals such as primates (e.g. humans) and rodents (e.g., mice and rats), unless otherwise indicated.

The term "variant (human) Fc-region" denotes an amino acid sequence which differs from that of a "native" or "wild-type" (human) Fc-region amino acid sequence by virtue of at least one "amino acid alteration/mutation". In one embodiment the variant Fc-region has at least one amino acid mutation compared to a native Fc-region, e.g. from about one to about ten amino acid mutations, and in one embodiment from about one to about five amino acid mutations in a native Fc-region. In one embodiment the (variant) Fc-region has at least about 80% homology with a wild-type Fc-region, and in one embodiment the variant Fc-region has least about 90% homology, in one embodiment the variant Fc-region has at least about 95% homology.

The variant Fc-regions as reported herein are defined by the amino acid alterations that are contained. Thus, for example, the term P329G denotes a variant Fc-region with the mutation of proline to glycine at amino acid position 329 relative to the parent (wild-type) Fc-region. The identity of the wild-type amino acid may be unspecified, in which case the aforementioned variant is referred to as 329G. The alteration can be an addition, deletion, or mutation. The term "mutation" denotes a change to naturally occurring amino acids as well as a change to non-naturally occurring amino acids (see e.g. U.S. Pat. No. 6,586,207, WO 98/48032, WO 03/073238, US 2004/0214988, WO 2005/35727, WO 2005/74524, Chin, J. W., et al., J. Am. Chem. Soc. 124 (2002) 9026-9027; Chin, J. W. and Schultz, P. G., ChemBioChem 11 (2002) 1135-1137; Chin, J. W., et al., PICAS United States of America 99 (2002) 11020-11024; Wang, L. and Schultz, P. G., Chem. (2002) 1-10).

The term "wild-type Fc-region" denotes an amino acid sequence identical to the amino acid sequence of an Fc-region found in nature. Wild-type human Fc-regions include a native human IgG1 Fc-region (non-A and A allotypes), native human IgG2 Fc-region, native human IgG3 Fc-region, and native human IgG4 Fc-region as well as naturally occurring variants thereof.

The term "therapeutic antibody" relates to any antibody preparation which is intended for use in a human being. Preferably such therapeutic antibody will be a monoclonal antibody. Further preferred such monoclonal antibody will be obtained from a great ape or be a human monoclonal antibody. Preferably, it will be a human monoclonal antibody. Also preferred such therapeutic monoclonal antibody will be a humanized monoclonal antibody.

The term "variable region" or "variable domain" refers to the domain of an antibody heavy or light chain that is involved in binding the antibody to antigen. The variable domains of the heavy chain and light chain (VH and VL, respectively) of a native antibody generally have similar structures, with each domain comprising four conserved framework regions (FRs) and three hypervariable regions (HVRs). (See, e.g., Kindt, T. J. et al. Kuby Immunology, 6th ed., W.H. Freeman and Co., N.Y. (2007), page 91) A single VH or VL domain may be sufficient to confer antigen-binding specificity. Furthermore, antibodies that bind a particular antigen may be isolated using a VH or VL domain from an antibody that binds the antigen to screen a library of complementary VL or VH domains, respectively (see, e.g., Portolano, S., et al., J. Immunol. 150 (1993) 880-887; Clackson, T., et al., Nature 352 (1991) 624-628).

The term "vector", as used herein, refers to a nucleic acid molecule capable of propagating another nucleic acid to which it is linked. The term includes the vector as a self-replicating nucleic acid structure as well as the vector incorporated into the genome of a host cell into which it has been introduced. Certain vectors are capable of directing the expression of nucleic acids to which they are operatively linked. Such vectors are referred to herein as "expression vectors".

II. Compositions and Methods

In one aspect, the invention is based, in part, on the finding that antibodies specifically binding to a variant (human) Fc-region can be provided that do not substantially bind to the corresponding wild-type (human) Fc-region. In certain embodiments, antibodies that specifically bind to a human Fc-region with the mutations P329G or L234A, L235A, P329G or I253A, H310A, H435A are provided (numbering according to EU index of Kabat). Antibodies of the invention are useful, e.g., for the determination of the respective therapeutic antibody in a sample or for the determination of anti-drug antibodies (ADA) against a therapeutic antibody.

A. Exemplary Anti-Fc-Region Antibodies

As described earlier for preclinical studies in cynomolgus or mice (Stubenrauch, K., et al., J. Pharm. Biomed. Anal. 52 (2010) 249-254; Moore, G. L., et al., MAbs 2 (2010) 181-189; Stubenrauch, K., et al., Anal. Biochem. 430 (2012) 193-199; Carrasco-Triguero, M., et al., J. Immunol. Res. 2016 2618575 (2016)), drug tolerance can be improved by generic or universal assay formats that detect complexes of drug and ADA (anti-drug antibody). Likewise, detection of drug-ADA complexes (drug=therapeutic antibody administered beforehand) by the assay as reported herein, e.g. the hsFcγRI-PG assay, requires no labeled drug antibody as capture or detection reagent. It has been found that this assay setup lead to improved drug tolerance. This has been confirmed in spiking experiments.

ng/ml control ADA were found positive in the presence of up to 25 µg/ml drug) was determined.

Figure 7:
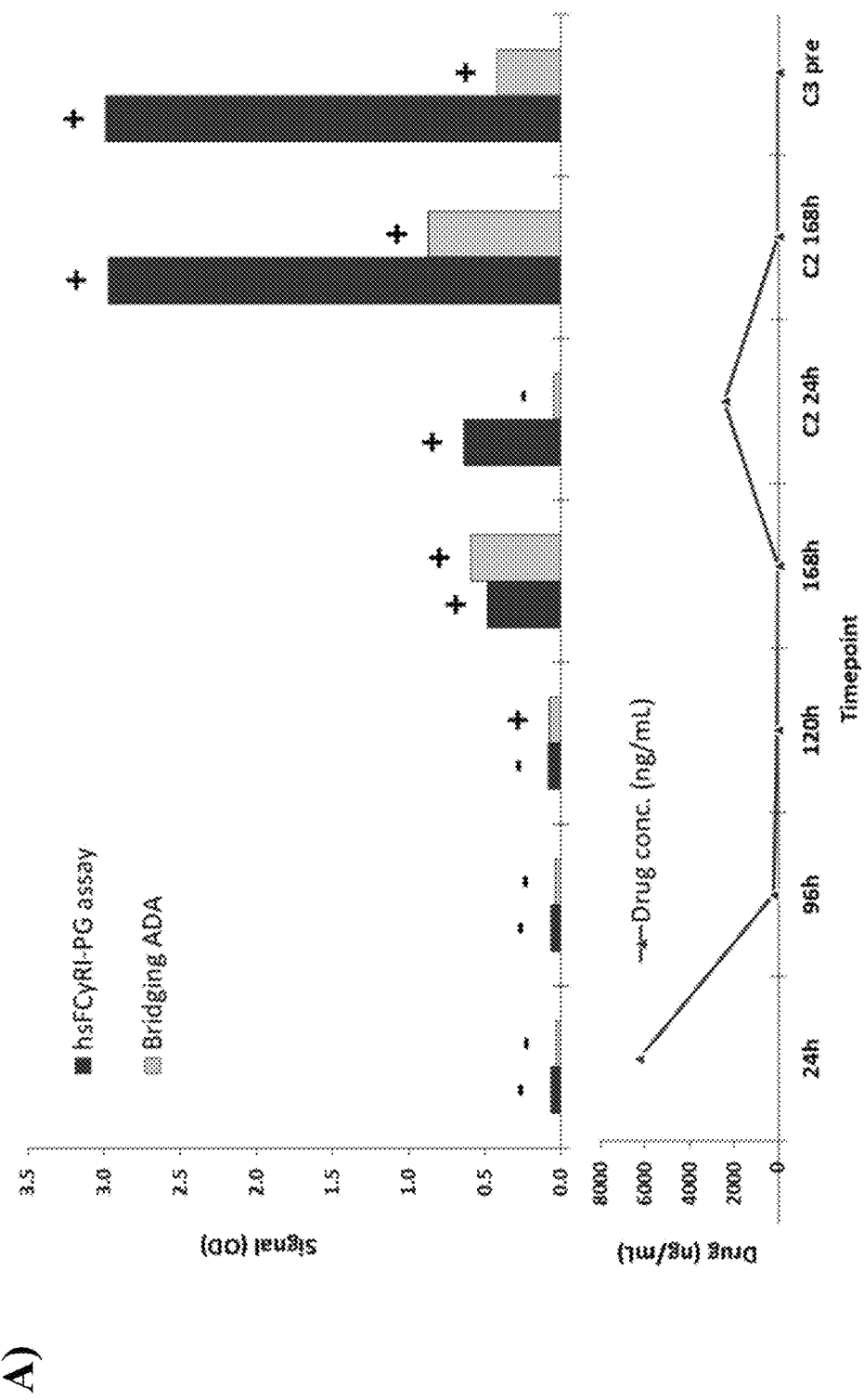
FIGS. 7A, 7B, 7C Exemplary time course of ADA occurrence in 4 patients of a clinical trial: patients had received biweekly (FIG. 7A, FIG. 7C) or weekly administrations (FIG. 7B) of the therapeutic antibody (10 mg each dose), and blood samples were collected daily before and after each dose (C2, C3: second and third treatment cycle). All samples were tested for anti-drug antibodies (ADAs) by both the conventional bridging (light grey bars) and the hsFcγRI-PG assay (black bars). Blood drug concentrations (ng/ml) are provided (bottom curve), and samples assessed as ADA negative (−) or positive (+) are indicated above the corresponding bars.
Figure 7:
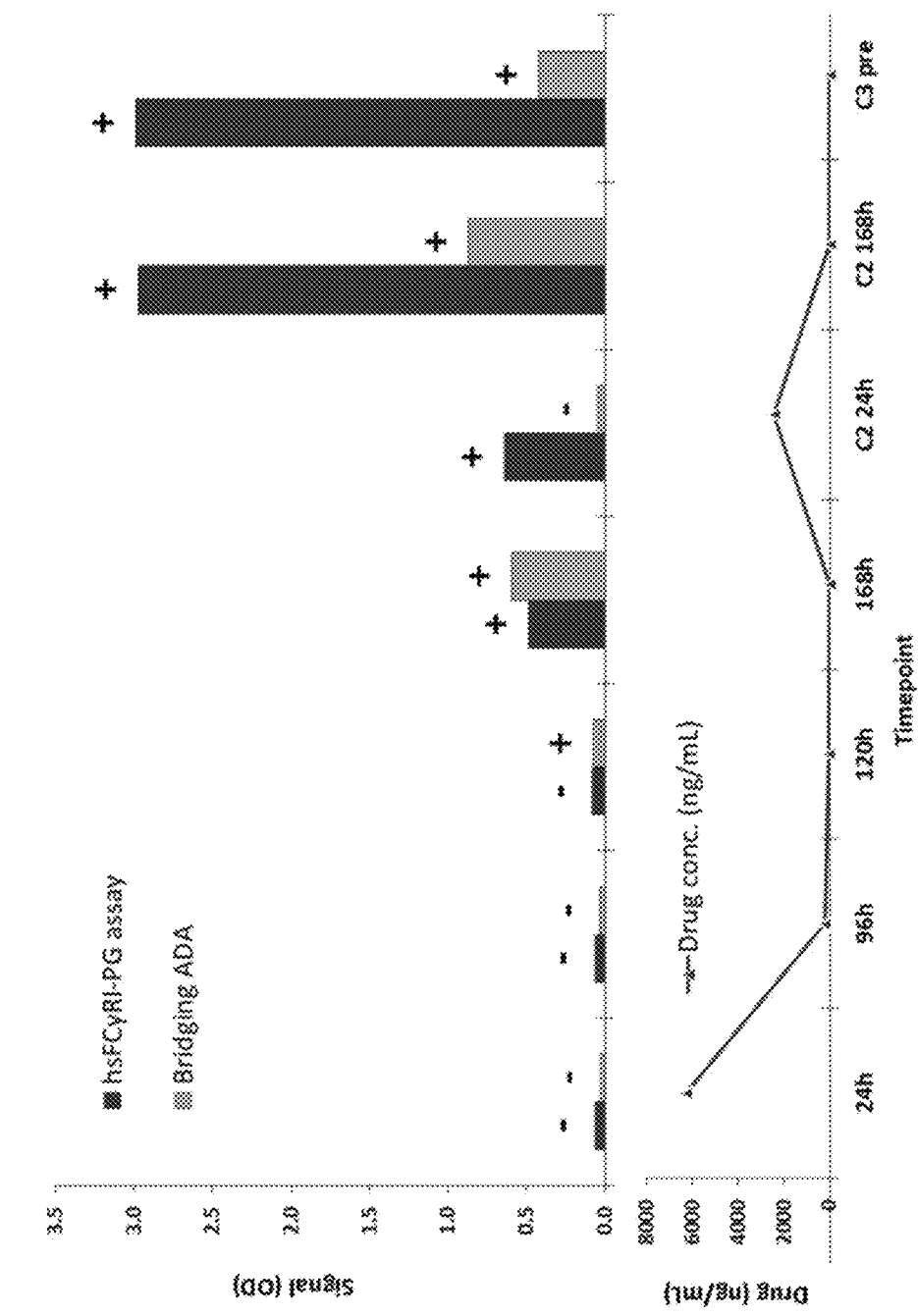
Figure 7:
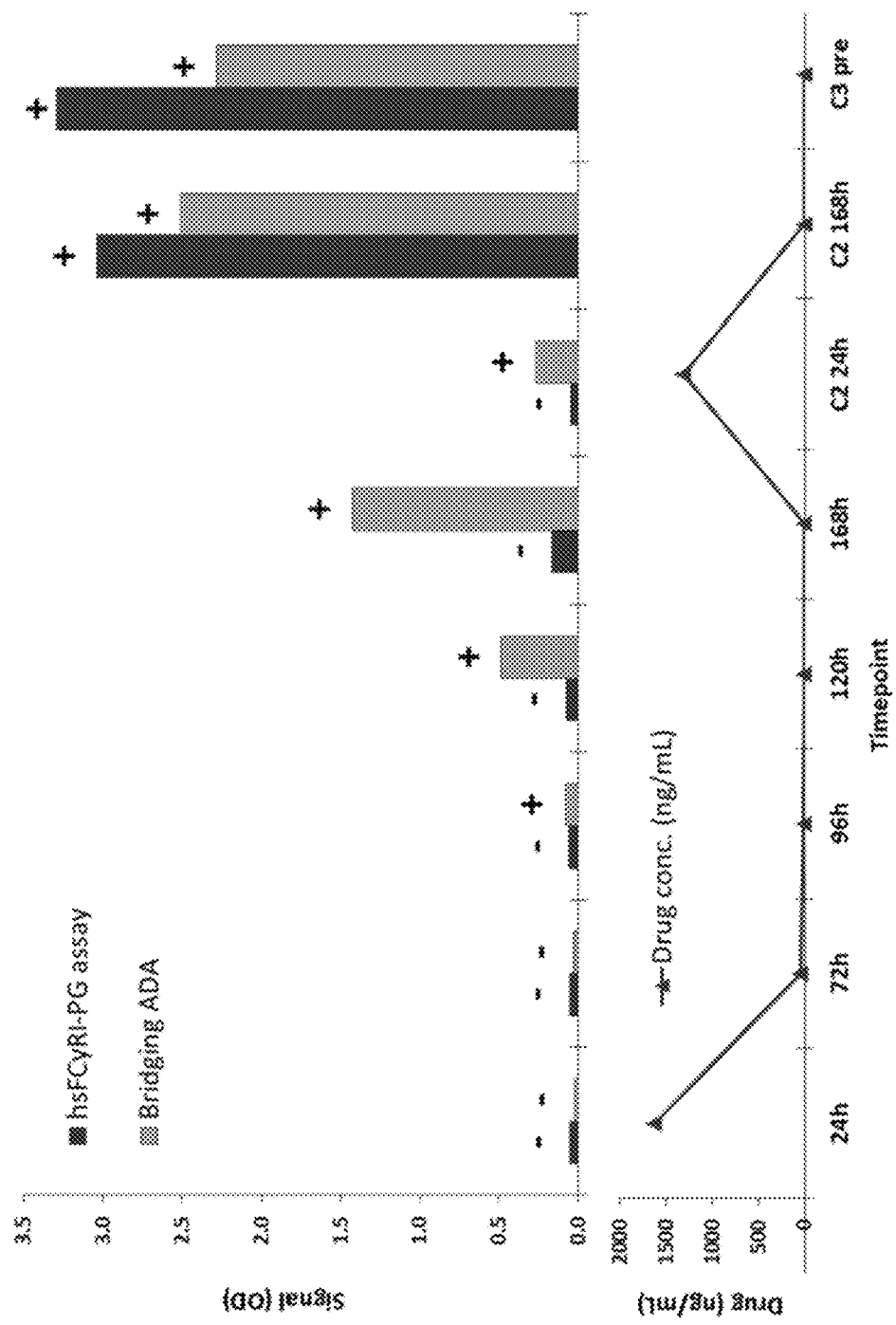

With the assay as reported herein and a standard bridging assay the time course of ADA occurrence was determined in clinical samples from four patients (FIG. 7). These datasets show in an exemplary way the differences of both assays regarding Drug tolerance, sensitivity and Ig isotype specificity.

In patient A (Table below; FIG. 7A), both assays show early ADA positivity at 120 h for the bridging assay and 168 h for the hsFcγRI-PG assay. The ADA signals at 168 h for both assays are comparable and significant with approximately 0.5 OD. The corresponding drug level in the samples is very low (about 2 ng/ml). At the next measured time point, 24 h after second dosing (C2 24 h), the drug level is much higher (about 2430 ng/mL). This influences the bridging assay, resulting in a major signal drop below the corresponding cut point. The hsFcγRI-PG assay in contrast is not affected by the drug and the ADA signal even rises from 168 h to C2 24 h.

Similar signal drops due to rising drug levels for the bridging assay were observed in other patient samples (see Table below). The signals of the hsFcγRI-PG assay were not affected in any of the patients, confirming the improved drug tolerance of this assay.

TABLE

Assessment of ADA formation in 8 patients by the conventional bridging and the hsFcγRI-PG assay as reported herein.

| | Biweekly dosed patients | | | | | | | | | | | |
|---|---|---|---|---|---|---|---|---|---|---|---|---|
| | Patient A | | | Patient C | | | Patient E | | | Patient F | | |
| Time point | hsFcγRI-PG | Bridging | Drug (ng/mL) | hsFcγRI-PG | Bridging | Drug (ng/mL) | hsFcγRI-PG | Bridging | Drug (ng/mL) | hsFcγRI-PG | Bridging | Drug (ng/mL) |
| 24 h | − | − | 6250 | − | − | 1620 | − | − | 212 | − | − | 2350 |
| 72 h | n.d. | n.d. | n.d. | − | − | 43 | n.d. | n.d. | n.d. | − | − | 97 |
| 96 h | − | − | 218 | − | + | 6 | − | − | 4 | − | + | 11 |
| 120 h | − | + | 27 | − | + | 3 | − | − | 3 | + | + | BLQ |
| 168 h | + | + | 2 | − | + | 2 | − | − | 2 | n.d. | n.d. | n.d. |
| C2 Pre | n.d. | n.d. | n.d. | n.d. | n.d. | n.d. | − | − | BLQ | + | + | BLQ |
| C2 24 h | + | − | 2430 | − | + | 1310 | − | − | 545 | + | + | 1010 |
| C2 168 h | + | + | BLQ | + | + | BLQ | + | − | BLQ | + | + | BLQ |
| C3 pre | + | + | BLQ | + | + | BLQ | + | − | BLQ | + | + | BLQ |

| | Weekly dosed patients | | | | | | | | | | | |
|---|---|---|---|---|---|---|---|---|---|---|---|---|
| | Patient B | | | Patient D | | | Patient G | | | Patient H | | |
| Time point | hsFcγRI-PG | Bridging | Drug (ng/mL) | hsFcγRI-PG | Bridging | Drug (ng/mL) | hsFcγRI-PG | Bridging | Drug (ng/mL) | hsFcγRI-PG | Bridging | Drug (ng/mL) |
| 24 h | − | − | 885 | − | − | 722 | − | − | 2820 | − | − | 1800 |
| 72 h | − | − | 3 | − | − | 62 | − | − | 262 | − | − | 70 |
| 96 h | − | + | 4 | − | − | 7 | − | + | 3 | − | − | 6 |
| C2 Pre | + | + | 1 | + | + | BLQ | + | + | BLQ | + | + | BLQ |
| C2 24 h | + | − | 144 | n.d. | n.d. | n.d. | + | − | 263 | + | + | 547 |
| C2 96 h | + | − | BLQ | + | + | 10 | + | + | BLQ | + | + | BLQ |
| C3 pre | + | + | BLQ | − | + | 1 | + | + | BLQ | + | + | BLQ |
| C3 24 h | + | − | 176 | n.d. | n.d. | n.d. | n.d. | n.d. | n.d. | + | + | 14 |
| C3 96 h | + | − | 1 | − | + | 8 | n.d. | n.d. | n.d. | + | + | BLQ |

The drug tolerance factor is the ratio between the amount of positively detectable positive control and the amount of drug present in the sample. For the bridging assay, a drug tolerance factor of 6 (500 ng/mL positive control could be detected in the presence of up to 3 µg/mL drug) whereas for the hsFcγRI-PG assay a drug tolerance factor of 833 (30

FIG. 7B shows the time course of patient B (Table above). After initial positivity at 96 h, the bridging assay shows very low signals over the next 6 time points with 4 signals even below cut-point, resulting in negative classification of these samples. This may be due to rising drug levels for time-points C2 24 h and C3 24 h, but even with drug levels below limit of quantification (C3 pre) samples show ADA signals below cut point in the bridging assay.

The hsFcγRI-PG assay also shows early positivity at C2 24 h. But, this patient stays positive with significant signals during the whole time course. This indicates a better sensitivity for the hsFcγRI-PG assay compared to the bridging assay. Patient A (Table above; FIG. 7A) also shows much higher signals for very late time points in the hsFcγRI-PG assay compared to the bridging assay. One patient was negative in the bridging assay over the whole time course and was detected positive in the hsFcγRI-PG assay for the last 2 time points.

Also considering the different dilution factors for both assays with 1 to 50 diluted samples in the hsFcγRI-PG assay and 1 to 10 diluted samples in the bridging assay, the hsFcγRI-PG assay is more sensitive, especially for late ADA responses, even leading to a qualitative difference in ADA positivity in some study samples.

In contrast, the bridging assay has a much lower cut-point than the hsFcγRI-PG assay and for early ADA responses the bridging assay shows higher signals than the hsFcγRI-PG assay. For some patients, the standard bridging assay showed earlier ADA positivity and/or higher signal intensities for early ADA responses than did the hsFcγRI-PG assay. This can be observed for example for patient C (Table above; FIG. 7C). While the bridging assay shows positivity for all samples from 96 h on, the hsFcγRI-PG assay only show positive ADA positivity for the last 2 time points. Since the hsFcγRI-PG assay exclusively detects IgG but no IgM (Fridman, W. H., FASEB J. 5 (1991) 2684-2690), the first peak of ADA positivity observed by the bridging assay might very likely reflect an IgM response, because IgM is usually the first antibody class to appear in response to an initial antigen exposure (Stewart, J. J., et al., Autoimmunity 44 (2011) 294-303). This pattern of higher ADA responses in the bridging assay in early samples, indicating IgM responses could be observed in ⅗ patients. Patient D (Table above) was especially critical, since it showed an early ADA response for the bridging assay with a transient progression. The hsFcγRI-PG assay showed only weak ADA positivity with a similar transient progression, indicating a mixed IgM, IgG response with a predominant proportion of IgM.

Especially for patients with high levels of rheumatoid factor, IgM can be a problem for bridging ADA assays, resulting in false positive results (Stubenrauch, K., et al., Clin. Ther. 32 (2010) 1597-1609).

Combination of both assay formats allows for interpretation regarding ADA responses, which would not have been possible with just one assay.

The assay as reported herein and the standard bridging assay differ in the principles of ADA capturing and detection. In the bridging assay, ADAs are both captured and detected by the differentially labelled drug molecules. As a result, oligomeric target can generate false positive results, and drug tolerance is usually low (Bautista, A. C., et al., Bioanal. 2 (2010) 721-731; Mire-Sluis, A. R., et al., J. Immunol. Meth. 289 (2004) 1-16 (2004); Weeraratne, D. K., et al., J. Immunol. Meth. 396 (2013) 44-55; Zhong, Z. D., et al., J. Immunol. Meth. 355 (2010) 21-28). However, the bridging assay is able to detect ADA of various Ig-subtypes including IgM and is applicable to all kinds of therapeutic antibodies (Mire-Sluis, A. R., et al., J. Immunol. Meth. 289 (2004) 1-16 (2004); Geng, D., et al., J. Pharm. Biomed. Anal. 39 (2005) 364-375). In the hsFcγRI-PG assay, complexes of ADA and therapeutic mAb are detected, independent of the binding region of the therapeutic antibody. This assay is not affected by oligomeric target, and drug tolerance is much better than in the standard bridging format. The assay does not recognize Ig-subtypes other than IgG due to the FcγRI-based antibody detection. Also, the FcγRI-based assay is especially suited for therapeutic antibodies bearing the PG modification within the Fc-region. For this group of therapeutic antibodies, the hsFcγRI-PG assay represents a generic approach and can easily be applied. Also, for the hsFcγRI-PG assay, there is no need to use the therapeutic antibody (drug) in labelled form. Especially regarding the rising complexity of therapeutic antibodies (e.g. multivalent antibodies or antibody-drug conjugates), labelling can be difficult.

To summarize, the assay as reported herein offers the possibility for robust and sensitive detection of ADA against Fc-region modified therapeutic antibodies. In combination with the standard bridging assay, it can be used to characterize an immune response in more detail, for example by classifying an assay signal as IgG based.

The assay as reported herein is a generic approach and is applicable for all therapeutic antibodies, e.g. those with a Pro329Gly substitution, with prevented FcγR binding. The hsFcγRI-PG assay detects drug-ADA complexes and is based on two specific assay reagents, (i) a bi-labelled antibody against the Fc-region modification (e.g. the P329G modified therapeutic antibody) and (ii) dig-labelled hsFcγRI that specifically detects human IgG1 but no Fc-region modified Ig. In comparison to the conventional bridging assay, drug tolerance and sensitivity to late immune responses are markedly improved in the hsFcγRI-PG assay. Since non-IgG related signals are not detected by the hsFcγRI-based assay but by the conventional bridging assay, the combination of both assays allows a more detailed and robust assessment of immunogenicity, including an early differentiation between IgG and IgM responses.

The assay as reported herein is applicable for both clinical and preclinical testing. The Fc region of both human and cynomolgus monkey IgG have a high sequence-homology (Jacobsen, F. W., et al., J. Immunol. 186 (2011) 341-349), and hsFcγRI-based detection reagent has been demonstrated to recognize ADAs against therapeutic mAbs in cynomolgus monkey (Wessels, U., et al., Bioanalysis 8 (2016) 2135-2145). This fact eliminates the requirement of different assays in the analysis of animal and human samples. Moreover, several other Fc modifications than the PG-substitution have been identified that affect the affinity of therapeutic antibodies to both Fc receptors and complement and, as consequence, alter their functional profile (Moore, G. L., et al., MAbs 2 (2010) 181-189; Richards, J. O., et al., Mol. Cancer. Ther. 7 (2008) 2517-2527; Lazar, G. A., et al., Proc. Natl. Acad. Sci. USA 103 (2010) 4005-4010; Schlothauer, T., et al., Prot. Eng. Des. Sel. 29 (2016) 457-466).

The principle of the assay as reported herein can be transferred to a wide range of Fc-region mutations that allow the generation of specific antibodies.

In the examples presented here, samples were pre-incubated in assay buffer containing the therapeutic antibody, but pre-existing drug-ADA complexes can be equally detected by the same protocol without prior spiking of the drug. The detection of ADA bound in drug immune complexes appears to be particularly important because many adverse effects related to ADA formation result from the formation of ADA immune complexes (Krishna, M. and Nadler, S. G., Front. Immunol. 7 (2016) 21).

To summarize, the combination of the conventional bridging assay with the method as reported herein helps to characterize the immunogenicity profile of therapeutic mAbs with suppressed or altered Fc effector function. This approach might be of utmost importance if high levels of soluble oligomeric targets occur, and high drug concentrations are present in preclinical and clinical samples.

Thus, one aspect as reported herein is a method for the determination of the presence and/or amount of anti-drug antibodies in as sample (of a patient that had been administered the drug antibody) comprising the following steps:
  incubating the sample with an antibody specifically binding to an antibody lacking Fc effector function (by introduction of one or more substitution(s) within the Fc-region) to capture the antibody lacking Fc effector function from the sample (including free and ADA complexed antibody),
  detecting the captured antibody by incubating the captured antibody with human soluble FcγRI,
  and determining the presence and/or amount of anti-drug antibody in the sample.

In one embodiment the method comprises the following steps:
  incubating the sample with an anti-PG antibody as reported herein (specifically binding to a drug antibody that has the P329G substitution in the Fc-region and is of human IgG1 subclass) to capture the drug antibody from the sample (including free and ADA complexed drug antibody),
  detecting the captured drug antibody by incubating the captured drug antibody with human soluble FcγRI,
  and determining the presence and/or amount of anti-drug antibody in the sample by determining the presence and/or amount of bound human soluble FcγRI.

In one embodiment the anti-PG antibody is immobilized to a solid phase.

In one embodiment the anti-PG antibody comprises (a) a HVR-H1 comprising the amino acid sequence of SEQ ID NO: 20; (b) a HVR-H2 comprising the amino acid sequence of SEQ ID NO: 21; (c) a HVR-H3 comprising the amino acid sequence of SEQ ID NO: 22; (d) a HVR-L1 comprising the amino acid sequence of SEQ ID NO: 32; (e) a HVR-L2 comprising the amino acid sequence of SEQ ID NO: 34; and (f) a HVR-L3 comprising the amino acid sequence of SEQ ID NO: 35.

The antibodies as reported herein have the following sequences:

| antibody | VH | VL | HVR-H1 | HVR-H2 | HVR-H3 | HVR-L1 | HVR-L2 | HVR-L3 |
|---|---|---|---|---|---|---|---|---|
| 1.1.3 | 01 | 02 | 09 | 12 | 16 | 23 | 26 | 28 |
| 1.3.17 | 03 | 04 | 10 | 13 | 17 | 24 | 26 | 29 |
| 1.7.24 | 07 | 08 | 10 | 14 | 18 | 24 | 26 | 30 |
| 1.6.22 | 05 | 06 | 20 | 21 | 22 | 32 | 34 | 35 |

In one aspect, the invention provides isolated antibodies that specifically bind to a variant (human) Fc-region.

In certain embodiments, an anti-variant (human) Fc-region antibody as reported herein (anti-AAA antibody)
  specifically binds to an epitope on the variant (human) Fc-region comprising the amino acid residue (A)253, (A)310 and (A)435 (numbering according to Kabat EU index),
  specifically binds to a variant (human) Fc-region that has an alanine amino acid residue at positions 253, 310 and 435 (numbering according to Kabat EU index),
  does not (specifically) bind to the wild-type (human) Fc-region that has an isoleucine amino acid residue at position 253 and a histidine amino acid residue at position 310 and a histidine amino acid residue at position 435 (numbering according to Kabat EU index),
  does not (specifically) bind to the (human) Fc-region that has an isoleucine amino acid residue at position 253 and a histidine amino acid residue at position 310 and a histidine amino acid residue at position 435 and a glycine amino acid residue at position 329 and an alanine amino acid residue at position 234 and an alanine amino acid residue at position 235 (numbering according to Kabat), and
  does not (specifically) bind to the variant (human) Fc-region that has an isoleucine amino acid residue at position 253 and a histidine amino acid residue at position 310 and a histidine amino acid residue at position 435 and a proline amino acid residue at position 329 and a leucine amino acid residue at position 234 and a leucine amino acid residue at position 235 (numbering according to Kabat).

The term "does not (specifically) bind to" denotes that in an assay in which the binding is determined the results obtained is not significantly different from the result obtained with a sample not comprising the antibody in question, i.e. a blank sample or a buffer sample.

In one specific embodiment the variant (human) Fc-region is an Fc-region of the human IgG1 or IgG4 subclass with the mutations I253A, H310A and H435A (numbering according to Kabat EU index).

In one aspect, the invention provides an anti-Fc-region antibody that specifically binds to an Fc-region comprising at positions 253, 310 and 435 (numbering according to Kabat EU index) each the amino acid residue alanine comprising at least one, two, three, four, five, or six HVRs selected from (a) a HVR-H1 comprising the amino acid sequence of SEQ ID NO: 09 or 10; (b) a HVR-H2 comprising the amino acid sequence of SEQ ID NO: 12, 13 or 14; (c) a HVR-H3 comprising the amino acid sequence of SEQ ID NO: 16, 17 or 18; (d) a HVR-L1 comprising the amino acid sequence of SEQ ID NO: 23 or 24; (e) aHVR-L2 comprising the amino acid sequence of SEQ ID NO: 26; and (f) a HVR-L3 comprising the amino acid sequence of SEQ ID NO: 28, 29 or 30.

In another aspect, an antibody of the invention comprises (a) a VH domain comprising (i) a HVR-H1 comprising the amino acid sequence of SEQ ID NO: 09 or 10, (ii) a HVR-H2 comprising the amino acid sequence of SEQ ID NO: 12 or 13 or 14, and (iii) a HVR-H3 comprising an amino acid sequence selected from SEQ ID NO: 16, 17 or 18; and (b) a VL domain comprising (i) a HVR-L1 comprising the amino acid sequence of SEQ ID NO: 23 or 24, (ii) HVR-L2 comprising the amino acid sequence of SEQ ID NO: 26, and (c) HVR-L3 comprising the amino acid sequence of SEQ ID NO: 28, 29 or 30.

In another aspect, the invention provides an antibody comprising (a) a HVR-H1 comprising the amino acid sequence of SEQ ID NO: 09; (b) a HVR-H2 comprising the amino acid sequence of SEQ ID NO: 12; (c) a HVR-H3 comprising the amino acid sequence of SEQ ID NO 16; (d) a HVR-L1 comprising the amino acid sequence of SEQ ID NO: 23; (e) a HVR-L2 comprising the amino acid sequence of SEQ ID NO: 26; and (f) HVR-L3 comprising an amino acid sequence selected from SEQ ID NO: 28.

In another aspect, the invention provides an antibody comprising (a) a HVR-H1 comprising the amino acid sequence of SEQ ID NO: 10; (b) a HVR-H2 comprising the amino acid sequence of SEQ ID NO: 13; (c) a HVR-H3 comprising the amino acid sequence of SEQ ID NO 17; (d) a HVR-L1 comprising the amino acid sequence of SEQ ID NO: 24; (e) a HVR-L2 comprising the amino acid sequence of SEQ ID NO: 26; and (f) HVR-L3 comprising an amino acid sequence selected from SEQ ID NO: 29.

In another aspect, the invention provides an antibody comprising (a) a HVR-H1 comprising the amino acid sequence of SEQ ID NO: 10; (b) a HVR-H2 comprising the amino acid sequence of SEQ ID NO: 14; (c) a HVR-H3 comprising the amino acid sequence of SEQ ID NO 18; (d) a HVR-L1 comprising the amino acid sequence of SEQ ID NO: 24; (e) a HVR-L2 comprising the amino acid sequence of SEQ ID NO: 26; and (f) HVR-L3 comprising an amino acid sequence selected from SEQ ID NO: 30.

In certain embodiments, any one or more amino acids of an anti-variant (human) Fc-region antibody as provided above are substituted at the following HVR positions:
in HVR-H1 (SEQ ID NO: 11): position 5;
in HVR-H2 (SEQ ID NO: 15): positions 3, 7, 8, 11, 12;
in HVR-H3 (SEQ ID NO: 19): positions 2, 10;
in HVR-L1 (SEQ ID NO: 25): positions 3, 14;
in HVR-L2 (SEQ ID NO: 27): positions 4; and
in HVR-L3 (SEQ ID NO: 31): positions 1, 6.

In certain embodiments, the substitutions are conservative substitutions, as provided herein. In certain embodiments, any one or more of the following amino acid residues (any one either alone or in combination independently of each other) may be present in any combination:
in HVR-H1 (SEQ ID NO: 11): at position 5 a neutral hydrophilic amino acid residue selected from the group of amino acid residues consisting of S, T, N, and Q;
in HVR-H2 (SEQ ID NO: 15): at position 3 a neutral hydrophilic or acidic amino acid residue selected from the group of amino acid residues consisting of S, T, N, Q, D and E, at position 7 a neutral hydrophilic or basic amino acid residue selected from the group of amino acid residues consisting of S, T, N, Q, H, K, and R, at position 8 a neutral hydrophilic amino acid residue or a residue that influence chain orientation selected from the group of amino acid residues consisting of S, T, N, Q, G, and P, at position 11 a neutral hydrophilic or aromatic amino acid residue or a residue that influence chain orientation selected from the group of amino acid residues consisting of S, T, N, Q, G, P, W, Y, and F, at position 12 a neutral hydrophilic amino acid residue or a residue that influence chain orientation selected from the group of amino acid residues consisting of S, T, N, Q, G, and P;
in HVR-H3 (SEQ ID NO: 19): at position 2 a hydrophobic or aromatic amino acid residue selected from the group of amino acid residues consisting of M, A, V, L, I, W, Y, and F, at position 10 a neutral hydrophilic or aromatic amino acid residue selected from the group of amino acid residues consisting of S, T, N, Q, W, Y, and F;
in HVR-L1 (SEQ ID NO: 25): at position 3 a neutral hydrophilic amino acid residue selected from the group of amino acid residues consisting of S, T, N, and Q, at position 14 a neutral hydrophilic or acidic amino acid residue selected from the group of amino acid residues consisting of S, T, N, Q, D, and E;
in HVR-L2 (SEQ ID NO: 27): at position 4 an acidic or basic amino acid residue selected from the group of amino acid residues consisting of E, D, H, K, and R; and
in HVR-L3 (SEQ ID NO: 31): at position 1 a hydrophobic amino acid residue selected from the group of amino acid residues consisting of M, A, V, L, and I, at position 6 a neutral hydrophilic or acidic amino acid residue selected from the group of amino acid residues consisting of S, T, N, Q, D, and E.

All possible combinations of the above substitutions are encompassed by the consensus sequences of SEQ ID NO: 11, 15, 19, 25, 27, and 31.

In any of the above embodiments, an anti-variant (human) Fc-region antibody is humanized. In one embodiment, an anti-variant (human) Fc-region antibody comprises HVRs as in any of the above embodiments, and further comprises an acceptor human framework, e.g. a human immunoglobulin framework or a human consensus framework.

In another embodiment the humanized antibody comprises a heavy chain variable domain amino acid sequenced derived from SEQ ID NO: 01 and a light chain variable domain amino acid sequence derived from SEQ ID NO: 02, and the humanized antibody has the same binding specificity as a chimeric or murine antibody that contains as heavy chain variable domain the amino acid sequence of SEQ ID NO: 01 and as light chain variable domain the amino acid sequence of SEQ ID NO: 02.

In another embodiment the humanized antibody comprises a heavy chain variable domain amino acid sequenced derived from SEQ ID NO: 03 and a light chain variable domain amino acid sequence derived from SEQ ID NO: 04, and the humanized antibody has the same binding specificity as a chimeric or murine antibody that contains as heavy chain variable domain the amino acid sequence of SEQ ID NO: 03 and as light chain variable domain the amino acid sequence of SEQ ID NO: 04.

In another embodiment the humanized antibody comprises a heavy chain variable domain amino acid sequenced derived from SEQ ID NO: 07 and a light chain variable domain amino acid sequence derived from SEQ ID NO: 08, and the humanized antibody has the same binding specificity as a chimeric or murine antibody that contains as heavy chain variable domain the amino acid sequence of SEQ ID NO: 07 and as light chain variable domain the amino acid sequence of SEQ ID NO: 08.

In another aspect, an anti-variant (human) Fc-region antibody comprises a heavy chain variable domain (VH) sequence having at least 90%, 91%, 92%, 93%, 94%, 95%, 96%, 97%, 98%, 99%, or 100% sequence identity to the amino acid sequence of any one of SEQ ID NO: 01, 03 and 07. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-variant (human) Fc-region antibody comprising that sequence retains the ability to bind to the variant (human) Fc-region. In certain embodiments, a total of 1 to 10 amino acids have been substituted, inserted and/or deleted in any one of SEQ ID NO: 01, 03 and 07. In certain embodiments, substitutions, insertions, or deletions occur in regions outside the HVRs (i.e., in the FRs). Optionally, the anti-variant (human) Fc-region antibody comprises the VH sequence as in any one of SEQ ID NO: 01, 03 and 07, including post-translational modifications of that sequence.

In another aspect, an anti-variant (human) Fc-region antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of any one of SEQ ID NO: 02, 04 or 08. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-variant (human) Fc-region antibody comprising that sequence retains the ability to bind to the variant (human) Fc-region. In certain embodiments, a total of 1 to 10 amino acids have been substituted, inserted and/or deleted in SEQ ID NO: 02, 04 or 08. In certain embodiments, the substitutions, insertions, or deletions occur in regions outside the HVRs (i.e., in the FRs). Optionally, the anti-variant (human) Fc-region antibody comprises the VL sequence of SEQ ID NO: 02, 04 or 08, including post-translational modifications of that sequence.

In another aspect, an anti-variant (human) Fc-region antibody is provided, wherein the antibody comprises a VH as in any of the embodiments provided above, and a VL as in any of the embodiments provided above. In one embodiment, the antibody comprises (i) the VH and VL sequences in SEQ ID NO: 01 and SEQ ID NO: 02, or (ii) the VH and VL sequences in SEQ ID NO: 03 and SEQ ID NO: 04, respectively, or (iii) the VH and VL sequences in SEQ ID NO: 07 and SEQ ID NO: 08, including post-translational modifications of those sequences.

In certain embodiments, an anti-variant (human) Fc-region antibody as reported herein (anti-PG antibody)
  specifically binds to an epitope on the variant (human) Fc-region comprising the amino acid residue(s (A)234, (A)235 and) (G)329 (numbering according to Kabat EU index),
  specifically binds to a variant (human) Fc-region that has (an alanine amino acid residue at position 234 and 235, and) a glycine amino acid residue at position 329 (numbering according to Kabat EU index),
  specifically binds to a variant (human) Fc-region that has an alanine amino acid residue at position 234 and 235, a glycine amino acid residue at position 329 and an isoleucine amino acid residue at position 253 and a histidine amino acid residue at position 310 and a histidine amino acid residue at position 435 (numbering according to Kabat),
  specifically binds to a variant (human) Fc-region that has an alanine amino acid residue at position 234, 235, 253, 310 and 435, and a glycine amino acid residue at position 329 (numbering according to Kabat)
  does not (specifically) bind to the wild-type (human) Fc-region that has (a leucine amino acid residue at position 234 and 235, and) a proline amino acid residue at position 329 (numbering according to Kabat),
  does not (specifically) bind to the wild-type (human) Fc-region that has a leucine amino acid residue at position 234 and 235, and a proline amino acid residue at position 329 and an isoleucine amino acid residue at position 253 and a histidine amino acid residue at position 310 and a histidine amino acid residue at position 435 (numbering according to Kabat), and
  does not (specifically) bind to the variant (human) Fc-region that has a leucine amino acid residue at position 234 and 235, a proline amino acid residue at position 329 and an alanine amino acid residue at position 253 and an alanine amino acid residue at position 310 and an alanine amino acid residue at position 435 (numbering according to Kabat).

As the immunization performed for the generation of the anti-PG antibody was performed with human IgG1 bearing the P329G, L234A and L235A Fc-region substitutions, it was expected to obtain an antibody specifically binding to these amino acid residues. Surprisingly, the antibody obtained specifically binds to human IgG1 and Fc-region fragments only having the P239G mutation independently of the presence or absence of the L234A and L235A mutation, whereas human wt-IgG1 and human IgG1 with the mutations L234A and L235A were not bound. Thus, the anti-PG antibody as reported herein specific for the single P329G-substitution in the Fc-region of human IgG1.

In one specific embodiment the variant (human) Fc-region is an Fc-region of the human IgG1 or IgG4 subclass with the mutation P329G (numbering according to Kabat EU index).

In one aspect, the invention provides an anti-Fc-region antibody that specifically binds to an Fc-region comprising at position 329 the amino acid residue glycine (and optionally at positions 234 and 235 the amino acid residue alanine) (numbering according to Kabat EU index) comprising at least one, two, three, four, five, or six HVRs selected from (a) a HVR-H1 comprising the amino acid sequence of SEQ ID NO: 20; (b) a HVR-H2 comprising the amino acid sequence of SEQ ID NO: 21; (c) a HVR-H3 comprising the amino acid sequence of SEQ ID NO: 22; (d) a HVR-L1 comprising the amino acid sequence of SEQ ID NO: 32; (e) a HVR-L2 comprising the amino acid sequence of SEQ ID NO: 34; and (f) a HVR-L3 comprising the amino acid sequence of SEQ ID NO: 35.

In another aspect, an antibody of the invention comprises (a) a VH domain comprising (i) a HVR-H1 comprising the amino acid sequence of SEQ ID NO: 20, (ii) a HVR-H2 comprising the amino acid sequence of SEQ ID NO: 21, and (iii) a HVR-H3 comprising an amino acid sequence selected from SEQ ID NO: 22; and (b) a VL domain comprising (i) a HVR-L1 comprising the amino acid sequence of SEQ ID NO: 32, (ii) HVR-L2 comprising the amino acid sequence of SEQ ID NO: 34, and (c) HVR-L3 comprising the amino acid sequence of SEQ ID NO: 35.

In another aspect, the invention provides an antibody comprising (a) a HVR-H1 comprising the amino acid sequence of SEQ ID NO: 20; (b) a HVR-H2 comprising the amino acid sequence of SEQ ID NO: 21; (c) a HVR-H3 comprising the amino acid sequence of SEQ ID NO 22; (d) a HVR-L1 comprising the amino acid sequence of SEQ ID NO: 32; (e) a HVR-L2 comprising the amino acid sequence of SEQ ID NO: 34; and (f) HVR-L3 comprising an amino acid sequence selected from SEQ ID NO: 35.

In certain embodiments, any one or more amino acids of an anti-variant (human) Fc-region antibody as provided above are substituted at the following HVR positions:
  in HVR-L1 (SEQ ID NO: 33): position 9.

In certain embodiments, the substitutions are conservative substitutions, as provided herein. In certain embodiments, any one or more of the following amino acid residues (any one either alone or in combination independently of each other) may be present in any combination:
  in HVR-L1 (SEQ ID NO: 33): at position 9 a neutral hydrophilic amino acid residue or a residue that influence chain orientation selected from the group of amino acid residues consisting of S, T, N, Q, G and P.

All possible combinations of the above substitutions are encompassed by the consensus sequence of SEQ ID NO: 33.

In any of the above embodiments, an anti-variant (human) Fc-region antibody is humanized. In one embodiment, an anti-variant (human) Fc-region antibody comprises HVRs as in any of the above embodiments, and further comprises an acceptor human framework, e.g. a human immunoglobulin framework or a human consensus framework.

In another embodiment the humanized antibody comprises a heavy chain variable domain amino acid sequenced derived from SEQ ID NO: 05 and a light chain variable domain amino acid sequence derived from SEQ ID NO: 06, and the humanized antibody has the same binding specificity as a chimeric or murine antibody that contains as heavy chain variable domain the amino acid sequence of SEQ ID NO: 05 and as light chain variable domain the amino acid sequence of SEQ ID NO: 06.

In another aspect, an anti-variant (human) Fc-region antibody comprises a heavy chain variable domain (VH) sequence having at least 90%, 91%, 92%, 93%, 94%, 95%, 96%, 97%, 98%, 99%, or 100% sequence identity to the amino acid sequence of SEQ ID NO: 05. In certain embodiments, a VH sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-variant (human) Fc-region antibody comprising that sequence retains the ability to bind to the variant (human) Fc-region. In certain embodiments, a total of 1 to 10 amino acids have been substituted, inserted and/or deleted in SEQ ID NO: 05. In certain embodiments, substitutions, insertions, or deletions occur in regions outside the HVRs (i.e., in the FRs). Optionally, the anti-variant (human) Fc-region antibody comprises the VH sequence as in SEQ ID NO: 05, including post-translational modifications of that sequence.

In another aspect, an anti-variant (human) Fc-region antibody is provided, wherein the antibody comprises a light chain variable domain (VL) having at least 90%, 91%, 92%, 93%, 94%, 95%, 96%, 97%, 98%, 99%, or 100% sequence identity to the amino acid sequence of SEQ ID NO: 06. In certain embodiments, a VL sequence having at least 90%, 91%, 92%, 93%, 94%, 95%, 96%, 97%, 98%, or 99% identity contains substitutions (e.g., conservative substitutions), insertions, or deletions relative to the reference sequence, but an anti-variant (human) Fc-region antibody comprising that sequence retains the ability to bind to the variant (human) Fc-region. In certain embodiments, a total of 1 to 10 amino acids have been substituted, inserted and/or deleted in SEQ ID NO: 06. In certain embodiments, the substitutions, insertions, or deletions occur in regions outside the HVRs (i.e., in the FRs). Optionally, the anti-variant (human) Fc-region antibody comprises the VL sequence of SEQ ID NO: 06, including post-translational modifications of that sequence.

In another aspect, an anti-variant (human) Fc-region antibody is provided, wherein the antibody comprises a VH as in any of the embodiments provided above, and a VL as in any of the embodiments provided above. In one embodiment, the antibody comprises the VH and VL sequences in SEQ ID NO: 05 and SEQ ID NO: 06, including post-translational modifications of those sequences.

In a further aspect of the invention, an anti-variant (human) Fc-region antibody according to any of the above embodiments is a monoclonal antibody, including a chimeric, humanized or human antibody. In one embodiment, an anti-variant (human) Fc-region antibody is an antibody fragment, e.g., an Fv, Fab, Fab', scFv, diabody, or F(ab')2 fragment. In another embodiment, the antibody is a full length antibody, e.g., an intact antibody of the human IgG1 subclass or other antibody class or isotype as defined herein.

In a further aspect, an anti-variant (human) Fc-region antibody according to any of the above embodiments may incorporate any of the features, singly or in combination, as described in Sections 1-4 below:

1. Antibody Fragments

In certain embodiments, an antibody provided herein is an antibody fragment. Antibody fragments include, but are not limited to, Fab, Fab', Fab'-SH, F(ab')2, Fv, and scFv fragments, and other fragments described below. For a review of certain antibody fragments, see Hudson, P. J. et al., Nat. Med. 9 (2003) 129-134. For a review of scFv fragments, see, e.g., Plueckthun, A., In; The Pharmacology of Monoclonal Antibodies, Vol. 113, Rosenburg and Moore (eds.), Springer-Verlag, New York (1994), pp. 269-315; see also WO 93/16185; U.S. Pat. Nos. 5,571,894 and 5,587,458. For discussion of Fab and F(ab')$_2$ fragments comprising salvage receptor binding epitope residues and having increased in vivo half-life, see U.S. Pat. No. 5,869,046.

Diabodies are antibody fragments with two antigen-binding sites that may be bivalent or bispecific. See, for example, EP 0 404 097; WO 1993/01161; Hudson, P. J. et al., Nat. Med. 9 (2003) 129-134; and Holliger, P. et al., Proc. Natl. Acad. Sci. USA 90 (1993) 6444-6448. Triabodies and tetrabodies are also described in Hudson, P. J., et al., Nat. Med. 9 (20039 129-134).

Single-domain antibodies are antibody fragments comprising all or a portion of the heavy chain variable domain or all or a portion of the light chain variable domain of an antibody. In certain embodiments, a single-domain antibody is a human single-domain antibody (Domantis, Inc., Waltham, Mass.; see, e.g., U.S. Pat. No. 6,248,516).

Antibody fragments can be made by various techniques, including but not limited to proteolytic digestion of an intact antibody as well as production by recombinant host cells (e.g. *E. coli* or phage), as described herein.

2. Chimeric and Humanized Antibodies

In certain embodiments, an antibody provided herein is a chimeric antibody. Certain chimeric antibodies are described, e.g., in U.S. Pat. No. 4,816,567; and Morrison, S. L. et al., Proc. Natl. Acad. Sci. USA 81 (1984) 6851-6855). In one example, a chimeric antibody comprises a non-human variable region (e.g., a variable region derived from a mouse, rat, hamster, rabbit, or non-human primate, such as a monkey) and a human constant region. In a further example, a chimeric antibody is a "class switched" antibody in which the class or subclass has been changed from that of the parent antibody. Chimeric antibodies include antigen-binding fragments thereof.

In certain embodiments, a chimeric antibody is a humanized antibody. Typically, a non-human antibody is humanized to reduce immunogenicity to humans, while retaining the specificity and affinity of the parental non-human antibody. Generally, a humanized antibody comprises one or more variable domains in which HVRs, e.g., CDRs, (or portions thereof) are derived from a non-human antibody, and FRs (or portions thereof) are derived from human antibody sequences. A humanized antibody optionally will also comprise at least a portion of a human constant region. In some embodiments, some FR residues in a humanized antibody are substituted with corresponding residues from a non-human antibody (e.g., the antibody from which the HVR residues are derived), e.g., to restore or improve antibody specificity or affinity.

Humanized antibodies and methods of making them are reviewed, e.g., in Almagro, J. C. and Fransson, J., Front.

Biosci. 13 (2008) 1619-1633, and are further described, e.g., in Riechmann, I. et al., Nature 332 (1988) 323-329; Queen, C. et al., Proc. Natl. Acad. Sci. USA 86 (1989) 10029-10033; U.S. Pat. Nos. 5,821,337, 7,527,791, 6,982,321, and 7,087,409; Kashmiri, S. V. et al., Methods 36 (2005) 25-34 (describing specificity determining region (SDR) grafting); Padlan, E. A., Mol. Immunol. 28 (1991) 489-498 (describing "resurfacing"); Dall'Acqua, W. F. et al., Methods 36 (2005) 43-60 (describing "FR shuffling"); and Osbourn, J. et al., Methods 36 (2005) 61-68 and Klimka, A. et al., Br. J. Cancer 83 (2000) 252-260 (describing the "guided selection" approach to FR shuffling).

Human framework regions that may be used for humanization include but are not limited to: framework regions selected using the "best-fit" method (see, e.g., Sims, M. J. et al., J. Immunol. 151 (1993) 2296-2308; framework regions derived from the consensus sequence of human antibodies of a particular subgroup of light or heavy chain variable regions (see, e.g., Carter, P. et al., Proc. Natl. Acad. Sci. USA 89 (1992) 4285-4289; and Presta, L. G. et al., J. Immunol. 151 (1993) 2623-2632); human mature (somatically mutated) framework regions or human germline framework regions (see, e.g., Almagro, J. C. and Fransson, J., Front. Biosci. 13 (2008) 1619-1633); and framework regions derived from screening FR libraries (see, e.g., Baca, M. et al., J. Biol. Chem. 272 (1997) 10678-10684 and Rosok, M. J. et al., J. Biol. Chem. 271 (19969 22611-22618).

3. Multispecific Antibodies

In certain embodiments, an antibody provided herein is a multispecific antibody, e.g. a bispecific antibody. Multispecific antibodies are monoclonal antibodies that have binding specificities for at least two different sites. In certain embodiments, one of the binding specificities is for the variant (human) Fc-region and the other is for any other antigen. In certain embodiments, bispecific antibodies may bind to two different epitopes of the variant (human) Fc-region. Bispecific antibodies can be prepared as full length antibodies or antibody fragments.

Techniques for making multispecific antibodies include, but are not limited to, recombinant co-expression of two immunoglobulin heavy chain-light chain pairs having different specificities (see Milstein, C. and Cuello, A. C., Nature 305 (1983) 537-540, WO 93/08829, and Traunecker, A. et al., EMBO J. 10 (1991) 3655-3659), and "knob-in-hole" engineering (see, e.g., U.S. Pat. No. 5,731,168). Multispecific antibodies may also be made by engineering electrostatic steering effects for making antibody Fc-heterodimeric molecules (WO 2009/089004); cross-linking two or more antibodies or fragments (see, e.g., U.S. Pat. No. 4,676,980, and Brennan, M. et al., Science 229 (1985) 81-83); using leucine zippers to produce bi-specific antibodies (see, e.g., Kostelny, S. A. et al., J. Immunol. 148 (1992) 1547-1553; using "diabody" technology for making bispecific antibody fragments (see, e.g., Holliger, P. et al., Proc. Natl. Acad. Sci. USA 90 (1993) 6444-6448); and using single-chain Fv (sFv) dimers (see, e.g. Gruber, M et al., J. Immunol. 152 (1994) 5368-5374); and preparing trispecific antibodies as described, e.g., in Tutt, A. et al., J. Immunol. 147 (1991) 60-69).

Engineered antibodies with three or more functional antigen binding sites, including "Octopus antibodies," are also included herein (see, e.g. US 2006/0025576).

The antibody or fragment herein also includes a "Dual Acting Fab" or "DAF" comprising an antigen binding site that binds to the variant Fc-region as well as another, different antigen (see, US 2008/0069820, for example).

The antibody or fragment herein also includes multispecific antibodies described in WO 2009/080251, WO 2009/080252, WO 2009/080253, WO 2009/080254, WO 2010/112193, WO 2010/115589, WO 2010/136172, WO 2010/145792, and WO 2010/145793.

Several approaches for CH3-modifications in order to support heterodimerization have been described, for example in WO 96/27011, WO 98/050431, EP 1870459, WO 2007/110205, WO 2007/147901, WO 2009/089004, WO 2010/129304, WO 2011/90754, WO 2011/143545, WO 2012/058768, WO 2013/157954, WO 2013/096291, which are herein included by reference. Typically, in the approaches known in the art, the CH3 domain of the first heavy chain and the CH3 domain of the second heavy chain are both engineered in a complementary manner so that the heavy chain comprising one engineered CH3 domain can no longer homodimerize with another heavy chain of the same structure (e.g. a CH3-engineered first heavy chain can no longer homodimerize with another CH3-engineered first heavy chain; and a CH3-engineered second heavy chain can no longer homodimerize with another CH3-engineered second heavy chain). Thereby the heavy chain comprising one engineered CH3 domain is forced to heterodimerize with another heavy chain comprising the CH3 domain, which is engineered in a complementary manner. For this embodiment, the CH3 domain of the first heavy chain and the CH3 domain of the second heavy chain are engineered in a complementary manner by amino acid substitutions, such that the first heavy chain and the second heavy chain are forced to heterodimerize, whereas the first heavy chain and the second heavy chain can no longer homodimerize (e.g. for steric reasons).

The different approaches for supporting heavy chain heterodimerization known in the art, that were cited and included above, are contemplated as different alternatives used in providing a multispecific antibody as reported herein, which comprises a "non-crossed Fab region" derived from a first antibody, which specifically binds to a first antigen, and a "crossed Fab region" derived from a second antibody, which specifically binds to a second antigen, in combination with the particular amino acid substitutions described above.

The CH3 domains of the multispecific antibody as reported herein can be altered by the "knob-into-holes" technology which is described in detail with several examples in e.g. WO 96/027011, Ridgway, J. B., et al., Protein Eng. 9 (1996) 617-621; and Merchant, A. M., et al., Nat. Biotechnol. 16 (1998) 677-681. In this method the interaction surfaces of the two CH3 domains are altered to increase the heterodimerization of both heavy chains containing these two CH3 domains. Each of the two CH3 domains (of the two heavy chains) can be the "knob", while the other is the "hole". The introduction of a disulfide bridge further stabilizes the heterodimers (Merchant, A. M., et al., Nature Biotech. 16 (1998) 677-681; Atwell, S., et al., J. Mol. Biol. 270 (1997) 26-35) and increases the yield.

In one preferred embodiment the multispecific antibody as reported herein comprises a T366W mutation in the CH3 domain of the "knobs chain" and T366S, L368A, Y407V mutations in the CH3 domain of the "hole-chain" (numbering according to Kabat EU index). An additional interchain disulfide bridge between the CH3 domains can also be used (Merchant, A. M., et al., Nature Biotech. 16 (1998) 677-681) e.g. by introducing a Y349C mutation into the CH3 domain of the "knobs chain" and a E356C mutation or a S354C mutation into the CH3 domain of the "hole chain". Thus in a another preferred embodiment, the multispecific antibody as reported herein comprises the Y349C and T366W mutations in one of the two CH3 domains and the E356C, T366S, L368A and Y407V mutations in the other of the two CH3 domains or the multispecific antibody as reported herein comprises the Y349C and T366W mutations in one of the two CH3 domains and the S354C, T366S, L368A and Y407V mutations in the other of the two CH3 domains (the additional Y349C mutation in one CH3 domain and the additional E356C or S354C mutation in the other CH3 domain forming a interchain disulfide bridge) (numbering according to Kabat EU index).

In one embodiment of all aspects and embodiments as reported herein the multispecific antibody is a bispecific antibody or a trispecific antibody. In one preferred embodiment the multispecific antibody is a bispecific antibody.

In one embodiment of all aspects as reported herein, the antibody is a bivalent or trivalent antibody. In one embodiment the antibody is a bivalent antibody.

In one embodiment of all aspects as reported herein, the multispecific antibody has a constant domain structure of an IgG type antibody. In one further embodiment of all aspects as reported herein, the multispecific antibody is characterized in that said multispecific antibody is of human subclass IgG1, or of human subclass IgG1 with the mutations L234A and L235A. In one further embodiment of all aspects as reported herein, the multispecific antibody is characterized in that said multispecific antibody is of human subclass IgG2. In one further embodiment of all aspects as reported herein, the multispecific antibody is characterized in that said multispecific antibody is of human subclass IgG3. In one further embodiment of all aspects as reported herein, the multispecific antibody is characterized in that said multispecific antibody is of human subclass IgG4 or, of human subclass IgG4 with the additional mutation S228P. In one further embodiment of all aspects as reported herein, the multispecific antibody is characterized in that said multispecific antibody is of human subclass IgG1 or human subclass IgG4. In one further embodiment of all aspects as reported herein, the multispecific antibody is characterized in that said multispecific antibody is of human subclass IgG1 with the mutations L234A and L235A (numbering according to Kabat EU index). In one further embodiment of all aspects as reported herein, the multispecific antibody is characterized in that said multispecific antibody is of human subclass IgG1 with the mutations L234A, L235A and P329G (numbering according to Kabat EU index). In one further embodiment of all aspects as reported herein, the multispecific antibody is characterized in that said multispecific antibody is of human subclass IgG4 with the mutations S228P and L235E (numbering according to Kabat EU index). In one further embodiment of all aspects as reported herein, the multispecific antibody is characterized in that said multispecific antibody is of human subclass IgG4 with the mutations S228P, L235E and P329G (numbering according to Kabat EU index).

4. Antibody Variants

In certain embodiments, amino acid sequence variants of the antibodies provided herein are contemplated. For example, it may be desirable to improve the binding affinity and/or other biological properties of the antibody. Amino acid sequence variants of an antibody may be prepared by introducing appropriate modifications into the nucleotide sequence encoding the antibody, or by peptide synthesis. Such modifications include, for example, deletions from, and/or insertions into and/or substitutions of residues within the amino acid sequences of the antibody. Any combination of deletion, insertion, and substitution can be made to arrive at the final construct, provided that the final construct possesses the desired characteristics, e.g., antigen-binding.

a) Substitution, Insertion, and Deletion Variants

In certain embodiments, antibody variants having one or more amino acid substitutions are provided. Sites of interest for substitutional mutagenesis include the HVRs and FRs. Conservative substitutions are shown in Table 1 under the heading of "preferred substitutions". More substantial changes are provided in Table 1 under the heading of "exemplary substitutions," and as further described below in reference to amino acid side chain classes. Amino acid substitutions may be introduced into an antibody of interest and the products screened for a desired activity, e.g., retained/improved antigen binding, decreased immunogenicity, or improved ADCC or CDC.

TABLE 1

| Original Residue | Exemplary Substitutions | Preferred Substitutions |
| --- | --- | --- |
| Ala (A) | Val; Leu; Ile | Val |
| Arg (R) | Lys; Gln; Asn | Lys |
| Asn (N) | Gln; His; Asp, Lys; Arg | Gln |
| Asp (D) | Glu; Asn | Glu |
| Cys (C) | Ser; Ala | Ser |
| Gln (Q) | Asn; Glu | Asn |
| Glu (E) | Asp; Gln | Asp |
| Gly (G) | Ala | Ala |
| His (H) | Asn; Gln; Lys; Arg | Arg |
| Ile (I) | Leu; Val; Met; Ala; Phe; Norleucine | Leu |
| Leu (L) | Norleucine; Ile; Val; Met; Ala; Phe | Ile |
| Lys (K) | Arg; Gln; Asn | Arg |
| Met (M) | Leu; Phe; Ile | Leu |
| Phe (F) | Trp; Leu; Val; Ile; Ala; Tyr | Tyr |
| Pro (P) | Ala | Ala |
| Ser (S) | Thr | Thr |
| Thr (T) | Val; Ser | Ser |
| Trp (W) | Tyr; Phe | Tyr |
| Tyr (Y) | Trp; Phe; Thr; Ser | Phe |
| Val (V) | Ile; Leu; Met; Phe; Ala; Norleucine | Leu |

Amino acids may be grouped according to common side-chain properties:

(1) hydrophobic: Norleucine, Met, Ala, Val, Leu, Ile;
(2) neutral hydrophilic: Cys, Ser, Thr, Asn, Gln;
(3) acidic: Asp, Glu;
(4) basic: His, Lys, Arg;
(5) residues that influence chain orientation: Gly, Pro;
(6) aromatic: Trp, Tyr, Phe.

Non-conservative substitutions will entail exchanging a member of one of these classes for another class.

One type of substitutional variant involves substituting one or more hypervariable region residues of a parent antibody (e.g. a humanized or human antibody). Generally, the resulting variant(s) selected for further study will have modifications (e.g., improvements) in certain biological properties (e.g., increased affinity, reduced immunogenicity) relative to the parent antibody and/or will have substantially retained certain biological properties of the parent antibody. An exemplary substitutional variant is an affinity matured antibody, which may be conveniently generated, e.g., using phage display-based affinity maturation techniques such as those described herein. Briefly, one or more HVR residues are mutated and the variant antibodies displayed on phage and screened for a particular biological activity (e.g. binding affinity).

Alterations (e.g., substitutions) may be made in HVRs, e.g., to improve antibody affinity. Such alterations may be made in HVR "hotspots," i.e., residues encoded by codons that undergo mutation at high frequency during the somatic maturation process (see, e.g., Chowdhury, P. S., Methods Mol. Biol. 207 (2008) 179-196), and/or residues that contact antigen, with the resulting variant VH or VL being tested for binding affinity. Affinity maturation by constructing and reselecting from secondary libraries has been described, e.g., in Hoogenboom, H. R. et al. in Methods in Molecular Biology 178 (2002) 1-37. In some embodiments of affinity maturation, diversity is introduced into the variable genes chosen for maturation by any of a variety of methods (e.g., error-prone PCR, chain shuffling, or oligonucleotide-directed mutagenesis). A secondary library is then created. The library is then screened to identify any antibody variants with the desired affinity. Another method to introduce diversity involves HVR-directed approaches, in which several HVR residues (e.g., 4-6 residues at a time) are randomized. HVR residues involved in antigen binding may be specifically identified, e.g., using alanine scanning mutagenesis or modeling. CDR-H3 and CDR-L3 in particular are often targeted.

In certain embodiments, substitutions, insertions, or deletions may occur within one or more HVRs so long as such alterations do not substantially reduce the ability of the antibody to bind antigen. For example, conservative alterations (e.g., conservative substitutions as provided herein) that do not substantially reduce binding affinity may be made in HVRs. Such alterations may, for example, be outside of antigen contacting residues in the HVRs. In certain embodiments of the variant VH and VL sequences provided above, each HVR either is unaltered, or contains no more than one, two or three amino acid substitutions.

A useful method for identification of residues or regions of an antibody that may be targeted for mutagenesis is called "alanine scanning mutagenesis" as described by Cunningham, B. C. and Wells, J. A., Science 244 (1989) 1081-1085. In this method, a residue or group of target residues (e.g., charged residues such as arg, asp, his, lys, and glu) are identified and replaced by a neutral or negatively charged amino acid (e.g., alanine or polyalanine) to determine whether the interaction of the antibody with antigen is affected. Further substitutions may be introduced at the amino acid locations demonstrating functional sensitivity to the initial substitutions. Alternatively, or additionally, a crystal structure of an antigen-antibody complex to identify contact points between the antibody and antigen. Such contact residues and neighboring residues may be targeted or eliminated as candidates for substitution. Variants may be screened to determine whether they contain the desired properties.

Amino acid sequence insertions include amino- and/or carboxyl-terminal fusions ranging in length from one residue to polypeptides containing a hundred or more residues, as well as intrasequence insertions of single or multiple amino acid residues. Examples of terminal insertions include an antibody with an N-terminal methionyl residue. Other insertional variants of the antibody molecule include the fusion to the N- or C-terminus of the antibody to an enzyme (e.g. for ADEPT) or a polypeptide which increases the serum half-life of the antibody.

b) Glycosylation Variants

In certain embodiments, an antibody provided herein is altered to increase or decrease the extent to which the antibody is glycosylated. Addition or deletion of glycosylation sites to an antibody may be conveniently accomplished by altering the amino acid sequence such that one or more glycosylation sites is created or removed.

Where the antibody comprises an Fc-region, the carbohydrate attached thereto may be altered. Native antibodies produced by mammalian cells typically comprise a branched, biantennary oligosaccharide that is generally attached by an N-linkage to Asn297 of the CH2 domain of the Fc-region. See, e.g., Wright, A. and Morrison, S. L., TIBTECH 15 (1997) 26-32. The oligosaccharide may include various carbohydrates, e.g., mannose, N-acetyl glucosamine (GlcNAc), galactose, and sialic acid, as well as a fucose attached to a GlcNAc in the "stem" of the biantennary oligosaccharide structure. In some embodiments, modifications of the oligosaccharide in an antibody of the invention may be made in order to create antibody variants with certain improved properties.

In one embodiment, antibody variants are provided having a carbohydrate structure that lacks fucose attached (directly or indirectly) to an Fc-region. For example, the amount of fucose in such antibody may be from 1% to 80%, from 1% to 65%, from 5% to 65% or from 20% to 40%. The amount of fucose is determined by calculating the average amount of fucose within the sugar chain at Asn297, relative to the sum of all glycostructures attached to Asn 297 (e. g. complex, hybrid and high mannose structures) as measured by MALDI-TOF mass spectrometry, as described in WO 2008/077546, for example. Asn297 refers to the asparagine residue located at about position 297 in the Fc-region (EU numbering of Fc-region residues); however, Asn297 may also be located about ±3 amino acids upstream or downstream of position 297, i.e., between positions 294 and 300, due to minor sequence variations in antibodies. Such fucosylation variants may have improved ADCC function. See, e.g., US 2003/0157108; US 2004/0093621. Examples of publications related to "defucosylated" or "fucose-deficient" antibody variants include: US 2003/0157108; WO 2000/61739; WO 2001/29246; US 2003/0115614; US 2002/0164328; US 2004/0093621; US 2004/0132140; US 2004/0110704; US 2004/0110282; US 2004/0109865; WO 2003/085119; WO 2003/084570; WO 2005/035586; WO 2005/035778; WO 2005/053742; WO 2002/031140; Okazaki, A. et al., J. Mol. Biol. 336 (2004) 1239-1249; Yamane-Ohnuki, N. et al., Biotech. Bioeng. 87 (2004) 614-622. Examples of cell lines capable of producing defucosylated antibodies include Lec13 CHO cells deficient in protein fucosylation (Ripka, J. et al., Arch. Biochem. Biophys. 249 (1986) 533-545; US 2003/0157108; and WO 2004/056312, especially at Example 11), and knockout cell lines, such as alpha-1,6-fucosyltransferase gene, FUT8, knockout CHO cells (see, e.g., Yamane-Ohnuki, N. et al., Biotech. Bioeng. 87 (2004) 614-622; Kanda, Y. et al., Biotechnol. Bioeng. 94 (2006) 680-688; WO 2003/085107).

Antibodies variants are further provided with bisected oligosaccharides, e.g., in which a biantennary oligosaccharide attached to the Fc-region of the antibody is bisected by GlcNAc. Such antibody variants may have reduced fucosylation and/or improved ADCC function. Examples of such antibody variants are described, e.g., in WO 2003/011878; U.S. Pat. No. 6,602,684; and US 2005/0123546. Antibody variants with at least one galactose residue in the oligosaccharide attached to the Fc-region are also provided. Such antibody variants may have improved CDC function. Such antibody variants are described, e.g., in WO 1997/30087; WO 1998/58964; and WO 1999/22764.

c) Fc-Region Variants

In certain embodiments, one or more amino acid modifications may be introduced into the Fc-region of an antibody provided herein, thereby generating an Fc-region variant. The Fc-region variant may comprise a human Fc-region sequence (e.g., a human IgG1, IgG2, IgG3 or IgG4 Fc-region) comprising an amino acid modification (e.g. a substitution) at one or more amino acid positions.

In certain embodiments, the invention contemplates an antibody variant that possesses some but not all effector functions, which make it a desirable candidate for applications in which the half-life of the antibody in vivo is important yet certain effector functions (such as complement and ADCC) are unnecessary or deleterious. In vitro and/or in vivo cytotoxicity assays can be conducted to confirm the reduction/depletion of CDC and/or ADCC activities. For example, Fc receptor (FcR) binding assays can be conducted to ensure that the antibody lacks FcγR binding (hence likely lacking ADCC activity), but retains FcRn binding ability. The primary cells for mediating ADCC, NK cells, express Fc(RIII only, whereas monocytes express FcγRI, FcγRII and FcγRIII FcR expression on hematopoietic cells is summarized in Table 3 on page 464 of Ravetch, J. V. and Kinet, J. P., Annu. Rev. Immunol. 9 (1991) 457-492. Non-limiting examples of in vitro assays to assess ADCC activity of a molecule of interest is described in U.S. Pat. No. 5,500,362 (see, e.g. Hellstrom, I. et al., Proc. Natl. Acad. Sci. USA 83 (1986) 7059-7063; and Hellstrom, I. et al., Proc. Natl. Acad. Sci. USA 82 (1985) 1499-1502; U.S. Pat. No. 5,821,337 (see Bruggemann, M. et al., J. Exp. Med. 166 (1987) 1351-1361). Alternatively, non-radioactive assays methods may be employed (see, for example, ACTI™ non-radioactive cytotoxicity assay for flow cytometry (CellTechnology, Inc. Mountain View, Calif.; and CytoTox 96® non-radioactive cytotoxicity assay (Promega, Madison, Wis.). Useful effector cells for such assays include peripheral blood mononuclear cells (PBMC) and Natural Killer (NK) cells. Alternatively, or additionally, ADCC activity of the molecule of interest may be assessed in vivo, e.g., in an animal model such as that disclosed in Clynes, R. et al., Proc. Natl. Acad. Sci. USA 95 (1998) 652-656. C1q binding assays may also be carried out to confirm that the antibody is unable to bind C1q and hence lacks CDC activity (see, e.g., C1q and C3c binding ELISA in WO 2006/029879 and WO 2005/100402). To assess complement activation, a CDC assay may be performed (see, for example, Gazzano-Santoro, H. et al., J. Immunol. Methods 202 (1996) 163-171; Cragg, M. S. et al., Blood 101 (2003) 1045-1052; and Cragg, M. S. and M. J. Glennie, Blood 103 (2004) 2738-2743). FcRn binding and in vivo clearance/half-life determinations can also be performed using methods known in the art (see, e.g., Petkova, S. B. et al., Int. Immunol. 18 (2006: 1759-1769).

Antibodies with reduced effector function include those with substitution of one or more of Fc-region residues 238, 265, 269, 270, 297, 327 and 329 (U.S. Pat. No. 6,737,056). Such Fc mutants include Fc mutants with substitutions at two or more of amino acid positions 265, 269, 270, 297 and 327, including the so-called "DANA" Fc mutant with substitution of residues 265 and 297 to alanine (U.S. Pat. No. 7,332,581).

Certain antibody variants with improved or diminished binding to FcRs are described. (See, e.g., U.S. Pat. No. 6,737,056; WO 2004/056312, and Shields, R. L. et al., J. Biol. Chem. 276 (2001) 6591-6604)

In certain embodiments, an antibody variant comprises an Fc-region with one or more amino acid substitutions which improve ADCC, e.g., substitutions at positions 298, 333, and/or 334 of the Fc-region (EU numbering of residues).

In some embodiments, alterations are made in the Fc-region that result in altered (i.e., either improved or diminished) C1q binding and/or Complement Dependent Cytotoxicity (CDC), e.g., as described in U.S. Pat. No. 6,194,551, WO 99/51642, and Idusogie, E. E. et al., J. Immunol. 164 (2000) 4178-4184.

Antibodies with increased half-lives and improved binding to the neonatal Fc receptor (FcRn), which is responsible for the transfer of maternal IgGs to the fetus (Guyer, R. L. et al., J. Immunol. 117 (1976) 587-593, and Kim, J. K. et al., J. Immunol. 24 (1994) 2429-2434), are described in US 2005/0014934. Those antibodies comprise an Fc-region with one or more substitutions therein which improve binding of the Fc-region to FcRn. Such Fc variants include those with substitutions at one or more of Fc-region residues: 238, 256, 265, 272, 286, 303, 305, 307, 311, 312, 317, 340, 356, 360, 362, 376, 378, 380, 382, 413, 424 or 434, e.g., substitution of Fc-region residue 434 (U.S. Pat. No. 7,371,826).

See also Duncan, A. R. and Winter, G., Nature 322 (1988) 738-740; U.S. Pat. Nos. 5,648,260; 5,624,821; and WO 94/29351 concerning other examples of Fc-region variants.

In one embodiment of all aspects the antibody comprises (all positions according to EU index of Kabat) with the proviso that the antibody does not/cannot bind to itself i) a homodimeric Fc-region of the human IgG1 subclass optionally with the mutations P329G, L234A and L235A, or ii) a homodimeric Fc-region of the human IgG4 subclass optionally with the mutations P329G, S228P and L235E, or iii) a homodimeric Fc-region of the human IgG1 subclass optionally with the mutations P329G, L234A, L235A, I253A, H310A, and H435A, or optionally with the mutations P329G, L234A, L235A, H310A, H433A, and Y436A, or iv) a heterodimeric Fc-region whereof
  a) one Fc-region polypeptide comprises the mutation T366W, and the other Fc-region polypeptide comprises the mutations T366S, L368A and Y407V, or
  b) one Fc-region polypeptide comprises the mutations T366W and Y349C, and the other Fc-region polypeptide comprises the mutations T366S, L368A, Y407V, and S354C, or
  c) one Fc-region polypeptide comprises the mutations T366W and S354C, and the other Fc-region polypeptide comprises the mutations T366S, L368A, Y407V and Y349C, or v) a heterodimeric Fc-region of the human IgG1 subclass whereof both Fc-region polypeptides comprise the mutations P329G, L234A and L235A and
  a) one Fc-region polypeptide comprises the mutation T366W, and the other Fc-region polypeptide comprises the mutations T366S, L368A and Y407V, or
  b) one Fc-region polypeptide comprises the mutations T366W and Y349C, and the other Fc-region polypeptide comprises the mutations T366S, L368A, Y407V, and S354C, or
  c) one Fc-region polypeptide comprises the mutations T366W and S354C, and the other Fc-region polypeptide comprises the mutations T366S, L368A, Y407V and Y349C, or vi) a heterodimeric Fc-region of the human IgG4 subclass whereof both Fc-region polypeptides comprise the mutations P329G, S228P and L235E and
  a) one Fc-region polypeptide comprises the mutation T366W, and the other Fc-region polypeptide comprises the mutations T366S, L368A and Y407V, or b) one Fc-region polypeptide comprises the mutations T366W and Y349C, and the other Fc-region polypeptide comprises the mutations T366S, L368A, Y407V, and S354C, or c) one Fc-region polypeptide comprises the mutations T366W and S354C, and the other Fc-region polypeptide comprises the mutations T366S, L368A, Y407V and Y349C, or vii) a combination of one of i), ii), and iii) with one of vi), v) and vi).

In one embodiment of all aspects as reported herein, an antibody comprising a heavy chain including a CH3 domain as specified herein, comprises an additional C-terminal glycine-lysine dipeptide (G446 and K447, numbering according to Kabat EU index). In one embodiment of all aspects as reported herein, an antibody comprising a heavy chain including a CH3 domain, as specified herein, comprises an additional C-terminal glycine residue (G446, numbering according to Kabat EU index).

The antibody as reported herein is in one embodiment characterized by being of human subclass IgG1 with mutations PVA236, L234A/L235A, and/or GLPSS331 (numbering according to EU index of Kabat), or of subclass IgG4. In a further embodiment, the antibody is characterized by being of any IgG class, in one embodiment being IgG1 or IgG4, containing at least one mutation in E233, L234, L235, G236, D270, N297, E318, K320, K322, A327, A330, P331 and/or P329 (numbering according to EU index of Kabat). It is further in one embodiment that the antibody of IgG4 subclass contains the mutation S228P, or the mutations S228P and L235E (Angal, S., et al., Mol. Immunol. 30 (1993) 105-108) (numbering according to EU index of Kabat).

The C-terminus of the heavy chain of the antibody as reported herein can be a complete C-terminus ending with the amino acid residues PGK. The C-terminus of the heavy chain can be a shortened C-terminus in which one or two of the C-terminal amino acid residues have been removed. In one preferred embodiment the C-terminus of the heavy chain is a shortened C-terminus ending PG.

d) Cysteine Engineered Antibody Variants

In certain embodiments, it may be desirable to create cysteine engineered antibodies, e.g., "thioMAbs," in which one or more residues of an antibody are substituted with cysteine residues. In particular embodiments, the substituted residues occur at accessible sites of the antibody. By substituting those residues with cysteine, reactive thiol groups are thereby positioned at accessible sites of the antibody and may be used to conjugate the antibody to other moieties, such as drug moieties or linker-drug moieties, to create an immunoconjugate, as described further herein. In certain embodiments, any one or more of the following residues may be substituted with cysteine: V205 (Kabat numbering) of the light chain; A118 (EU numbering) of the heavy chain; and S400 (EU numbering) of the heavy chain Fc-region. Cysteine engineered antibodies may be generated as described, e.g., in U.S. Pat. No. 7,521,541.

e) Antibody Derivatives

In certain embodiments, an antibody provided herein may be further modified to contain additional non-proteinaceous moieties that are known in the art and readily available. The moieties suitable for derivatization of the antibody include but are not limited to water soluble polymers. Non-limiting examples of water soluble polymers include, but are not limited to, polyethylene glycol (PEG), copolymers of ethylene glycol/propylene glycol, carboxymethylcellulose, dextran, polyvinyl alcohol, polyvinyl pyrrolidone, poly-1, 3-dioxolane, poly-1,3,6-trioxane, ethylene/maleic anhydride copolymer, polyaminoacids (either homopolymers or random copolymers), and dextran or poly(n-vinyl pyrrolidone) polyethylene glycol, propropylene glycol homopolymers, prolypropylene oxide/ethylene oxide co-polymers, polyoxyethylated polyols (e.g., glycerol), polyvinyl alcohol, and mixtures thereof. Polyethylene glycol propionaldehyde may have advantages in manufacturing due to its stability in water. The polymer may be of any molecular weight, and may be branched or unbranched. The number of polymers attached to the antibody may vary, and if more than one polymer is attached, they can be the same or different molecules. In general, the number and/or type of polymers used for derivatization can be determined based on considerations including, but not limited to, the particular properties or functions of the antibody to be improved, whether the antibody derivative will be used in a therapy under defined conditions, etc.

In another embodiment, conjugates of an antibody and non-proteinaceous moiety that may be selectively heated by exposure to radiation are provided. In one embodiment, the non-proteinaceous moiety is a carbon nanotube (Kam, N. W. et al., Proc. Natl. Acad. Sci. USA 102 (2005) 11600-11605). The radiation may be of any wavelength, and includes, but is not limited to, wavelengths that do not harm ordinary cells, but which heat the non-proteinaceous moiety to a temperature at which cells proximal to the antibody-non-proteinaceous moiety are killed.

B. Recombinant Methods and Compositions

Antibodies may be produced using recombinant methods and compositions, e.g., as described in U.S. Pat. No. 4,816, 567. In one embodiment, isolated nucleic acid encoding an anti-variant (human) Fc-region antibody described herein is provided. Such nucleic acid may encode an amino acid sequence comprising the VL and/or an amino acid sequence comprising the VH of the antibody (e.g., the light and/or heavy chains of the antibody). In a further embodiment, one or more vectors (e.g., expression vectors) comprising such nucleic acid are provided. In a further embodiment, a host cell comprising such nucleic acid is provided. In one such embodiment, a host cell comprises (e.g., has been transformed with): (1) a vector comprising a nucleic acid that encodes an amino acid sequence comprising the VL of the antibody and an amino acid sequence comprising the VH of the antibody, or (2) a first vector comprising a nucleic acid that encodes an amino acid sequence comprising the VL of the antibody and a second vector comprising a nucleic acid that encodes an amino acid sequence comprising the VH of the antibody. In one embodiment, the host cell is eukaryotic, e.g. a Chinese Hamster Ovary (CHO) cell or lymphoid cell (e.g., Y0, NS0, Sp20 cell). In one embodiment, a method of making an anti-variant (human) Fc-region antibody is provided, wherein the method comprises culturing a host cell comprising a nucleic acid encoding the antibody, as provided above, under conditions suitable for expression of the antibody, and optionally recovering the antibody from the host cell (or host cell culture medium).

For recombinant production of an anti-variant (human) Fc-region antibody, nucleic acid encoding an antibody, e.g., as described above, is isolated and inserted into one or more vectors for further cloning and/or expression in a host cell. Such nucleic acid may be readily isolated and sequenced using conventional procedures (e.g., by using oligonucleotide probes that are capable of binding specifically to genes encoding the heavy and light chains of the antibody).

Suitable host cells for cloning or expression of antibody-encoding vectors include prokaryotic or eukaryotic cells described herein. For example, antibodies may be produced in bacteria, in particular when glycosylation and Fc effector function are not needed. For expression of antibody fragments and polypeptides in bacteria, see, e.g., U.S. Pat. Nos. 5,648,237, 5,789,199, and 5,840,523. (See also Charlton, K. A., In: Methods in Molecular Biology, Vol. 248, Lo, B. K. C. (ed.), Humana Press, Totowa, N.J. (2003), pp. 245-254, describing expression of antibody fragments in *E. coli*.) After expression, the antibody may be isolated from the bacterial cell paste in a soluble fraction and can be further purified.

In addition to prokaryotes, eukaryotic microbes such as filamentous fungi or yeast are suitable cloning or expression hosts for antibody-encoding vectors, including fungi and yeast strains whose glycosylation pathways have been "humanized," resulting in the production of an antibody with a partially or fully human glycosylation pattern. See Gerngross, T. U., Nat. Biotech. 22 (2004) 1409-1414; and Li, H. et al., Nat. Biotech. 24 (2006) 210-215.

Suitable host cells for the expression of glycosylated antibody are also derived from multicellular organisms (invertebrates and vertebrates). Examples of invertebrate cells include plant and insect cells. Numerous baculoviral strains have been identified which may be used in conjunction with insect cells, particularly for transfection of *Spodoptera frugiperda* cells.

Plant cell cultures can also be utilized as hosts. See, e.g., U.S. Pat. Nos. 5,959,177, 6,040,498, 6,420,548, 7,125,978, and 6,417,429 (describing PLANTIBODIES™ technology for producing antibodies in transgenic plants).

Vertebrate cells may also be used as hosts. For example, mammalian cell lines that are adapted to grow in suspension may be useful. Other examples of useful mammalian host cell lines are monkey kidney CV1 line transformed by SV40 (COS-7); human embryonic kidney line (293 or 293 cells as described, e.g., in Graham, F. L. et al., J. Gen Virol. 36 (1977) 59-74); baby hamster kidney cells (BHK); mouse sertoli cells (TM4 cells as described, e.g., in Mather, J. P., Biol. Reprod. 23 (1980) 243-252); monkey kidney cells (CV1); African green monkey kidney cells (VERO-76); human cervical carcinoma cells (HELA); canine kidney cells (MDCK; buffalo rat liver cells (BRL 3A); human lung cells (W138); human liver cells (Hep G2); mouse mammary tumor (MMT 060562); TRI cells, as described, e.g., in Mather, J. P. et al., Annals N.Y. Acad. Sci. 383 (1982) 44-68; MRC 5 cells; and FS4 cells. Other useful mammalian host cell lines include Chinese hamster ovary (CHO) cells, including DHFR$^-$ CHO cells (Urlaub, G. et al., Proc. Natl. Acad. Sci. USA 77 (1980) 4216-4220); and myeloma cell lines such as Y0, NS0 and Sp2/0. For a review of certain mammalian host cell lines suitable for antibody production, see, e.g., Yazaki, P. and Wu, A. M., Methods in Molecular Biology, Vol. 248, Lo, B. K. C. (ed.), Humana Press, Totowa, N.J. (2004), pp. 255-268.

C. Assays

Anti-variant (human) Fc-region antibodies provided herein may be used in various assays known in the art.

The antibodies as reported herein are especially useful if a therapeutic antibody comprising the respective mutations in the Fc-region or an anti-drug antibody against such a therapeutic antibody has to be detected, e.g. in a sample.

In one embodiment the therapeutic antibody comprises
  i) the mutations P329G or P329G, L234A and L235A, and/or
  ii) the mutations I253A, H310A and H435A.

In one embodiment the antibody comprising the respective mutations is an antibody comprising
  i) the mutations P329G or P329G, L234A and L235A, and/or
  ii) the mutations I253A, H310A and H435A.

One aspect as reported herein is the use of an antibody as reported herein in an (antigen bridging) immunoassay either as capture antibody or as tracer antibody for the determination of a therapeutic antibody comprising the respective mutations in the Fc-region (i.e. an antibody comprising the respective mutations in the Fc-region) (in a sample). The respective other reagent required for detection or for capture can be any of the antigen of the therapeutic antibody, a second antibody that specifically binds to the therapeutic antibody or a moiety conjugated thereto but not interfering with the binding of the antibody used (i.e. both antibodies can bind to the therapeutic antibody simultaneously), an anti-idiotypic antibody for the therapeutic antibody, or a human Fcgamma receptor I or an Fc-region-binding fragment thereof, respectively, which has been derivatized, immobilized or labelled accordingly.

This assay is applicable to any non-human serum if the antibody as reported herein is used as a tracer antibody. In one embodiment the use is for the determination in a serum sample of a non-human experimental animal.

This assay is applicable to any serum (including human serum) if the antibody as reported herein is used as a capture antibody.

Such an assay has a lower limit of quantification of below 100 pg/ml, e.g. of 40-80 pg/ml in 10% cynomolgus serum (assay concentration).

One aspect as reported herein is the use of one or more antibodies as reported herein in an antigen bridging immunoassay as capture antibody and as tracer antibody for the determination of a therapeutic antibody comprising the respective mutations in the Fc-region (in a sample).

This assay is applicable to any serum (including human serum). In one preferred embodiment two different antibodies as reported herein are used as capture antibody and as tracer antibody.

One aspect as reported herein is the use of an antibody as reported herein in an antigen bridging immunoassay as calibration standard.

One aspect as reported herein is the use of an antibody as reported herein in an immunoassay for the determination of an anti-drug antibody against a therapeutic antibody whereby the therapeutic antibody comprises the respective mutations in the Fc-region (in a sample).

This assay is applicable to any serum (including human serum) if the antibody as reported herein is used as a capture antibody.

One aspect as reported herein is a method for detecting a therapeutic antibody of human IgG1 or IgG4 subclass comprising the respective mutations in the Fc-region (in a sample) comprising the steps of
  a) optionally providing a sample to be analyzed,
  b) incubating the sample with an antibody as reported herein or an Fc-region binding fragment thereof,
  c) optionally incubating the sample with a reagent for the selective detection of the therapeutic antibody, and
  d) correlating the complex formed in (b) or (c) to the presence of the therapeutic antibody and thereby detecting the therapeutic antibody.

In one embodiment the antibody as reported herein is used as a capture antibody. The capturing antibody is in one embodiment immobilized to a solid surface. This solid surface is in one embodiment (the wall or the bottom of) a well of a multi-well plate. Thus, in one embodiment the method comprises the following steps:

a) incubating the sample with an antibody as reported herein or an Fc-region binding fragment thereof immobilized on a solid surface to form an immobilized complex comprising the therapeutic antibody,
b) optionally washing the solid surface (to remove unbound substances),
c) incubating the immobilized complex with a detection reagent selectively binding to the therapeutic antibody, and thereby detecting the therapeutic antibody in a sample.

In one embodiment the antibody as reported herein is used as a tracer antibody. For capturing a suitable capture reagent is in one embodiment immobilized to a solid surface. This solid surface is in one embodiment (the wall or the bottom of) a well of a multi-well plate. Thus, in one embodiment the method comprises the following steps:

a) incubating the sample with a capture reagent immobilized on a solid surface to form an immobilized complex comprising the therapeutic antibody,
b) optionally washing the solid surface (to remove unbound substances),
c) incubating the immobilized complex with an antibody as reported herein or an Fc-region binding fragment thereof conjugated to a detectable label to form a further complex,
d) incubating the complex formed in c) with a detection reagent selectively binding to the detectable label, and thereby detecting the therapeutic antibody in a sample.

One aspect as reported herein is a method for determining a therapeutic antibody of human IgG1 or IgG4 subclass comprising the respective mutations in the Fc-region in a sample using an antigen bridging immunoassay comprising a capture antibody and a tracer antibody, characterized in that the capture antibody and the tracer antibody are both independently selected from antibodies as reported herein or an Fc-region binding fragment thereof.

In one embodiment the sample is obtained from an experimental animal selected from the members of the families of marmosets and tamarins, old world monkeys, dwarf and mouse lemurs, gibbons and lesser apes, true lemurs, as well as crossings thereof or from a human. In one embodiment the sample is obtained from a rhesus-monkey, or a marmoset monkey, or a baboon monkey, or a cynomolgus monkey, or a human. In one embodiment the experimental animal is a macaca or macaque monkey. In one embodiment the sample is obtained from a cynomolgus monkey or a rhesus-monkey or a human.

One aspect as reported herein is the use of an antibody as reported herein or an Fc-region binding fragment thereof which is specifically binding to a therapeutic antibody of human IgG1 or IgG4 subclass comprising the respective mutations in the Fc-region for determining the concentration of total, active, ADA-bound, or antigen-bound therapeutic antibody (in a sample).

One aspect as reported herein is an antibody composition comprising a mixture of the antibodies as reported herein and/or Fc-region binding fragments thereof.

One aspect as reported herein is the use of an antibody composition as reported herein in a method as reported herein.

In one embodiment the immunoassay is a sandwich immunoassay. In another embodiment the conjugation of the antibody to its conjugation partner is performed by chemically binding via N-terminal and/or ε-amino groups (lysine), ε-amino groups of different lysines, carboxy-, sulfhydryl-, hydroxyl- and/or phenolic functional groups of the amino acid backbone of the antibody and/or sugar alcohol groups of the carbohydrate structure of the antibody. In one embodiment the capture antibody is immobilized via a specific binding pair. In one embodiment the capture antibody is conjugated to biotin and immobilization is performed via immobilized avidin or streptavidin. In one embodiment the tracer antibody is conjugated to the detectable label via a specific binding pair. In one embodiment the tracer antibody is conjugated to digoxygenin and linking to the detectable label is performed via an antibody against digoxygenin. In one embodiment the therapeutic antibody is a human or a humanized antibody. In one embodiment the human or humanized antibody is a monoclonal antibody. In one embodiment the total therapeutic antibody is detected, in another embodiment the active therapeutic antibody is detected, and in a further embodiment the therapeutic antibody is detected which is bound to its antigen.

One aspect as reported herein is a method of detecting a therapeutic antibody (in a sample) comprising the steps of:

a) incubating a sample with an antibody as reported herein or an Fc-region binding fragment thereof that has been immobilized on a solid surface to form a complex,
b) incubating said sample with a reagent appropriate for the selective detection of total, active or antigen-bound therapeutic antibody, and
c) correlating the complex formed in (b) to the concentration of said therapeutic antibody (in the sample), and thereby detecting the therapeutic antibody.

One aspect as reported herein is an anti-drug antibody immunoassay for the determination of the presence of an anti-drug antibody against an Fc-receptor binding suppressed human or humanized drug antibody (i.e. an antibody comprising the respective mutations in the Fc-region) (in a sample) comprising the following steps in the following order:

a) incubating a sample comprising mammalian blood serum with an antibody as reported herein or an Fc-region binding fragment thereof that has been immobilized on a solid surface to form a complex,
b) incubating the complex of a) with full length human Fcgamma receptor I or an Fc-region binding fragment thereof so that a complex between the anti-drug antibody against the Fc-receptor binding suppressed human or humanized drug antibody present in the sample and the human Fcgamma receptor I or the Fc-region binding fragment thereof forms, whereby the full length human Fcgamma receptor I or the Fc-region binding fragment thereof is conjugated to a detectable label, and
c) determining the complex formed in the previous step by the detectable label.

One aspect as reported herein is an anti-drug antibody immunoassay for the determination of the presence of an anti-drug antibody against an Fc-receptor binding suppressed human or humanized drug antibody (i.e. an antibody comprising the respective mutations in the Fc-region) (in a sample) comprising the following steps in the following order:

a) incubating a sample comprising mammalian blood serum with full length human Fcgamma receptor I or an Fc-region binding fragment thereof that has been immobilized on a solid surface to form a complex,
b) incubating the complex of a) with an antibody as reported herein or an Fc-region binding fragment thereof so that a complex between the anti-drug antibody against the Fc-receptor binding suppressed human or humanized drug antibody present in the sample and the antibody as reported herein forms, whereby the antibody as reported herein is conjugated to a detectable label, c) determining the complex formed in the previous step by the detectable label.

One aspect as reported herein is an anti-drug antibody immunoassay for the determination of the presence of an anti-drug antibody against an Fc-receptor binding suppressed human or humanized drug antibody (i.e. an antibody comprising the respective mutations in the Fc-region) (in a sample) comprising the following steps in the following order:

a) incubating a solid phase on which the Fc-receptor binding suppressed human or humanized drug antibody has been immobilized with a sample comprising mammalian blood serum (so that a solid-phase-bound drug antibody-anti-drug antibody complex is formed), b) incubating the solid phase (to which the drug antibody-anti-drug antibody complex formed in step a) is bound) with an antibody as reported herein or an Fc-region binding fragment thereof conjugated to a detectable label, and c) determining the formation of a solid-phase-bound complex in step b) by determining the presence of the detectable label and thereby determining the presence of an anti-drug antibody against an Fc-receptor binding suppressed human or humanized drug antibody in the sample.

One aspect as reported herein is an anti-drug antibody immunoassay for the determination of the presence of an anti-drug antibody against an Fc-receptor binding suppressed human or humanized drug antibody in a sample comprising the following steps in the following order:

a) incubating a solid phase on which the FAB of an Fc-receptor binding suppressed human or humanized drug antibody has been immobilized with a sample comprising mammalian blood serum (so that a solid-phase-bound FAB-anti-drug antibody complex is formed), b) incubating the solid phase (to which the FAB-anti-drug antibody complex formed in step a) is bound) with an antibody as reported herein or an Fc-region binding fragment thereof conjugated to a detectable label, and c) determining the formation of a solid-phase bound complex in step b) by determining the presence of the detectable label and thereby determining the presence of an anti-drug antibody against an Fc-receptor binding suppressed human.

One aspect as reported herein is an anti-drug antibody immunoassay for the determination of the presence of an anti-drug antibody against an Fc-receptor binding suppressed human or humanized drug antibody (i.e. an antibody comprising the respective mutations in the Fc-region) (in a sample) comprising the following steps in the following order:

a) adding (excess) drug antibody to the sample (to transfer (any) anti-drug antibody present in the sample in a drug-antibody-anti-drug antibody complex), wherein the sample comprises mammalian blood serum, b) incubating a solid phase on which the antigen to which the Fc-receptor binding suppressed human or humanized drug antibody specifically binds has been immobilized with the sample obtained in step a) (so that a solid-phase-bound antigen-drug antibody-anti-drug antibody complex is formed), c) incubating the solid phase (to which the antigen-drug antibody-anti-drug antibody complex formed in step b) is bound) with an antibody as reported herein or an Fc-region binding fragment thereof conjugated to a detectable label, and d) determining the formation of a solid-phase-bound complex in step c) by determining the presence of the detectable label and thereby determining the presence of an anti-drug antibody against an Fc-receptor binding suppressed human or humanized drug antibody in the sample.

One aspect as reported herein is an anti-drug antibody immunoassay for the determination of the presence of an anti-drug antibody against an Fc-receptor binding suppressed human or humanized drug antibody (i.e. an antibody comprising the respective mutations in the Fc-region) (in a sample) comprising the following steps in the following order:

a) adding (excess) drug antibody to the sample (to transfer (any) anti-drug antibody present in the sample in a drug-antibody-anti-drug antibody complex), wherein the sample comprises mammalian blood serum, b) incubating a solid phase on which an antibody as reported herein or an Fc-region binding fragment thereof has been immobilized with the sample obtained in step a) (so that a solid-phase-bound Fc-region antibody-drug antibody-anti-drug antibody complex is formed), c) incubating the solid phase (to which the Fc-region antibody-drug antibody-anti-drug antibody complex formed in step b) is bound) with the antigen of the drug antibody, whereby the antigen is conjugated to a detectable label, and d) determining the formation of a solid-phase-bound complex in step c) by determining the presence of the detectable label and thereby determining the presence of an anti-drug antibody against an Fc-receptor binding suppressed human or humanized drug antibody in the sample.

One aspect as reported herein is an anti-drug antibody immunoassay for the determination of the presence of an anti-drug antibody against an Fc-receptor binding suppressed human or humanized drug antibody (i.e. an antibody comprising the respective mutations in the Fc-region) (in a sample) comprising the following steps in the following order:

a) adding (excess) drug antibody to the sample (to transfer (any) anti-drug antibody present in the sample in a drug-antibody-anti-drug antibody complex), wherein the sample comprises mammalian blood serum, b) incubating a solid phase on which an anti-drug antibody against the drug antibody has been immobilized with the sample obtained in step a) (so that a solid-phase-bound anti-drug antibody-drug antibody-anti-drug antibody complex is formed), c) incubating the solid phase (to which the anti-drug antibody-drug antibody-anti-drug antibody complex formed in step b) is bound) with an antibody as reported herein or an Fc-region binding fragment thereof conjugated to a detectable label, and d) determining the formation of a solid-phase-bound complex in step c) by determining the presence of the detectable label and thereby determining the presence of an anti-drug antibody against an Fc-receptor binding suppressed human or humanized drug antibody in the sample.

One aspect as reported herein is a method for the determination of the presence of an anti-drug antibody against an Fc-receptor binding suppressed human or humanized drug antibody (i.e. an antibody comprising the respective mutations in the Fc-region) (in a sample) comprising the following steps in the following order:

incubating a sample comprising mammalian blood serum with an antibody as reported herein or an Fc-region binding fragment thereof so that a complex between the anti-drug antibody against the Fc-receptor binding suppressed human or humanized drug antibody present in the sample and the antibody as reported herein or the Fc-region binding fragment thereof forms, whereby the antibody as reported herein or the Fc-region binding fragment thereof is conjugated to a detectable label, and determining the complex formed in the previous step by the detectable label.

One aspect as reported herein is the use of an antibody as reported herein in an (antigen bridging) immunoassay either as capture antibody for the determination of a therapeutic antibody comprising the respective mutations in the Fc-region (i.e. an antibody comprising the respective mutations in the Fc-region) complexed with an anti-drug antibody (in a sample). The respective other reagent required for detection of the complex can be a human Fcgamma receptor I or an Fc-region-binding fragment thereof, respectively, which has been derivatized, immobilized or labelled accordingly.

This assay is applicable to any human and non-human serum if an antibody as reported herein is used as a capture antibody. In one embodiment the use is for the determination in a serum sample of a non-human experimental animal.

Such an assay has a lower limit of quantification of below 100 pg/ml, e.g. of 40-80 pg/ml in 10% cynomolgus serum (assay concentration).

One aspect as reported herein is the use of an antibody as reported herein or an Fc-region binding fragment thereof for the determination of the presence or amount of an anti-drug antibody against an Fc-receptor binding suppressed human or humanized drug antibody (i.e. an antibody comprising the respective mutations in the Fc-region) (in a sample) comprising mammalian blood serum.

In one embodiment of all aspects as reported herein each incubating step is followed by the following step:

washing the solid phase to remove unbound compounds.

In one embodiment of all aspects as reported herein the assay is for the determination of the presence and the amount of an anti-drug antibody against an Fc-receptor binding suppressed human or humanized drug antibody (i.e. an antibody comprising the respective mutations in the Fc-region) (in a sample) and comprises as final steps:

determining the formation of a solid-phase-bound complex in the previous step by determining the presence of the detectable label and determining the amount of an anti-drug antibody against an Fc-receptor binding suppressed human or humanized drug antibody in the sample by correlating the amount of the determined label with the amount of the anti-drug antibody using a standard curve.

In one embodiment of all aspects as reported herein the Fc-receptor binding suppressed human or humanized drug antibody is of the human IgG1 or IgG4 subclass.

In one embodiment of all aspects as reported herein the Fc-receptor binding suppressed human or humanized drug antibody is of the human IgG1 subclass and has the mutations L234A, L235A and P329G in both Fc-region polypeptides, or the Fc-receptor binding suppressed human or humanized drug antibody is of the human IgG4 subclass and has the mutations S228P, L235E and P329G in both Fc-region polypeptides, or the Fc-receptor binding suppressed human or humanized drug antibody is of the human IgG1 subclass and has the mutations I253A, H310A, H435A and P329G in both Fc-region polypeptides, or the Fc-receptor binding suppressed human or humanized drug antibody is of the human IgG4 subclass and has the mutations I253A, H310A, H435A and P329G in both Fc-region polypeptides (numbering according to the EU numbering system according to Kabat).

In one embodiment of all aspects the Fc-receptor binding suppressed human or humanized drug antibody is a bispecific antibody, or a trispecific antibody, or a tetraspecific antibody, or a pentaspecific antibody, or a hexaspecific antibody. In one embodiment the Fc-receptor binding suppressed human or humanized drug antibody is a bispecific antibody.

In one embodiment of all aspects as reported herein the mammalian blood serum is human blood serum or cynomolgus blood serum or mouse blood serum.

In one embodiment of all aspects as reported herein the mammalian blood serum has been obtained from a mammal to which the Fc-receptor binding suppressed human or humanized drug antibody had been administered. In one embodiment the sample is obtained at least 2 days after the first administration of the antibody to the mammal.

In one embodiment of all aspects as reported herein the anti-drug antibody against an effector function suppressed human or humanized drug antibody is of the IgG class.

In one embodiment of all aspects as reported herein the presence and/or amount of the label is determined using an enzyme linked color reaction, surface plasmon resonance, electrochemiluminescense, or radioimmunoassay.

In one embodiment of all aspects as reported herein the immunoassay and/or the method and/or the use is an in vitro immunoassay and/or an in vitro method and/or an in vitro use.

In one embodiment of all aspects as reported herein the solid phase is conjugated to a first member of a binding pair and the compound to be immobilized on the solid phase is conjugated to the second member of a binding pair.

Such a binding pair (first member/second member) is in one embodiment selected from streptavidin or avidin/biotin, antibody/antigen (see, for example, Hermanson, G. T., et al., Bioconjugate Techniques, Academic Press (1996)), lectin/polysaccharide, steroid/steroid binding protein, hormone/hormone receptor, enzyme/substrate, IgG/Protein A and/or G, etc.

In one embodiment the second binding partner is bound (immobilized) via a specific binding pair. Such a binding pair (first component/second component) is in one embodiment selected from streptavidin or avidin/biotin, antibody/antigen (see, for example, Hermanson, G. T., et al., Bioconjugate Techniques, Academic Press (1996)), lectin/polysaccharide, steroid/steroid binding protein, hormone/hormone receptor, enzyme/substrate, IgG/Protein A and/or G, etc. In one embodiment the second binding partner is conjugated to biotin and immobilization is performed via immobilized avidin or streptavidin.

In one preferred embodiment the first member of a binding pair is streptavidin and the second member of a binding pair is biotin.

In one embodiment the solid phase is conjugated to streptavidin and the compound to be immobilized on the solid phase is biotinylated.

In one embodiment the solid phase is a streptavidin coated paramagnetic bead or a streptavidin coated sepharose bead or a streptavidin coated well of a multi-well-plate.

In one embodiment the compound to be conjugated to the solid phase is a mixture comprising at least two compounds that differ in the site at which they are conjugated to biotin and thereby thereafter immobilized on the solid phase.

In one embodiment the compound to be immobilized on the solid phase is conjugated to the second member of the binding pair by chemically binding via N-terminal and/or ε-amino groups (lysine), ε-amino groups of different lysins, carboxy-, sulfhydryl-, hydroxyl- and/or phenolic functional groups of the amino acid backbone of the polypeptide and/or sugar alcohol groups of the carbohydrate structure of the polypeptide.

Such conjugation via different amino groups can be performed by acylation of a part of the ε-amino groups with chemical protecting agents, e.g. by citraconylation, in a first step. In a second step conjugation is performed via the remaining amino groups. Subsequently citraconylation is removed and the binding partner is immobilized on the solid phase via remaining free amino groups, i.e. the binding partner obtained is immobilized on the solid phase via amino groups that have not been protected by citraconylation. Suitable chemical protecting agents form bonds at unprotected side chain amines and are less stable than and different from those bonds at the N-terminus. Many such chemical protecting agents are known (see for example EP 0 651 761). In one embodiment the chemical protecting agents include cyclic dicarboxylic acid anhydrides like maleic or citraconylic acid anhydride.

One aspect as reported herein is a method for the (immunological) determination of the amount of a multispecific binder (in a sample) comprising the step of:
  determining the amount of a complex formed between
  i) an anti-idiotypic antibody that specifically binds to a first binding specificity of the multispecific binder, and
  ii) the multispecific binder
  by incubating the complex with an antibody as reported herein or an Fc-region binding fragment thereof, and
  thereby determining the amount of the multispecific binder in the sample.

In one embodiment the anti-idiotypic antibody that specifically binds to a first binding specificity of the multispecific binder is conjugated to a solid phase.

In one embodiment the antibody as reported herein of the Fc-region binding fragment thereof is conjugated to a detectable label.

In one embodiment the sample comprises (human) serum or (human) plasma, and/or is a cell lysate, and/or comprises one or more antigens of the multispecific binder. In one embodiment the sample is (human) serum or (human) plasma.

In one embodiment the multispecific binder is selected from an antibody, a fusion polypeptide comprising an antibody or antibody fragment and a non-antibody polypeptide, a fusion polypeptide comprising an antibody or antibody fragment and a soluble receptor, or a fusion polypeptide comprising an antibody or antibody fragment and a peptidic binding molecule.

In one embodiment the multispecific binder is an antibody. In one embodiment the antibody is a bispecific antibody, or a trispecific antibody, or a tetraspecific antibody, or a pentaspecific antibody, or a hexaspecific antibody. In one embodiment the antibody is a bispecific antibody.

In one embodiment the binding specificity is a binding site or a pair of an antibody heavy chain variable domain and an antibody light chain variable domain.

In one embodiment the anti-idiotypic antibody that specifically binds to a first binding specificity of the multispecific binder is biotinylated and the solid phase is streptavidin coated. In one embodiment the solid phase is a streptavidin coated paramagnetic bead or a streptavidin coated sepharose bead.

In one embodiment the antibody as reported herein or an Fc-region binding fragment thereof is digoxigenylated.

In one embodiment the method comprises the step of
  determining the amount of a complex formed between
  i) an antibody as reported herein or an Fc-region binding fragment thereof,
  ii) the multispecific binder, and
  iii) an anti-idiotypic antibody that specifically binds to a binding specificity of the multispecific binder and that comprises a detectable label,
  by determination the detectable label in the formed complex.

In one embodiment the conjugation of an anti-idiotypic antibody to its conjugation partner is performed by chemically binding via N-terminal and/or ε-amino groups (lysine), ε-amino groups of different lysins, carboxy-, sulfhydryl-, hydroxyl- and/or phenolic functional groups of the amino acid backbone of the drug antibody and/or sugar alcohol groups of the carbohydrate structure of the drug antibody.

In one embodiment the anti-idiotypic antibody is a mixture comprising the anti-idiotypic antibody conjugated via at least two different amino groups to the solid phase. Such coupling via different amino groups can be performed by acylation of a part of the ε-amino groups with chemical protecting agents, e.g. by citraconylation, in a first step. In a second step conjugation is performed via the remaining amino groups. Subsequently citraconylation is removed and the antibody is conjugated to the solid phase via remaining free amino groups, i.e. the antibody obtained is conjugated to the solid phase via amino groups that have not been protected by citraconylation. Suitable chemical protecting agents form bonds at unprotected side chain amines and are less stable than and different from those bonds at the N-terminus. Many such chemical protecting agents are known (see for example EP 0 651 761). In one embodiment the chemical protecting agents include cyclic dicarboxylic acid anhydrides like maleic or citraconylic acid anhydride.

In one embodiment the antibody as reported herein or an Fc-region binding fragment thereof is conjugated (immobilized) via a specific binding pair. Such a binding pair (first component/second component) is in one embodiment selected from streptavidin or avidin/biotin, antibody/antigen (see, for example, Hermanson, G. T., et al., Bioconjugate Techniques, Academic Press (1996), lectin/polysaccharide, steroid/steroid binding protein, hormone/hormone receptor, enzyme/substrate, IgG/Protein A and/or G, etc. In one embodiment the anti-idiotypic antibody is conjugated to biotin and immobilization is performed via immobilized avidin or streptavidin.

One aspect as reported herein is an in vitro method for the determination of the presence and/or the amount of an (first) antigen of a bispecific antibody (in a sample), whereby the antigen to be detected can be specifically bound by a first binding specificity of the bispecific antibody, and whereby the antigen is complexed to the bispecific antibody (antigen-bispecific antibody-complex), comprising the step of:
  incubating a sample comprising the antigen and the bispecific antibody with an antibody as reported herein or an Fc-region binding fragment thereof, which is conjugated to a solid phase.

In one embodiment the method comprises the steps of:
  incubating a sample comprising the antigen and the bispecific antibody with an antibody as reported herein or an Fc-region binding fragment thereof, which is conjugated to a solid phase, and detecting the complex of antigen-bispecific antibody-anti-Fc-region antibody and thereby determining the presence and/or the amount of the antigen of a bispecific antibody.

In one embodiment the method comprises the steps of:

incubating a sample comprising the antigen and the bispecific antibody with an antibody as reported herein or an Fc-region binding fragment thereof, which is conjugated to a solid phase, and incubating the complex formed in the first step with an antibody that specifically binds to the antigen at an epitope different from the epitope bound by the bispecific antibody and thereby determining the presence and/or the amount of the antigen of a bispecific antibody in a sample.

In one embodiment the method is for the determination of the presence and/or the amount of an antigen of a bispecific antibody, which is complexed to the bispecific antibody.

In one embodiment the method comprises the following steps:

providing a sample comprising the antigen and the bispecific antibody, wherein at least 90% of the antigen is complexed by the bispecific antibody, incubating a sample comprising the antigen and the bispecific antibody with an antibody as reported herein or an Fc-region binding fragment thereof, which is conjugated to a solid phase, and incubating the complex formed in the first step with an antibody that specifically binds to the antigen at an epitope different from the epitope bound by the bispecific antibody and thereby determining the presence and/or the amount of the antigen of a bispecific antibody in a sample.

In one embodiment the method comprises the following steps:

incubating a sample comprising the antigen and the bispecific antibody with an amount of the bispecific antibody to provide a sample wherein at least 90% of the antigen is complexed by the bispecific antibody, incubating the sample comprising the antigen complexed by the bispecific antibody with an antibody as reported herein or an Fc-region binding fragment thereof, which is conjugated to a solid phase, and incubating the complex formed in the previous step with an antibody that specifically binds to the antigen at an epitope different from the epitope bound by the bispecific antibody and thereby determining the presence and/or the amount of the antigen of a bispecific antibody in a sample.

In one embodiment at least 95% of the antigen is complexed by the bispecific antibody. In one embodiment at least 98% of the antigen is complexed by the bispecific antibody.

One aspect as reported herein is an in vitro method for the determination of the amount of antibody-bound (first) antigen of a bispecific antibody (in a sample), whereby the antigen can be specifically bound by a first binding specificity of the bispecific antibody, comprising the steps of:

incubating a first aliquot of the sample comprising the antigen and the bispecific antibody with an amount of the bispecific antibody to provide a sample wherein at least 90% of the antigen is complexed by the bispecific antibody, incubating the sample comprising the antigen complexed by the bispecific antibody with an antibody as reported herein or an Fc-region binding fragment thereof, which is conjugated to a solid phase, and incubating the complex formed in the previous step with an antibody that specifically binds to the antigen at an epitope different from the epitope bound by the bispecific antibody and thereby determining the presence and/or the amount of the antigen of a bispecific antibody in a sample and thereby determining the total amount of the antigen present in the sample, incubating a second aliquot of the sample comprising the antigen and the bispecific antibody with an antibody as reported herein or an Fc-region binding fragment thereof, which is conjugated to a solid phase, and incubating the formed complex with an antibody that specifically binds to the antigen at an epitope different from the epitope bound by the bispecific antibody and thereby determining the amount of the free antigen of a bispecific antibody present in the sample, and determining the amount of antibody-bound antigen of a bispecific antibody by the difference between the total amount of the antigen present in the sample and the amount of free antigen present in the sample.

One aspect as reported herein is a method for the in vitro determination of the presence and/or amount of a binding partner (antigen, target, analyte), which can be specifically bound by a first binding specificity of a multispecific binder, wherein the fraction of binding partner bound to the multispecific binder present in a sample is depleted prior to the detection of the binding partner by incubating the sample with an antibody as reported herein or an Fc-region binding fragment thereof.

In one embodiment the binding partner to be detected is non-complexed binding partner or free binding partner.

One aspect as reported herein is an in vitro method for the determination of the presence and/or the amount of a (first) binding partner of a multispecific binder, whereby the binding partner can be specifically bound by a first binding specificity of the multispecific binder, comprising the step of:

incubating a sample comprising (first) binding partner and multispecific binder with an antibody as reported herein or an Fc-region binding fragment thereof.

In one embodiment the method comprises the steps of:

incubating a sample comprising (first) binding partner and multispecific binder with an antibody as reported herein or an Fc-region binding fragment thereof, and determining the amount of the (free first) binding partner in the multispecific binder-depleted sample.

In one embodiment the method comprises the step of:

incubating a sample comprising (first) binding partner and multispecific binder with an antibody as reported herein or an Fc-region binding fragment thereof, depleting the Fc-region antibody-multispecific binder-complex from the sample prior to the determination of the presence or the amount of free binding partner, and determining the amount of the (free first) binding partner in the multispecific binder-depleted sample.

By the incubation with an antibody as reported herein or an Fc-region binding fragment thereof the multispecific binder is removed/depleted from the sample. Concomitantly also (first) binding partner-multispecific binder-complexes are removed from the sample.

In one embodiment the multispecific binder is selected from an antibody, a fusion polypeptide comprising an antibody or antibody fragment and non-antibody polypeptide, a fusion polypeptide comprising an antibody or antibody fragment and a soluble receptor, or a fusion polypeptide comprising an antibody or antibody fragment and a peptidic binding molecule.

In one embodiment the multispecific binder is an antibody. In one embodiment the antibody is a bispecific antibody, or a trispecific antibody, or a tetraspecific antibody, or a pentaspecific antibody, or a hexaspecific antibody. In one embodiment the antibody is a bispecific antibody.

In one embodiment the binding specificity is a binding site or a pair of an antibody heavy chain variable domain and an antibody light chain variable domain.

In one embodiment the antibody as reported herein or an Fc-region binding fragment thereof is conjugated to a solid phase.

In one embodiment the second binding partner is biotinylated and the solid phase is streptavidin coated. In one embodiment the solid phase is a streptavidin coated paramagnetic bead or a streptavidin coated sepharose bead.

One aspect as reported herein is a method for the immunological determination of the presence and/or amount of a binding partner of a multispecific binder in a sample using an immunoassay, wherein the multispecific binder is depleted from the sample prior to the determination of the binding partner by incubation with an antibody as reported herein or an Fc-region binding fragment thereof and removal of the formed complexes.

In one embodiment of all respective aspects as reported herein the binding partner is the free binding partner, i.e. binding partner that is not bound or complexed by the multispecific binder.

In one embodiment the antibody as reported herein or an Fc-region binding fragment thereof is a biotinylated second binding partner and is conjugated to a solid phase via streptavidin.

In one embodiment of the methods as reported herein the antibody as reported herein or the Fc-region binding fragment thereof is a mixture comprising at least two antibodies as reported herein and/or an Fc-region binding fragments thereof that differ in the site at which they are conjugated to the solid phase. In one embodiment the site is the amino acid position of the amino acid sequence of the antibody as reported herein or an Fc-region binding fragment thereof.

In one embodiment the first binding partner is a polypeptide.

In one embodiment the second binding partner is a polypeptide.

In one embodiment the conjugation is performed by chemically binding via N-terminal and/or ε-amino groups (lysine), ε-amino groups of different lysins, carboxy-, sulfhydryl-, hydroxyl- and/or phenolic functional groups of the amino acid backbone of the polypeptide and/or sugar alcohol groups of the carbohydrate structure of the polypeptide.

Coupling via different amino groups can be performed by acylation of a part of the ε-amino groups with chemical protecting agents, e.g. by citraconylation, in a first step. In a second step conjugation is performed via the remaining amino groups. Subsequently citraconylation is removed and the binding partner is conjugated to the solid phase via remaining free amino groups, i.e. the binding partner obtained is conjugated to the solid phase via amino groups that have not been protected by citraconylation. Suitable chemical protecting agents form bonds at unprotected side chain amines and are less stable than and different from those bonds at the N-terminus. Many such chemical protecting agents are known (see for example EP 0 651 761). In one embodiment the chemical protecting agents include cyclic dicarboxylic acid anhydrides like maleic or citraconylic acid anhydride.

In one embodiment the antibody as reported herein or an Fc-region binding fragment thereof is conjugated to the solid phase by passive adsorption. Passive adsorption is, e. g., described by Butler, J. E., in "Solid Phases in Immunoassay" (1996) 205-225 and Diamandis, E. P., and Christopoulos, T. K. (Editors), in "Immunoassay" (1996) Academic Press (San Diego).

In one embodiment the antibody as reported herein or an Fc-region binding fragment thereof is conjugated (immobilized) via a specific binding pair. Such a binding pair (first component/second component) is in one embodiment selected from streptavidin or avidin/biotin, antibody/antigen (see, for example, Hermanson, G. T., et al., Bioconjugate Techniques, Academic Press (1996)), lectin/polysaccharide, steroid/steroid binding protein, hormone/hormone receptor, enzyme/substrate, IgG/Protein A and/or G, etc. In one embodiment the second binding partner is conjugated to biotin and immobilization is performed via immobilized avidin or streptavidin.

In one embodiment the method comprises the following steps:
  incubating a multispecific antibody-depleted sample with a capture antibody that specifically binds to the (first) antigen to form a capture antibody-(first) antigen complex, and
  correlating the formed capture antibody-(first) antigen complex to the amount of the (first) antigen in the sample.

In one embodiment the method comprises the following steps:
  incubating a multispecific antibody-depleted sample with a capture antibody that specifically binds to the (first) antigen to form a capture antibody-(first) antigen complex,
  incubating the capture antibody-(first) antigen complex with a tracer antibody, whereby the capture antibody and the tracer antibody bind to non-overlapping epitope on the (first) antigen, and
  correlating the formed capture antibody-(first) antigen-tracer antibody complex to the amount of the antigen in the sample.

In one embodiment the method comprises the following steps:
  incubating a multispecific antibody-depleted sample with a capture antibody that specifically binds to the (first) antigen to form a capture antibody-(first) antigen complex,
  incubating the capture antibody-(first) antigen complex with a tracer antibody, whereby the capture antibody and the tracer antibody bind to non-overlapping epitope on the (first) antigen,
  incubating the capture antibody-(first) antigen-tracer antibody complex with a detection antibody comprising a detectable label, whereby the detection antibody specifically binds to the tracer antibody at an epitope outside the variable domains of the tracer antibody, and
  correlating the formed capture antibody-(first) antigen-tracer antibody complex to the amount of the (first) antigen in the sample.

In one embodiment the multispecific antibody is a bispecific antibody that has a first binding specificity that specifically binds to a first antigen or first epitope on an antigen and that has a second binding specificity that specifically binds to a second antigen or to a second epitope on the antigen.

In one embodiment the first antigen and the second antigen are the same antigen and the first binding specificity binds to a first epitope on the antigen and the second binding specificity binds to a second epitope on the antigen whereby the second epitope is a non-overlapping epitope to the first epitope and the binding of the first binding specificity does not interfere with the binding of the second binding specificity.

In one embodiment the method comprises the step of:
depleting the formed complex from the sample prior to the determination of the presence or the amount of the (first) antigen.

One aspect as reported herein is an in vitro method for the determination of the presence and/or the amount of an (first) antigen of a multispecific antibody (in a sample), whereby the antigen to be detected can be specifically bound by a first binding specificity of the multispecific antibody, comprising the step of:
incubating a sample comprising the (first) antigen with a complex of bispecific antibody and an antibody as reported herein or an Fc-region binding fragment thereof.

In one embodiment the second antigen is a labeled second antigen. In one embodiment the antibody as reported herein or an Fc-region binding fragment thereof is immobilized via a specific binding pair to a solid phase. In one embodiment the specific binding pair is biotin and streptavidin.

In one embodiment the method comprises as second step:
incubating the complex formed in the first step with an antibody that specifically binds to the first antigen at an epitope different from the epitope bound by the bispecific antibody.

One aspect as reported herein is an in vitro method for the determination of the presence and/or the amount of an (first) antigen of a bispecific antibody (in a sample) complexed to the bispecific antibody (first antigen-bispecific antibody-complex), whereby the antigen to be detected can be specifically bound by a first binding specificity of the bispecific antibody, comprising the step of:
incubating a sample comprising the (first) antigen and the bispecific antibody with an antibody as reported herein or an Fc-region binding fragment thereof, which is conjugated to a solid phase.

In one embodiment the method comprises as second step:
incubating the complex formed in the first step with an antibody that specifically binds to the first antigen at an epitope different from the epitope bound by the bispecific antibody and thereby determining the amount of a (first) antigen of a bispecific antibody complexed to the bispecific antibody (first antigen-bispecific antibody-complex) in a sample.

In one embodiment the method comprises the step of:
depleting the formed complex from the sample prior to the determination of the presence or the amount of the (first) antigen.

One aspect as reported herein is an in vitro method for the determination of the presence and/or amount of an antigen of a multispecific antibody (in a sample), whereby the antigen to be detected can be specifically bound by a first binding specificity of the multispecific antibody, comprising the step of:
incubating a sample comprising the multispecific antibody, multispecific antibody bound antigen and free antigen with an antibody as reported herein or an Fc-region binding fragment thereof.

In one embodiment the method comprises the steps of:
incubating a sample comprising antigen and multispecific antibody with an antibody as reported herein or an Fc-region binding fragment thereof, and
determining the amount of the antigen in the multispecific antibody-depleted sample.

In one embodiment the method comprises the step of:
incubating a sample comprising antigen and multispecific antibody an antibody as reported herein or an Fc-region binding fragment thereof,
depleting the anti-Fc-region antibody-multispecific antibody-complex from the sample prior to the determination of the presence or the amount of free antigen, and
determining the amount of the antigen in the multispecific antibody-depleted sample.

In one embodiment the sample comprises multispecific antibody, free antigen and multispecific antibody-antigen complexes and the detection is of free antigen of the multispecific antibody.

In one embodiment the antibody as reported herein or an Fc-region binding fragment thereof is conjugated to a paramagnetic bead.

In one embodiment the antibody as reported herein or an Fc-region binding fragment thereof is conjugated to a solid phase.

In one embodiment the antibody as reported herein or an Fc-region binding fragment thereof is biotinylated and the solid phase is streptavidin coated. In one embodiment the solid phase is a streptavidin coated paramagnetic bead or a streptavidin coated sepharose bead.

In one embodiment the binding specificity is a binding site. In one embodiment the binding site is a pair of an antibody heavy chain variable domain and an antibody light chain variable domain.

In one embodiment the method comprises the following steps:
incubating a sample comprising the multispecific antibody, multispecific antibody-bound antigen and free antigen with an antibody as reported herein or an Fc-region binding fragment thereof, and
removing the anti-Fc-region antibody-multispecific antibody complex from the sample.

In one embodiment the anti-Fc-region antibody-multispecific antibody complex is a mixture of anti-Fc-region antibody-multispecific antibody complex and anti-Fc-region antibody-multispecific antibody-antigen complex.

In one embodiment the method comprises the following steps:
incubating a sample comprising antigen and multispecific antibody with an antibody as reported herein or an Fc-region binding fragment thereof to form an anti-Fc-region antibody-multispecific antibody complex,
removing the anti-Fc-region antibody-multispecific antibody complex from the sample, and
determining the amount of the antigen in the multispecific-antibody depleted sample.

In one embodiment the determining of the amount of the antigen comprises the following steps:
incubating a multispecific antibody-depleted sample with a capture antibody that specifically binds to the antigen to form a capture antibody-antigen complex, and
correlating the formed capture antibody-antigen complex to the amount of the antigen in the sample.

In one embodiment the determining of the amount of the antigen comprises the following steps:

incubating a multispecific antibody-depleted sample with a capture antibody that specifically binds to the antigen to form a capture antibody-antigen complex, incubating the capture antibody-antigen complex with a tracer antibody, whereby the capture antibody and the tracer antibody bind to non-overlapping epitope on the antigen, and correlating the formed capture antibody-antigen-tracer antibody complex to the amount of the antigen in the sample.

In one embodiment the determining of the amount of the antigen comprises the following steps:

incubating a multispecific antibody-depleted sample with a capture antibody that specifically binds to the antigen to form a capture antibody-antigen complex, incubating the capture antibody-antigen complex with a tracer antibody, whereby the capture antibody and the tracer antibody bind to non-overlapping epitope on the antigen, incubating the capture antibody-antigen-tracer antibody complex with a detection antibody comprising a detectable label, whereby the detection antibody specifically binds to the tracer antibody at an epitope outside the variable domains of the tracer antibody, and correlating the formed capture antibody-antigen-tracer antibody complex to the amount of the antigen in the sample.

In one embodiment the multispecific antibody is a bispecific antibody that has a first binding specificity that specifically binds to a first antigen or first epitope on an antigen and that has a second binding specificity that specifically binds to a second antigen or to a second epitope on the antigen.

One aspect as reported herein is the use of an antibody as reported herein or an Fc-region binding fragment thereof for the depletion of antigen bound to the second binding specificity of the multispecific antibody from a sample.

The term "therapeutic antibody" denotes an antibody which is tested or has been tested in clinical studies for approval as human therapeutic and which can be administered to an individual for the treatment of a disease. In one embodiment the therapeutic antibody is a monoclonal antibody. In a further embodiment the therapeutic antibody is obtained from a great ape or an animal transformed with a human antibody locus, or is a human monoclonal antibody, or is a humanized monoclonal antibody. In one embodiment the therapeutic antibody is a human monoclonal antibody. In one embodiment the therapeutic antibody is a humanized monoclonal antibody. Therapeutic antibodies are being used widely for the treatment of various diseases such as oncological diseases (e.g. hematological and solid malignancies including non-Hodgkin's lymphoma, breast cancer, and colorectal cancer), immunological diseases, central nervous diseases, vascular diseases, or infectious diseases. Such antibodies are, for instance, antibodies against CD19, CD20, CD22, HLA-DR, CD33, CD52, EGFR, G250, GD3, HER2, PSMA, CD56, VEGF, VEGF2, CEA, Levis Y antigen, IL-6 receptor (IL6R), or IGF-1 receptor (IGF1R).

The term "epitope" denotes a protein determinant capable of specifically binding to an antibody. Epitopes usually consist of chemically active surface groupings of molecules such as amino acids or sugar side chains and usually epitopes have specific three dimensional structural characteristics, as well as specific charge characteristics. Conformational and non-conformational epitopes are distinguished in that the binding to the former but not the latter is lost in the presence of denaturing solvents. The principles of different immunoassays are described, for example, by Hage, D. S. (Anal. Chem. 71 (1999) 294R-304R). Lu, B., et al. (Analyst 121 (1996) 29R-32R) report the orientated immobilization of antibodies for the use in immunoassays. Avidin-biotin-mediated immunoassays are reported, for example, by Wilchek, M., and Bayer, E. A., in Methods Enzymol. 184 (1990) 467-469.

Polypeptides and monoclonal antibodies and their constant domains contain a number of reactive amino acid side chains for conjugating to a member of a binding pair, such as a polypeptide/protein, a polymer (e.g. PEG, cellulose or polystyrol), or an enzyme. Chemical reactive groups of amino acids are, for example, amino groups (lysins, alpha-amino groups), thiol groups (cystins, cysteines, and methionins), carboxylic acid groups (aspartic acids, glutamic acids), and sugar-alcoholic groups. Such methods are e.g. described by Aslam M., and Dent, A., in "Bioconjugation", MacMillan Ref. Ltd. 1999, pages 50-100.

One of the most common reactive groups of polypeptides and antibodies is the aliphatic ε-amine of the amino acid lysine. In general, nearly all polypeptides and antibodies contain abundant lysine. Lysine amines are reasonably good nucleophiles above pH 8.0 (pKa=9.18) and therefore react easily and cleanly with a variety of reagents to form stable bonds. Amine-reactive reagents react primarily with lysins and the α-amino groups of proteins. Reactive esters, particularly N-hydroxy-succinimide (NHS) esters, are among the most commonly employed reagents for modification of amine groups. The optimum pH for reaction in an aqueous environment is pH 8.0 to 9.0. Isothiocyanates are amine-modification reagents and form thiourea bonds with proteins. They react with protein amines in aqueous solution (optimally at pH 9.0 to 9.5). Aldehydes react under mild aqueous conditions with aliphatic and aromatic amines, hydrazines, and hydrazides to form an imine intermediate (Schiff s base). A Schiff s base can be selectively reduced with mild or strong reducing agents (such as sodium borohydride or sodium cyanoborohydride) to derive a stable alkyl amine bond. Other reagents that have been used to modify amines are acid anhydrides. For example, diethylenetriaminepentaacetic anhydride (DTPA) is a bifunctional chelating agent that contains two amine-reactive anhydride groups. It can react with N-terminal and ε-amine groups of amino acids to form amide linkages. The anhydride rings open to create multivalent, metal-chelating arms able to bind tightly to metals in a coordination complex.

Another common reactive group in polypeptides and antibodies is the thiol residue from the sulfur-containing amino acid cystine and its reduction product cysteine (or half cystine). Cysteine contains a free thiol group, which is more nucleophilic than amines and is generally the most reactive functional group in a protein. Thiols are generally reactive at neutral pH, and therefore can be coupled to other molecules selectively in the presence of amines. Since free sulfhydryl groups are relatively reactive, proteins with these groups often exist with them in their oxidized form as disulfide groups or disulfide bonds. In such proteins, reduction of the disulfide bonds with a reagent such as dithiothreitol (DTT) is required to generate the reactive free thiol. Thiol-reactive reagents are those that will couple to thiol groups on polypeptides, forming thioether-coupled products. These reagents react rapidly at slight acidic to neutral pH and therefore can be reacted selectively in the presence of amine groups. The literature reports the use of several thiolating crosslinking reagents such as Traut's reagent (2-iminothiolane), succinimidyl (acetylthio) acetate (SATA), and sulfosuccinimidyl 6-[3-(2-pyridyldithio) propionamido]

hexanoate (Sulfo-LC-SPDP) to provide efficient ways of introducing multiple sulfhydryl groups via reactive amino groups. Haloacetyl derivatives, e.g. iodoacetamides, form thioether bonds and are also reagents for thiol modification. Further useful reagents are maleimides. The reaction of maleimides with thiol-reactive reagents is essentially the same as with iodoacetamides. Maleimides react rapidly at slight acidic to neutral pH.

Another common reactive group in polypeptides and antibodies are carboxylic acids. Polypeptides and antibodies contain carboxylic acid groups at the C-terminal position and within the side chains of aspartic acid and glutamic acid. The relatively low reactivity of carboxylic acids in water usually makes it difficult to use these groups to selectively modify polypeptides and antibodies. When this is done, the carboxylic acid group is usually converted to a reactive ester by the use of a water-soluble carbodiimide and reacted with a nucleophilic reagent such as an amine, hydrazide, or hydrazine. The amine-containing reagent should be weakly basic in order to react selectively with the activated carboxylic acid in the presence of the more highly basic ε-amines of lysine to form a stable amide bond. Protein crosslinking can occur when the pH is raised above 8.0.

Sodium periodate can be used to oxidize the alcohol part of a sugar within a carbohydrate moiety attached to an antibody to an aldehyde. Each aldehyde group can be reacted with an amine, hydrazide, or hydrazine as described for carboxylic acids. Since the carbohydrate moiety is predominantly found on the crystallizable fragment (Fc) region of an antibody, conjugation can be achieved through site-directed modification of the carbohydrate away from the antigen-binding site. A Schiffs base intermediate is formed, which can be reduced to an alkyl amine through the reduction of the intermediate with sodium cyanoborohydride (mild and selective) or sodium borohydride (strong) water-soluble reducing agents.

The term "sample" includes, but is not limited to, any quantity of a substance from a living thing or formerly living thing. Such living things include, but are not limited to, humans, mice, monkeys, rats, rabbits, and other animals. In one embedment the sample is obtained from a monkey, especially a cynomolgus monkey, or a rabbit, or a mouse, or rat, or a human. Such substances include, but are not limited to, in one embodiment whole blood or serum from an individual, which are the most widely used sources of sample in clinical routine.

The term "solid phase" denotes a non-fluid substance, and includes particles (including microparticles and beads) made from materials such as polymer, metal (paramagnetic, ferromagnetic particles), glass, and ceramic; gel substances such as silica, alumina, and polymer gels; capillaries, which may be made of polymer, metal, glass, and/or ceramic; zeolites and other porous substances; electrodes; microtiter plates; solid strips; and cuvettes, tubes or other spectrometer sample containers. A solid phase component is distinguished from inert solid surfaces in that a "solid phase" contains at least one moiety on its surface, which is intended to interact with a substance in a sample. A solid phase may be a stationary component, such as a tube, strip, cuvette or microtiter plate, or may be non-stationary components, such as beads and microparticles. A variety of microparticles that allow either non-covalent or covalent attachment of proteins and other substances may be used. Such particles include polymer particles such as polystyrene and poly (methylmethacrylate); gold particles such as gold nanoparticles and gold colloids; and ceramic particles such as silica, glass, and metal oxide particles. See for example Martin, C. R., et al., Analytical Chemistry-News & Features, 70 (1998) 322A-327A, or Butler, J. E., Methods 22 (2000) 4-23.

From chromogens (fluorescent or luminescent groups and dyes), enzymes, NMR-active groups, metal particles, or haptens, such as digoxygenin, the detectable label is selected in one embodiment. The detectable label can also be a photoactivatable crosslinking group, e.g. an azido or an azirine group. Metal chelates which can be detected by electrochemiluminescense are also in one embodiment signal-emitting groups, with particular preference being given to ruthenium chelates, e.g. a ruthenium (bispyridyl)$_3^{2+}$ chelate. Suitable ruthenium labeling groups are described, for example, in EP 0 580 979, WO 90/05301, WO 90/11511, and WO 92/14138.

Some compounds as used in the immunoassay and method as reported herein are conjugated to a member of a binding pair. The conjugation is in one embodiment performed by chemical binding via N-terminal and/or ε-amino groups (lysine), ε-amino groups of different lysins, carboxy-, sulfhydryl-, hydroxyl- and/or phenolic functional groups of the amino acid backbone of the compound and/or sugar alcohol groups of the carbohydrate structure of the compound. The conjugated compound is in one embodiment a mixture of at least two compounds conjugated to a member of a binding pair, wherein the at least two compounds in the mixture differ in the site at which they are conjugated to the member of the binding pair. For example, the mixture may comprise a conjugation via an amino acid of the amino acid backbone and a conjugation via a sugar alcohol group of a carbohydrate. Also, for example, the mixture may comprise compounds conjugated to the member of a binding pair via different amino acid residues of the amino acid backbone. The expression "different amino acid residue" denotes either two different kinds of amino acids, such as e.g. lysine and aspartic acid, or tyrosine and glutamic acid, or two amino acid residues of the amino acid backbone differing in their position in the amino acid sequence of the compound. In the latter case the amino acid can be of the same kind or of different kind. The expression "differ in the site" denotes a difference either in the kind of site, e.g. amino acid or sugar alcohol group, or in the number of the amino acid of the amino acid backbone, e.g. at which the compound is conjugated to the member of the binding pair.

The term "anti-idiotypic antibody" denotes an antibody, which specifically binds to a binding specificity such as a binding site of a parent antibody, i.e. which is directed e.g. against an antigen binding site of a parent antibody. In one embodiment the anti-idiotypic antibody specifically binds to one or more of the CDRs of the parent antibody. In one embodiment the parent antibody is a therapeutic antibody. In one embodiment the parent antibody is a multispecific antibody. In one embodiment the parent antibody is a bispecific antibody.

The term "total" therapeutic antibody refers to any antibody detected irrespective of whether the antibody is active (i.e., still reactive with its antigen), inactive, and/or antigen-bound.

The term "active" therapeutic antibody relates to the therapeutic antibody present in an experimental animal that still is capable of binding its antigen. Such antibodies, e.g., have not bound its antigen or any other molecule at its antigen binding site.

The term "antigen-bound" therapeutic antibody is used to indicate the therapeutic antibody as present in the circulation of an experimental animal that is bound to its antigen.

Total, active or antigen-bound therapeutic antibody as defined above can be directly detected in a method according to the present invention.

In addition, it is also possible to indirectly assess any "inactive" therapeutic antibody. Such inactive therapeutic antibody may, e.g., be a therapeutic antibody bound to its antigen, the therapeutic antibody bound to a cross-reactive antigen, or the therapeutic antibody blocked by an auto antibody against the therapeutic antibody. As the skilled artisan will appreciate, it is possible by aid of the present disclosure to assess the fraction of inactive antibody. In case the total antibody amounts to more than the sum of active antibody and antigen-bound antibody, an additional fraction of antibody comprising the inactive antibody not bound to its corresponding antigen will be present.

In one preferred embodiment total therapeutic antibody is detected in a sandwich type immunoassay, wherein an antibody as reported herein or an Fc-region binding fragment thereof is used at both sides of such sandwich assay. The antibody used at one side of such sandwich is bound or capable of binding to a solid phase (often referred to as capture antibody), whereas the antibody at the other side of such sandwich is labeled in such a manner that direct or indirect detection is facilitated (so-called detection antibody). The amount of detection antibody bound in such sandwich assay procedure is directly correlated to the amount of therapeutic antibody in the sample investigated.

In the art (e.g. US 2003/0068664) assay systems are known, which allow for the detection of active therapeutic antibodies. Such systems require the binding of the antigen to a solid phase, binding of the therapeutic antibody to this bound antigen and detection of the therapeutic antibody bound via the antigen to the solid phase.

Detection of active therapeutic antibody in a sample may be achieved by convenient state of the art procedures. However, the detection of total therapeutic antibody or of the fraction of therapeutic antibody bound to its antigen is rather complicated and requires quite different assay set-ups and especially requires tailor-made reagents for each of the different assays. With the antibodies as reported herein it is possible to assess the fraction of active therapeutic antibody, total therapeutic antibody, or antigen-bound therapeutic antibody in test systems which are analogues to each other. By its very nature this kind of comparative assessment of total, active, or antigen-bound therapeutic antibody should have big advantages once quantitative comparisons are made in between these various fractions of therapeutic antibody.

A sandwich type assay format can (also) be set up to detect the active therapeutic antibody. In one preferred embodiment an antibody as reported herein or an Fc-region binding fragment thereof is used as a capture antibody and the detection side of such sandwich assay either makes use of the antigen in a labeled form or after binding of the antigen makes use of a second antibody not binding to or competing with the epitope recognized by the therapeutic antibody, wherein said second antibody is specifically detectable and/or is labeled in such a manner that direct or indirect detection is facilitated.

The antigen-bound therapeutic antibody preferably is detected in a sandwich type assay format again preferably using an antibody as reported herein or an Fc-region binding fragment thereof as a capture reagent. In the detection preferably a second antibody is used binding to the antigen at an epitope which does not compete with the epitope of the therapeutic antibody. Said second antibody preferably is labeled in such a manner that direct or indirect detection is facilitated.

For direct detection the labeling group can be selected from any known detectable marker groups, such as dyes, luminescent labeling groups such as chemiluminescent groups, e.g. acridinium esters or dioxetanes, or fluorescent dyes, e.g. fluorescein, coumarin, rhodamine, oxazine, resorufin, cyanine and derivatives thereof. Other examples of labeling groups are luminescent metal complexes, such as ruthenium or europium complexes, enzymes, e.g. as used for ELISA or for CEDIA (Cloned Enzyme Donor Immunoassay, e.g. EP-A-0 061 888), and radioisotopes.

Indirect detection systems comprise, for example, that the detection reagent, e.g., the detection antibody is labeled with a first partner of a bioaffine binding pair. Examples of suitable binding pairs are hapten or antigen/antibody, biotin or biotin analogues such as aminobiotin, iminobiotin or desthiobiotin/avidin or streptavidin, sugar/lectin, nucleic acid or nucleic acid analogue/complementary nucleic acid, and receptor/ligand, e.g., steroid hormone receptor/steroid hormone. Preferred first binding pair members comprise hapten, antigen and hormone. Especially preferred are haptens like digoxin and biotin and analogues thereof. The second partner of such binding pair, e.g. an antibody, streptavidin, etc., usually is labeled to allow for direct detection, e.g., by the labels as mentioned above.

Immunoassays are well known to the skilled artisan. Methods for carrying out such assays as well as practical applications and procedures are summarized in related textbooks. Examples of related textbooks are Tijssen, P., Preparation of enzyme-antibody or other enzyme-macromolecule conjugates (in: "Practice and theory of enzyme immunoassays" (1990), pp. 221-278, Eds. R. H. Burdon and v. P. H. Knippenberg, Elsevier, Amsterdam) and various volumes of "Methods in Enzymology" (Eds. S. P. Colowick, N. O. Caplan, Academic Press), dealing with immunological detection methods, especially volumes 70, 73, 74, 84, 92 and 121.

In all the above immunological detection methods reagent conditions are chosen which allow for binding of the reagents employed, e.g. for binding of an antibody to its corresponding antigen. The skilled artisan refers to the result of such binding event by using the term complex. The complex formed in an assay method according to the present invention is correlated by state of the art procedures to the corresponding concentration of said therapeutic antibody. Depending on the detection reagent employed this correlating step will result in the concentration of total, active or antigen-bound therapeutic antibody.

As the skilled artisan will appreciate the methods according to the present invention will not only reveal the concentrations of total, antigen-bound, active or even inactive therapeutic antibody. Due to the preferred use of one and the same reagent, an antibody as reported herein or an Fc-region binding fragment thereof, in the different assays the values obtained can be easily compared to each other and even ratios thereof assessed. In a further preferred embodiment the present invention relates to the ratio of active to total therapeutic antibody. This ratio may well serve as an indicator for the efficacy of a therapeutic antibody.

D. Methods and Compositions for Diagnostics and Detection

In certain embodiments, any of the anti-variant (human) Fc-region antibodies provided herein is useful for detecting the presence of a therapeutic antibody comprising a variant Fc-region with the mutation(s) P329G(/L234A/L235A) or the mutations I253A/H310A/H435A in a biological sample. The term "detecting" as used herein encompasses quantitative or qualitative detection. In certain embodiments, a biological sample comprises a biological fluid, such as e.g. blood serum.

In one embodiment, an anti-variant (human) Fc-region antibody for use in a method of diagnosis or detection is provided. In a further aspect, a method of detecting the presence of a therapeutic antibody comprising a variant Fc-region with the mutation P329G or the mutations I253A/H310A/H435A in a biological sample is provided. In certain embodiments, the method comprises contacting the biological sample with an anti-variant (human) Fc-region antibody as described herein under conditions permissive for binding of the anti-variant (human) Fc-region antibody to a therapeutic antibody comprising a variant Fc-region with the mutation P329G or the mutations I253A/H310A/H435A, and detecting whether a complex is formed between the anti-variant (human) Fc-region antibody and the therapeutic antibody comprising a variant Fc-region with the mutation P329G or the mutations I253A/H310A/H435A. Such method may be an in vitro or in vivo method.

In certain embodiments, labeled anti-variant (human) Fc-region antibodies are provided. Labels include, but are not limited to, labels or moieties that are detected directly (such as fluorescent, chromophoric, electron-dense, chemiluminescent, and radioactive labels), as well as moieties, such as enzymes or ligands, that are detected indirectly, e.g., through an enzymatic reaction or molecular interaction. Exemplary labels include, but are not limited to, the radioisotopes $^{32}P$, $^{14}C$, $^{125}I$, $^{3}H$, and $^{131}I$, fluorophores such as rare earth chelates or fluorescein and its derivatives, rhodamine and its derivatives, dansyl, umbelliferone, luciferases, e.g., firefly luciferase and bacterial luciferase (U.S. Pat. No. 4,737,456), luciferin, 2,3-dihydrophthalazinediones, horseradish peroxidase (HRP), alkaline phosphatase, β-galactosidase, glucoamylase, lysozyme, saccharide oxidases, e.g., glucose oxidase, galactose oxidase, and glucose-6-phosphate dehydrogenase, heterocyclic oxidases such as uricase and xanthine oxidase, coupled with an enzyme that employs hydrogen peroxide to oxidize a dye precursor such as HRP, lactoperoxidase, or microperoxidase, biotin/avidin, spin labels, bacteriophage labels, stable free radicals, and the like.

III. Examples

The following are examples of methods and compositions of the invention. It is understood that various other embodiments may be practiced, given the general description provided above.

Example 1

Materials and Methods

General information regarding the nucleotide sequences of human immunoglobulins light and heavy chains is given in: Kabat, E. A., et al., Sequences of Proteins of Immunological Interest, 5th ed., Public Health Service, National Institutes of Health, Bethesda, Md. (1991). Amino acids of antibody chains are numbered and referred to according to numbering according to Kabat (Kabat, E. A., et al., Sequences of Proteins of Immunological Interest, 5th ed., Public Health Service, National Institutes of Health, Bethesda, Md. (1991)).

Recombinant DNA Techniques

Standard methods can be used to manipulate DNA as described in Sambrook, J. et al., Molecular Cloning: A laboratory manual; Cold Spring Harbor Laboratory Press, Cold Spring Harbor, N.Y., 1989. The molecular biological reagents are used according to the manufacturer's instructions.

Gene Synthesis

Desired gene segments can be prepared from oligonucleotides made by chemical synthesis. The long gene segments, which can be flanked by singular restriction endonuclease cleavage sites, can be assembled by annealing and ligating oligonucleotides including PCR amplification and subsequently cloned via the indicated restriction sites. The DNA sequences of the subcloned gene fragments can be confirmed by DNA sequencing.

DNA Sequence Determination

DNA sequences can be determined by double strand sequencing.

DNA and Protein Sequence Analysis and Sequence Data Management

The GCG's (Genetics Computer Group, Madison, Wis.) software package version 10.2 and Infomax's Vector NT1 Advance suite version 8.0 can be used for sequence creation, mapping, analysis, annotation and illustration.

Expression Vectors

For the expression of antibodies, expression plasmids for transient expression (e.g. in HEK293 cells) based either on a cDNA organization with or without a CMV-intron A promoter or on a genomic organization with a CMV promoter can be applied.

Beside the antibody expression cassette the vector may contain:
  an origin of replication which allows replication of this plasmid in E. coli, and
  a ß-lactamase gene which confers ampicillin resistance in E. coli.

The transcription unit of the antibody gene may be composed of the following elements:
  unique restriction site(s) at the 5' end
  the immediate early enhancer and promoter from the human cytomegalovirus,
  the intron A sequence in the case of cDNA organization,
  a 5'-untranslated region derived from a human antibody gene,
  an immunoglobulin heavy chain signal sequence,
  the respective antibody chain encoding nucleic acid either as cDNA or with genomic exon-intron organization,
  a 3' untranslated region with a polyadenylation signal sequence, and
  unique restriction site(s) at the 3' end.

The fusion genes encoding the antibody chains can be generated by PCR and/or gene synthesis and assembled by known recombinant methods and techniques by connection of the according nucleic acid segments e.g. using unique restriction sites in the respective vectors. The subcloned nucleic acid sequences can be verified by DNA sequencing. For transient transfections larger quantities of the plasmids can be prepared by plasmid preparation from transformed E. coli cultures.

Cell Culture Techniques

Standard cell culture techniques as described in Current Protocols in Cell Biology (2000), Bonifacino, J. S., Dasso, M., Harford, J. B., Lippincott-Schwartz, J. and Yamada, K. M. (eds.), John Wiley & Sons, Inc., can be used.

Transient Transfections in HEK293 System

Antibodies can be produced by transient expression. Therefore a transfection with the respective plasmids using the HEK293 system (Invitrogen) according to the manufacturer's instruction can be done. Briefly, HEK293 cells (Invitrogen) growing in suspension either in a shake flask or in a stirred fermenter in serum-free FreeStyle™ 293 expression medium (Invitrogen) can be transfected with a mix of the respective expression plasmids and 293Fectin™ or fectin (Invitrogen). For 2 L shake flask (Corning) HEK293 cells can be seeded at a density of $1.0*10^6$ cells/mL in 600 mL and incubated at 120 rpm, 8% $CO_2$. On the next day the cells can be transfected at a cell density of approx. $1.5*10^6$ cells/mL with approx. 42 mL of a mixture of A) 20 mL Opti-MEM medium (Invitrogen) comprising 600 µg total plasmid DNA (1 µg/mL) and B) 20 ml Opti-MEM medium supplemented with 1.2 mL 293 fectin or fectin (2 µl/mL). According to the glucose consumption glucose solution can be added during the course of the fermentation. The supernatant containing the secreted antibody is generally harvested after 5-10 days and antibodies can be either directly purified from the supernatant or the supernatant is frozen and stored.

Protein Determination

The protein concentration of purified antibodies and derivatives can be determined by determining the optical density (OD) at 280 nm, using the molar extinction coefficient calculated on the basis of the amino acid sequence according to Pace, et al., Protein Science 4 (1995) 2411-1423.

Antibody Concentration Determination in Supernatants

The concentration of antibodies and derivatives in cell culture supernatants can be estimated by immunoprecipitation with protein A agarose-beads (Roche Diagnostics GmbH, Mannheim, Germany). Therefore, 60 µL protein A Agarose beads can be washed three times in TBS-NP40 (50 mM Tris buffer, pH 7.5, supplemented with 150 mM NaCl and 1% Nonidet-P40). Subsequently, 1-15 mL cell culture supernatant can be applied to the protein A Agarose beads pre-equilibrated in TBS-NP40. After incubation for at 1 hour at room temperature the beads can be washed on an Ultrafree-MC-filter column (Amicon) once with 0.5 mL TBS-NP40, twice with 0.5 mL 2× phosphate buffered saline (2×PBS, Roche Diagnostics GmbH, Mannheim, Germany) and briefly four times with 0.5 mL 100 mM Na-citrate buffer (pH 5.0). Bound antibody can be eluted by addition of 35 µl NuPAGE® LDS sample buffer (Invitrogen). Half of the sample can be combined with NuPAGE® sample reducing agent or left unreduced, respectively, and heated for 10 min at 70° C. Consequently, 5-30 µl can be applied to a 4-12% NuPAGE® Bis-Tris SDS-PAGE gel (Invitrogen) (with MOPS buffer for non-reduced SDS-PAGE and MES buffer with NuPAGE® antioxidant running buffer additive (Invitrogen) for reduced SDS-PAGE) and stained with Coomassie Blue.

The concentration of the antibodies in cell culture supernatants can be quantitatively measured by affinity HPLC chromatography. Briefly, cell culture supernatants containing antibodies that bind to protein A can be applied to an Applied Biosystems Poros A/20 column in 200 mM $KH_2PO_4$, 100 mM sodium citrate, pH 7.4 and eluted with 200 mM NaCl, 100 mM citric acid, pH 2.5 on an Agilent HPLC 1100 system. The eluted antibody can be quantified by UV absorbance and integration of peak areas. A purified standard IgG1 antibody served as a standard.

Alternatively, the concentration of antibodies and derivatives in cell culture supernatants can be measured by Sandwich-IgG-ELISA. Briefly, StrepaWell High Bind Streptavidin A-96 well microtiter plates (Roche Diagnostics GmbH, Mannheim, Germany) can be coated with 100 µL/well biotinylated anti-human IgG capture molecule F(ab')2-anti-human Fcgamma antibody-BI (Dianova) at 0.1 µg/mL for 1 hour at room temperature or alternatively overnight at 4° C. and subsequently washed three times with 200 µL/well PBS, 0.05% Tween (PBST, Sigma). Thereafter, 100 µL/well of a dilution series in PBS (Sigma) of the respective antibody containing cell culture supernatants can be added to the wells and incubated for 1-2 hour on a shaker at room temperature. The wells can be washed three times with 200 µL/well PBST and bound antibody was detected with 100 µl F(ab')2-anti-human Fcgamma antibody-POD (Dianova) at 0.1 µg/mL as the detection antibody by incubation for 1-2 hours on a shaker at room temperature. Unbound detection antibody can be removed by washing three times with 200 µL/well PBST. The bound detection antibody can be detected by addition of 100 µL ABTS/well followed by incubation. Determination of absorbance was performed on a Tecan Fluor Spectrometer at a measurement wavelength of 405 nm (reference wavelength 492 nm).

Preparative Antibody Purification

Antibodies can be purified from filtered cell culture supernatants referring to standard protocols. In brief, antibodies can be applied to a protein A Sepharose column (GE Healthcare) and washed with PBS. Elution of antibodies can be achieved at pH 2.8 followed by immediate neutralization. Aggregated protein can be separated from monomeric antibodies by size exclusion chromatography (Superdex 200, GE Healthcare) in PBS or in 20 mM Histidine buffer comprising 150 mM NaCl (pH 6.0). Monomeric antibody fractions can be pooled, concentrated (if required) using e.g., a MILLIPORE Amicon Ultra (30 MWCO) centrifugal concentrator, frozen and stored at −20° C. or −80° C. Part of the samples can be provided for subsequent protein analytics and analytical characterization e.g. by SDS-PAGE, size exclusion chromatography (SEC) or mass spectrometry.

SDS-PAGE

The NuPAGE® Pre-Cast gel system (Invitrogen) can be used according to the manufacturer's instruction. In particular, 10% or 4-12% NuPAGE® Novex® Bis-TRIS Pre-Cast gels (pH 6.4) and a NuPAGE® MES (reduced gels, with NuPAGE® antioxidant running buffer additive) or MOPS (non-reduced gels) running buffer can be used.

CE-SDS

Purity and antibody integrity can be analyzed by CE-SDS using microfluidic Labchip technology (PerkinElmer, USA). Therefore, 5 µl of antibody solution can be prepared for CE-SDS analysis using the HT Protein Express Reagent Kit according manufacturer's instructions and analyzed on LabChip GXII system using a HT Protein Express Chip. Data can be analyzed using LabChip GX Software.

Analytical Size Exclusion Chromatography

Size exclusion chromatography (SEC) for the determination of the aggregation and oligomeric state of antibodies can be performed by HPLC chromatography. Briefly, protein A purified antibodies can be applied to a Tosoh TSKgel G3000SW column in 300 mM NaCl, 50 mM $KH_2PO_4$/$K_2HPO_4$ buffer (pH 7.5) on an Dionex Ultimate® system (Thermo Fischer Scientific), or to a Superdex 200 column (GE Healthcare) in 2×PBS on a Dionex HPLC-System. The eluted antibody can be quantified by UV absorbance and integration of peak areas. BioRad Gel Filtration Standard 151-1901 served as a standard.

Mass Spectrometry

The antibodies can be deglycosylated with N-Glycosidase F in a phosphate or Tris buffer at 37° C. for up to 17 h at a protein concentration of 1 mg/ml. The limited LysC (Roche Diagnostics GmbH, Mannheim, Germany) digestions can be performed with 100 µg deglycosylated antibody in a Tris buffer (pH 8) at room temperature for 120 hours, or at 37° C. for 40 min, respectively. Prior to mass spectrometry the samples can be desalted via HPLC on a Sephadex G25 column (GE Healthcare). The total mass was determined via ESI-MS on a maXis 4G UHR-QTOF MS system (Bruker Daltonik) equipped with a TriVersa NanoMate source (Advion).

Production of Immunoglobulin

Hybridoma cell lines are inoculated at initial cell densities (live cells) between $1.0 \times 10^5$ and $2.2 \times 10^5$ cells per ml in RPMI 1640 supplemented with 10% FCS, and commonly used supplements and expanded in a T-flask (Celline, IBS) for a period of approximately three weeks. Purification of the antibodies from the culture supernatants are done according to standard protein chemical methods, e.g. as those reported in Bruck, C., et al., Methods Enzymol. 121 (1986) 587-596.

Bridging ADA Assay

All steps of this one-step ELISA bridging assay were performed at room temperature (RT), and samples and quality controls were analyzed in the presence of 10% HPS (human pooled serum). Samples were diluted 1:10 in low cross Buffer® containing biotinylated capture and digoxigenylated detection antibodies (=therapeutic antibody) (1.0 µg/ml each) and incubated overnight at RT and with shaking at 450 rpm. Samples (100 µl) were then transferred to a SA-coated MTP. After 1 h incubation at RT (450 rpm), wells were washed three-times (300 µl washing buffer each). After addition of 100 µl polyclonal anti-Dig-S-Fab-HRP conjugate (25 mU/ml) and 1 h incubation, the plate was washed again (three-times with 300 µl washing buffer). Finally, 100 µl ABTS substrate per well was added, and color reaction was photometrically assessed at 405 nm (reference wavelength 490 nm). Samples were measured in duplicates and averaged. Measurements were accepted as valid if the precision of duplicates was ≤20% of the coefficient of variation (CV). The screening cut-point was determined according to Shankar et al. (Shankar, G., et al., J. Pharm. Biomed. Anal. 48 (2008) 1267-1281) by analyzing 34 individual blank serum samples, 17 each of males and females, in duplicates. Samples assessed as ADA positive during screening, were confirmed for specificity by re-testing in the presence of unlabeled detection antibody (therapeutic antibody) (333 ng/ml), which was added to diluted samples before overnight incubation.

hsFcγRI-PG Assay

All steps of the procedure were performed at RT. Samples were tested at a final dilution of 1:50, and all samples and quality controls were analyzed in the presence of 2% HPS and 1 µg/mL therapeutic antibody. First, 100 µl/well bi-labelled anti-PG antibody (2 µg/ml) was bound to a SA-coated MTP. After 1 h incubation (450 rpm), wells were washed three times in 300 µl washing buffer (all following incubation and washing steps were performed likewise). Then, quality standards and samples that had been pre-incubated in low cross Buffer® containing 1 µg/ml therapeutic antibody were added at a volume of 100 µl/well. After incubation and washing, dig-labelled hsFcγRI (soluble human FcγRI) (0.5 µg/ml) at 100 µl/well, and, after additional incubation and washing, 100 µl/well polyclonal anti-Dig-S-Fab-HRP conjugate (50 mU/ml) were added. After incubation and washing as described above, 100 µl/well ABTS substrate was added. Absorption was measured at 405 nm wavelength (reference wavelength 490 nm). Samples were analyzed in duplicates and averaged. The cut-point of this assay was evaluated by analysis of 25 individual blank serum samples of either sex in duplicates. Calculation of the cut-point was performed using a non-parametric approach according to Shankar et al. (Shankar, G., et al., J. Pharm. Biomed. Anal. 48 (2008) 1267-1281).

Example 2

The Antibodies as Reported Herein as Capture Antibody

Biotinylated anti-PGLALA Fc-region antibody or biotinylated anti-AAA Fc-region antibody, respectively, was bound to the wells of a streptavidin-coated multi-well plate (SA-MTP) to produce a capture plate. Excess of unbound antibody was removed by washing. Sample/standard antibodies spiked in human and cynomolgus monkey serum (10% final concentration) was added to wells of the SA-MTP multi-well plate coated with the capture plate and incubated for 1 hour at room temperature. After washing, the wells were incubated with digoxigenylated anti-human kappa antibody M1.7.10 (see e.g. WO 2011/048043, incorporated herein by reference). After washing the bound digoxigenylated anti-human kappa antibody complex was incubated with a horseradish peroxidase (HRP) labelled anti-digoxigenin antibody. After another washing step, an ABTS solution was added to the wells and incubated. The product of the color reaction was measured by Elisa reader at 405 nm wavelength (reference wavelength: 490 nm). Absorbance values of each sample or standard were determined in triplicates.

The following Table shows the extinction values determined for an anti-VEGF/ANG2 antibody with the mutations P329G, L234A, L235A, I253A, H310A, and H435A in serum with the anti-variant (human) Fc-region antibody M1.3.17 (SEQ ID NO: 03 and 04) as reported herein as capture antibody.

| anti-VEGF/ANG2 antibody [ng/mL] | signal [OD405 nm] |
|---|---|
| 10 | 2.2255 |
| 5 | 1.6010 |
| 2.5 | 0.9865 |
| 1.25 | 0.5730 |
| 0.625 | 0.3140 |
| 0.3125 | 0.1815 |
| 0.15625 | 0.1075 |
| 0 | 0.0740 |

The following Table shows the extinction values determined for antibodies of different specificity with different mutations in the Fc-region using different antibodies as reported herein as capture and detection antibodies.

assay B: capture antibody: M1.6.22-Bi/M1.7.24-Bi/M1.3.17-Bi
  tracer antibody: 1.7.10-Dig
assay C: capture antibody: M1.6.22-Bi/M1.7.24-Bi/M1.3.17-Bi
  tracer compound: FcγRI-Dig
M1.6.22=anti-AAA variant Fc-region antibody
M1.7.10=anti-IgG1 kappa antibody
M1.7.24=anti-PGLALA variant Fc-region antibody
M1.3.17=anti-PGLALA variant Fc-region antibody
Samples:
  1) anti-VEGF/ANG2 antibody (IgG1 subclass with mutations P329G/L234A/L235A/I253A/H310A/H435A)
  2) anti-VEGF/ANG2 antibody (IgG1 subclass with mutations P329G/L234A/L235A)
  3) anti-IGF-1R antibody (IgG1 subclass with mutations I253 A/H310A/H435A)
  4) anti-P-Selectin antibody (IgG4 subclass with mutations S228P/L235E)
  5) anti-VEGF/ANG2 antibody (wild-type IgG1 subclass)

| assay | capture | tracer | anti-body | concentration [ng/mL] | signal [OD405 nm] |
|---|---|---|---|---|---|
| B | M1.6.22-Bi | M1.7.10-Dig | 1 | 100 | 0.052 |
|   |   |   |   | 50 | 0.050 |
|   |   |   |   | 25 | 0.044 |
|   |   |   |   | 13 | 0.041 |
|   |   |   |   | 6 | 0.039 |
|   |   |   |   | 3 | 0.039 |
|   |   |   |   | 2 | 0.041 |
|   |   |   |   | 0 | 0.047 |
| B | M1.6.22-Bi | M1.7.10-Dig | 2 | 100 | 0.210 |
|   |   |   |   | 50 | 0.127 |
|   |   |   |   | 25 | 0.092 |
|   |   |   |   | 13 | 0.066 |
|   |   |   |   | 6 | 0.053 |
|   |   |   |   | 3 | 0.044 |
|   |   |   |   | 2 | 0.041 |
|   |   |   |   | 0 | 0.038 |
| B | M1.6.22-Bi | M1.7.10-Dig | 3 | 100 | 2.898 |
|   |   |   |   | 50 | 2.900 |
|   |   |   |   | 25 | 2.894 |
|   |   |   |   | 13 | 2.849 |
|   |   |   |   | 6 | 2.734 |
|   |   |   |   | 3 | 2.259 |
|   |   |   |   | 2 | 1.482 |
|   |   |   |   | 0 | 0.037 |
| B | M1.6.22-Bi | M1.7.10-Dig | 4 | 100 | 0.051 |
|   |   |   |   | 50 | 0.047 |
|   |   |   |   | 25 | 0.048 |
|   |   |   |   | 13 | 0.042 |
|   |   |   |   | 6 | 0.040 |
|   |   |   |   | 3 | 0.039 |
|   |   |   |   | 2 | 0.032 |
|   |   |   |   | 0 | 0.038 |
| B | M1.6.22-Bi | M1.7.10-Dig | 5 | 100 | 0.061 |
|   |   |   |   | 50 | 0.049 |
|   |   |   |   | 25 | 0.047 |
|   |   |   |   | 13 | 0.046 |
|   |   |   |   | 6 | 0.039 |
|   |   |   |   | 3 | 0.037 |
|   |   |   |   | 2 | 0.036 |
|   |   |   |   | 0 | 0.037 |
| B | M1.7.24-Bi | M1.7.10-Dig | 1 | 100 | 0.057 |
|   |   |   |   | 50 | 0.060 |
|   |   |   |   | 25 | 0.047 |
|   |   |   |   | 13 | 0.053 |
|   |   |   |   | 6 | 0.053 |
|   |   |   |   | 3 | 0.040 |
|   |   |   |   | 2 | 0.049 |
|   |   |   |   | 0 | 0.049 |
| B | M1.7.24-Bi | M1.7.10-Dig | 2 | 100 | 3.235 |
|   |   |   |   | 50 | 3.167 |
|   |   |   |   | 25 | 3.159 |
|   |   |   |   | 13 | 3.148 |
|   |   |   |   | 6 | 2.981 |
|   |   |   |   | 3 | 2.513 |
|   |   |   |   | 2 | 1.730 |
|   |   |   |   | 0 | 0.046 |
| B | M1.7.24-Bi | M1.7.10-Dig | 3 | 100 | 0.098 |
|   |   |   |   | 50 | 0.064 |
|   |   |   |   | 25 | 0.048 |
|   |   |   |   | 13 | 0.043 |
|   |   |   |   | 6 | 0.039 |
|   |   |   |   | 3 | 0.046 |
|   |   |   |   | 2 | 0.047 |
|   |   |   |   | 0 | 0.040 |
| B | M1.7.24-Bi | M1.7.10-Dig | 4 | 100 | 0.050 |
|   |   |   |   | 50 | 0.043 |
|   |   |   |   | 25 | 0.040 |
|   |   |   |   | 13 | 0.037 |
|   |   |   |   | 6 | 0.037 |
|   |   |   |   | 3 | 0.031 |
|   |   |   |   | 2 | 0.033 |
|   |   |   |   | 0 | 0.035 |
| B | M1.7.24-Bi | M1.7.10-Dig | 5 | 100 | 0.047 |
|   |   |   |   | 50 | 0.040 |
|   |   |   |   | 25 | 0.041 |
|   |   |   |   | 13 | 0.040 |
|   |   |   |   | 6 | 0.038 |
|   |   |   |   | 3 | 0.033 |
|   |   |   |   | 2 | 0.034 |
|   |   |   |   | 0 | 0.039 |
| B | M1.3.17-Bi | M1.7.10-Dig | 1 | 100 | 0.035 |
|   |   |   |   | 50 | 0.035 |
|   |   |   |   | 25 | 0.035 |
|   |   |   |   | 13 | 0.034 |
|   |   |   |   | 6 | 0.035 |
|   |   |   |   | 3 | 0.036 |
|   |   |   |   | 2 | 0.036 |
|   |   |   |   | 0 | 0.035 |
| B | M1.3.17-Bi | M1.7.10-Dig | 2 | 100 | 0.216 |
|   |   |   |   | 50 | 0.215 |
|   |   |   |   | 25 | 0.213 |
|   |   |   |   | 13 | 0.217 |
|   |   |   |   | 6 | 0.196 |
|   |   |   |   | 3 | 0.165 |
|   |   |   |   | 2 | 0.125 |
|   |   |   |   | 0 | 0.038 |
| B | M1.3.17-Bi | M1.7.10-Dig | 3 | 100 | 0.050 |
|   |   |   |   | 50 | 0.048 |
|   |   |   |   | 25 | 0.046 |
|   |   |   |   | 13 | 0.044 |
|   |   |   |   | 6 | 0.045 |
|   |   |   |   | 3 | 0.047 |
|   |   |   |   | 2 | 0.047 |
|   |   |   |   | 0 | 0.045 |
| B | M1.3.17-Bi | M1.7.10-Dig | 4 | 100 | 0.048 |
|   |   |   |   | 50 | 0.049 |
|   |   |   |   | 25 | 0.047 |
|   |   |   |   | 13 | 0.047 |
|   |   |   |   | 6 | 0.048 |
|   |   |   |   | 3 | 0.050 |
|   |   |   |   | 2 | 0.049 |
|   |   |   |   | 0 | 0.049 |
| B | M1.3.17-Bi | M1.7.10-Dig | 5 | 100 | 0.043 |
|   |   |   |   | 50 | 0.042 |
|   |   |   |   | 25 | 0.043 |
|   |   |   |   | 13 | 0.042 |
|   |   |   |   | 6 | 0.046 |
|   |   |   |   | 3 | 0.044 |
|   |   |   |   | 2 | 0.043 |
|   |   |   |   | 0 | 0.043 |
| C | M1.6.22-Bi | FcγRI-Dig | 1 | 100 | 0.079 |
|   |   |   |   | 50 | 0.077 |
|   |   |   |   | 25 | 0.081 |
|   |   |   |   | 13 | 0.064 |
|   |   |   |   | 6 | 0.060 |
|   |   |   |   | 3 | 0.066 |
|   |   |   |   | 2 | 0.077 |
|   |   |   |   | 0 | 0.077 |
| C | M1.6.22-Bi | FcγRI-Dig | 2 | 100 | 0.076 |
|   |   |   |   | 50 | 0.057 |
|   |   |   |   | 25 | 0.063 |
|   |   |   |   | 13 | 0.061 |
|   |   |   |   | 6 | 0.060 |
|   |   |   |   | 3 | 0.068 |
|   |   |   |   | 2 | 0.072 |
|   |   |   |   | 0 | 0.064 |
| C | M1.6.22-Bi | FcγRI-Dig | 3 | 100 | 2.096 |
|   |   |   |   | 50 | 1.059 |
|   |   |   |   | 25 | 0.401 |
|   |   |   |   | 13 | 0.175 |
|   |   |   |   | 6 | 0.104 |
|   |   |   |   | 3 | 0.083 |
|   |   |   |   | 2 | 0.082 |
|   |   |   |   | 0 | 0.069 |
| C | M1.6.22-Bi | FcγRI-Dig | 4 | 100 | 0.069 |
|   |   |   |   | 50 | 0.054 |
|   |   |   |   | 25 | 0.060 |
|   |   |   |   | 13 | 0.052 |
|   |   |   |   | 6 | 0.051 |
|   |   |   |   | 3 | 0.050 |
|   |   |   |   | 2 | 0.067 |
|   |   |   |   | 0 | 0.077 |
| C | M1.6.22-Bi | FcγRI-Dig | 5 | 100 | 0.076 |
|   |   |   |   | 50 | 0.067 |

| assay | capture | tracer | antibody | concentration [ng/mL] | signal [OD405 nm] |
|---|---|---|---|---|---|
| | | | | 25 | 0.066 |
| | | | | 13 | 0.070 |
| | | | | 6 | 0.064 |
| | | | | 3 | 0.069 |
| | | | | 2 | 0.077 |
| | | | | 0 | 0.069 |
| C | M1.7.24-Bi | FcγRI-Dig | 1 | 100 | 0.050 |
| | | | | 50 | 0.084 |
| | | | | 25 | 0.082 |
| | | | | 13 | 0.085 |
| | | | | 6 | 0.079 |
| | | | | 3 | 0.094 |
| | | | | 2 | 0.085 |
| | | | | 0 | 0.076 |
| C | M1.7.24-Bi | FcγRI-Dig | 2 | 100 | 0.082 |
| | | | | 50 | 0.094 |
| | | | | 25 | 0.083 |
| | | | | 13 | 0.060 |
| | | | | 6 | 0.060 |
| | | | | 3 | 0.057 |
| | | | | 2 | 0.093 |
| | | | | 0 | 0.092 |
| C | M1.7.24-Bi | FcγRI-Dig | 3 | 100 | 0.110 |
| | | | | 50 | 0.095 |
| | | | | 25 | 0.073 |
| | | | | 13 | 0.058 |
| | | | | 6 | 0.069 |
| | | | | 3 | 0.077 |
| | | | | 2 | 0.074 |
| | | | | 0 | 0.086 |
| C | M1.7.24-Bi | FcγRI-Dig | 4 | 100 | 0.080 |
| | | | | 50 | 0.066 |
| | | | | 25 | 0.070 |
| | | | | 13 | 0.066 |
| | | | | 6 | 0.053 |
| | | | | 3 | 0.053 |
| | | | | 2 | 0.056 |
| | | | | 0 | 0.076 |
| C | M1.7.24-Bi | FcγRI-Dig | 5 | 100 | 0.073 |
| | | | | 50 | 0.066 |
| | | | | 25 | 0.063 |
| | | | | 13 | 0.057 |
| | | | | 6 | 0.057 |
| | | | | 3 | 0.053 |
| | | | | 2 | 0.058 |
| | | | | 0 | 0.073 |
| C | M1.3.17-Bi | FcγRI-Dig | 1 | 100 | 1.194 |
| | | | | 50 | 1.167 |
| | | | | 25 | 1.074 |
| | | | | 13 | 1.137 |
| | | | | 6 | 1.171 |
| | | | | 3 | 1.161 |
| | | | | 2 | 1.171 |
| | | | | 0 | 1.176 |
| C | M1.3.17-Bi | FcγRI-Dig | 2 | 100 | 1.222 |
| | | | | 50 | 1.211 |
| | | | | 25 | 1.214 |
| | | | | 13 | 1.226 |
| | | | | 6 | 1.215 |
| | | | | 3 | 1.222 |
| | | | | 2 | 1.221 |
| | | | | 0 | 1.233 |
| C | M1.3.17-Bi | FcγRI-Dig | 3 | 100 | 1.204 |
| | | | | 50 | 1.214 |
| | | | | 25 | 1.203 |
| | | | | 13 | 1.213 |
| | | | | 6 | 1.212 |
| | | | | 3 | 1.210 |
| | | | | 2 | 1.260 |
| | | | | 0 | 1.217 |
| C | M1.3.17-Bi | FcγRI-Dig | 4 | 100 | 1.170 |
| | | | | 50 | 1.153 |
| | | | | 25 | 1.166 |
| | | | | 13 | 1.161 |
| | | | | 6 | 1.175 |
| | | | | 3 | 1.188 |
| | | | | 2 | 1.191 |
| | | | | 0 | 1.189 |
| C | M1.3.17-Bi | FcγRI-Dig | 5 | 100 | 1.183 |
| | | | | 50 | 1.161 |
| | | | | 25 | 1.163 |
| | | | | 13 | 1.166 |
| | | | | 6 | 1.173 |
| | | | | 3 | 1.187 |
| | | | | 2 | 1.190 |
| | | | | 0 | 1.197 | assay D: capture antibody: M1.7.24-Bi/M1.3.17-Bi
tracer antibody: 1.7.10-Dig/M1.19.31-Dig
M1.7.10=anti-IgG1 kappa antibody
M1.19.31=anti-IgG1 kappa antibody
M1.7.24=anti-PGLALA variant Fc-region antibody
M1.3.17=anti-PGLALA variant Fc-region antibody
Samples:
  6) anti-Dig antibody (IgG1 subclass with mutations P329G/L234A/L235A)

| assay | capture | tracer | signal buffer [OD405 nm] | signal 10% cynomolgus serum [OD405 nm] | signal 10% human serum [OD405 nm] |
|---|---|---|---|---|---|
| D | M1.3.17-Bi | M1.7.10-Dig | 0.053 | 2.116 | 2.656 |
| | | | 0.038 | 1.177 | 2.550 |
| | | | 0.037 | 0.485 | 2.508 |
| | | | 0.032 | 0.194 | 2.482 |
| | | | 0.031 | 0.096 | 2.489 |
| | | | 0.032 | 0.065 | 2.529 |
| | | | 0.029 | 0.052 | 2.533 |
| | | | 0.031 | 0.044 | 2.514 |
| D | M1.3.17-Bi | M1.19.31-Dig | 0.050 | 1.874 | 2.583 |
| | | | 0.041 | 0.872 | 2.137 |
| | | | 0.040 | 0.357 | 1.843 |
| | | | 0.037 | 0.162 | 1.728 |
| | | | 0.036 | 0.105 | 1.706 |
| | | | 0.033 | 0.082 | 1.671 |
| | | | 0.033 | 0.075 | 1.706 |
| | | | 0.036 | 0.077 | 1.802 |
| D | M1.7.24-Bi | M1.7.10-Dig | 0.062 | 2.367 | 2.738 |
| | | | 0.046 | 1.413 | 2.609 |
| | | | 0.039 | 0.575 | 2.484 |
| | | | 0.034 | 0.223 | 2.457 |
| | | | 0.031 | 0.094 | 2.407 |
| | | | 0.031 | 0.050 | 2.396 |
| | | | 0.034 | 0.041 | 2.438 |
| | | | 0.033 | 0.031 | 2.452 |
| D | M1.7.24-Bi | M1.19.31-Dig | 0.054 | 2.254 | 2.505 |
| | | | 0.051 | 1.168 | 2.044 |
| | | | 0.045 | 0.438 | 1.605 |
| | | | 0.037 | 0.173 | 1.427 |
| | | | 0.033 | 0.078 | 1.335 |
| | | | 0.033 | 0.049 | 1.362 |
| | | | 0.033 | 0.039 | 1.386 |
| | | | 0.033 | 0.035 | 1.423 |

Example 3

The Antibodies as Reported Herein as Tracer Antibody
Biotinylated anti-human kappa antibody M1.7.10 (see e.g. WO 2011/048043) was bound to the wells of a streptavidin-coated multi-well plate (SA-MTP) to produce a capture plate. Excess of unbound antibody was removed by washing.

Sample/standard antibodies spiked in human and cynomolgus monkey serum (10% final concentration) was added to wells of the SA-MTP multi-well plate coated with the capture plate and incubated for 1 hour at room temperature. After washing, the wells were incubated with digoxigenylated anti-PGLALA Fc-region antibody or anti-AAA Fc-region antibody, respectively. After washing the bound digoxigenylated anti-human kappa antibody complex was incubated with a horseradish peroxidase (HRP) labelled anti-digoxigenin antibody. After another washing step, an ABTS solution was added to the wells. The product of the color reaction was measured by Elisa reader at 405 nm wavelength (reference wavelength: 490 nm). Absorbance values of each sample or standard were determined in triplicates.

The following Table shows the extinction values determined for an anti-VEGF/ANG2 antibody with the mutations P329G, L234A, L235A, I253A, H310A, and H435A in serum with the anti-variant (human) Fc-region antibody M1.7.24 (SEQ ID NO: 07 and 08) as reported herein as tracer antibody.

| anti-VEGF/ANG2 antibody [ng/mL] | signal [OD405 nm] |
|---|---|
| 10 | 2.7565 |
| 5 | 2.1725 |
| 2.5 | 1.437 |
| 1.25 | 0.8465 |
| 0.625 | 0.468 |
| 0.3125 | 0.261 |
| 0.15625 | 0.1475 |
| 0.078125 | 0.096 |
| 0.0390625 | 0.072 |
| 0.01953125 | 0.057 |

The following Table shows the extinction values determined for antibodies of different specificity with different mutations in the Fc-region using different antibodies as reported herein as capture and detection antibodies.
assay A: capture antibody: M1.7.10-Bi
    tracer antibody: M1.6.22-Dig/M1.7.24-Dig/M1.3.17-Dig
M1.6.22=anti-AAA variant Fc-region antibody
M1.7.10=anti-IgG1 kappa antibody
M1.7.24=anti-PGLALA variant Fc-region antibody
M1.3.17=anti-PGLALA variant Fc-region antibody
Samples:
  1) anti-VEGF/ANG2 antibody (IgG1 subclass with mutations P329G/L234A/L235A/I253A/H310A/H435A)
  2) anti-VEGF/ANG2 antibody (IgG1 subclass with mutations P329G/L234A/L235A)
  3) anti-IGF-1R antibody (IgG1 subclass with mutations I253A/H310A/H435A)
  4) anti-P-Selectin antibody (IgG4 subclass with mutations S228P/L235E)
  5) anti-VEGF/ANG2 antibody (wild-type IgG1 subclass)

| assay | capture | tracer | antibody | concentration [ng/mL] | signal [OD405 nm] |
|---|---|---|---|---|---|
| A | M1.7.10-Bi | M1.6.22-Dig | 1 | 100 | 0.059 |
| | | | | 50 | 0.060 |
| | | | | 25 | 0.061 |
| | | | | 13 | 0.061 |
| | | | | 6 | 0.057 |
| | | | | 3 | 0.057 |
| | | | | 2 | 0.055 |
| | | | | 0 | 0.058 |
| A | M1.7.10-Bi | M1.6.22-Dig | 2 | 100 | 0.076 |
| | | | | 50 | 0.065 |
| | | | | 25 | 0.060 |
| | | | | 13 | 0.051 |
| | | | | 6 | 0.044 |
| | | | | 3 | 0.039 |
| | | | | 2 | 0.047 |
| | | | | 0 | 0.048 |
| A | M1.7.10-Bi | M1.6.22-Dig | 3 | 100 | 2.889 |
| | | | | 50 | 2.740 |
| | | | | 25 | 2.509 |
| | | | | 13 | 1.738 |
| | | | | 6 | 0.858 |
| | | | | 3 | 0.414 |
| | | | | 2 | 0.199 |
| | | | | 0 | 0.046 |
| A | M1.7.10-Bi | M1.6.22-Dig | 4 | 100 | 0.057 |
| | | | | 50 | 0.052 |
| | | | | 25 | 0.057 |
| | | | | 13 | 0.050 |
| | | | | 6 | 0.041 |
| | | | | 3 | 0.037 |
| | | | | 2 | 0.040 |
| | | | | 0 | 0.043 |
| A | M1.7.10-Bi | M1.6.22-Dig | 5 | 100 | 0.056 |
| | | | | 50 | 0.045 |
| | | | | 25 | 0.053 |
| | | | | 13 | 0.045 |
| | | | | 6 | 0.046 |
| | | | | 3 | 0.039 |
| | | | | 2 | 0.047 |
| | | | | 0 | 0.042 |
| A | M1.7.10-Bi | M1.7.24-Dig | 1 | 100 | 0.053 |
| | | | | 50 | 0.051 |
| | | | | 25 | 0.047 |
| | | | | 13 | 0.047 |
| | | | | 6 | 0.045 |
| | | | | 3 | 0.046 |
| | | | | 2 | 0.042 |
| | | | | 0 | 0.050 |
| A | M1.7.10-Bi | M1.7.24-Dig | 2 | 100 | 2.652 |
| | | | | 50 | 2.604 |
| | | | | 25 | 2.606 |
| | | | | 13 | 2.516 |
| | | | | 6 | 2.239 |
| | | | | 3 | 1.730 |
| | | | | 2 | 1.134 |
| | | | | 0 | 0.043 |
| A | M1.7.10-Bi | M1.7.24-Dig | 3 | 100 | 0.060 |
| | | | | 50 | 0.048 |
| | | | | 25 | 0.047 |
| | | | | 13 | 0.044 |
| | | | | 6 | 0.042 |
| | | | | 3 | 0.045 |
| | | | | 2 | 0.048 |
| | | | | 0 | 0.049 |
| A | M1.7.10-Bi | M1.7.24-Dig | 4 | 100 | 0.046 |
| | | | | 50 | 0.049 |
| | | | | 25 | 0.048 |
| | | | | 13 | 0.046 |
| | | | | 6 | 0.045 |
| | | | | 3 | 0.040 |
| | | | | 2 | 0.036 |
| | | | | 0 | 0.045 |
| A | M1.7.10-Bi | M1.7.24-Dig | 5 | 100 | 0.042 |
| | | | | 50 | 0.048 |
| | | | | 25 | 0.039 |
| | | | | 13 | 0.042 |
| | | | | 6 | 0.042 |
| | | | | 3 | 0.038 |
| | | | | 2 | 0.038 |
| | | | | 0 | 0.041 |
| A | M1.7.10-Bi | M1.3.17-Dig | 1 | 100 | 0.043 |
| | | | | 50 | 0.043 |
| | | | | 25 | 0.040 |
| | | | | 13 | 0.040 |

-continued

| assay | capture | tracer | antibody | concentration [ng/mL] | signal [OD405 nm] |
|---|---|---|---|---|---|
| | | | | 6 | 0.042 |
| | | | | 3 | 0.038 |
| | | | | 2 | 0.043 |
| | | | | 0 | 0.044 |
| A | M1.7.10-Bi | M1.3.17-Dig | 2 | 100 | 3.044 |
| | | | | 50 | 2.955 |
| | | | | 25 | 2.932 |
| | | | | 13 | 2.698 |
| | | | | 6 | 1.985 |
| | | | | 3 | 1.215 |
| | | | | 2 | 0.669 |
| | | | | 0 | 0.042 |
| A | M1.7.10-Bi | M1.3.17-Dig | 3 | 100 | 0.047 |
| | | | | 50 | 0.044 |
| | | | | 25 | 0.043 |
| | | | | 13 | 0.040 |
| | | | | 6 | 0.038 |
| | | | | 3 | 0.036 |
| | | | | 2 | 0.042 |
| | | | | 0 | 0.040 |
| A | M1.7.10-Bi | M1.3.17-Dig | 4 | 100 | 0.040 |
| | | | | 50 | 0.037 |
| | | | | 25 | 0.037 |
| | | | | 13 | 0.038 |
| | | | | 6 | 0.036 |
| | | | | 3 | 0.033 |
| | | | | 2 | 0.034 |
| | | | | 0 | 0.036 |
| A | M1.7.10-Bi | M1.3.17-Dig | 5 | 100 | 0.042 |
| | | | | 50 | 0.041 |
| | | | | 25 | 0.037 |
| | | | | 13 | 0.038 |
| | | | | 6 | 0.036 |
| | | | | 3 | 0.033 |
| | | | | 2 | 0.034 |
| | | | | 0 | 0.036 |

The following Table shows the extinction values determined for an cytokine (IL-2) antibody conjugate with the mutations P329G, L234A, L235A, I253A, H310A, and H435A in serum with an anti-IL2 antibody as capture antibody and the anti-variant (human) Fc-region antibody M1.7.24 (SEQ ID NO: 07 and 08) as reported herein as tracer antibody.

| cytokine antibody conjugate [ng/mL] | signal [OD405 nm] |
|---|---|
| 2500 | 2.346 |
| 1250 | 1.459 |
| 625 | 0.811 |
| 312.5 | 0.4505 |
| 156.25 | 0.253 |
| 78.125 | 0.1525 |
| 39.0625 | 0.1005 |
| 0 | 0.0475 |

Example 4

The Antibodies as Reported Herein as Capture Antibody as Well as as Tracer Antibody Biotinylated anti-PGLALA Fc-region antibody or anti-AAA Fc-region antibody, respectively, was bound to the wells of a streptavidin-coated multi-well plate (SA-MTP) to produce a capture plate. Excess of unbound antibody was removed by washing. Sample/standard antibodies spiked in human and cynomolgus monkey serum (10% final concentration) was added to wells of the SA-MTP multi-well plate coated with the capture plate and incubated for 1 hour at room temperature. After washing, the wells were incubated with digoxigenylated anti-PG Fc-region antibody or anti-AAA Fc-region antibody, respectively. After washing the bound digoxigenylated anti-human kappa antibody complex was incubated with a horseradish peroxidase (HRP) labelled anti-digoxigenin antibody. After another washing step, an ABTS solution was added to the wells. The product of the color reaction was measured by Elisa reader at 405 nm wavelength (reference wavelength: 490 nm). Absorbance values of each sample or standard were determined in triplicates.

The following Table shows the extinction values determined for an anti-VEGF/ANG2 antibody with the mutations P329G, L234A, L235A, I253A, H310A, and H435A in serum with the anti-variant (human) Fc-region antibody M1.3.17 (SEQ ID NO: 03 and 04) as reported herein as capture antibody and the anti-variant (human) Fc-region antibody M1.7.24 (SEQ ID NO: 07 and 08) as reported herein as tracer antibody.

| anti-VEGF/ANG2 antibody [ng/mL] | signal [OD405 nm] |
|---|---|
| 2500 | 2.7700 |
| 1250 | 1.8810 |
| 625 | 1.1345 |
| 312.5 | 0.6580 |
| 156.25 | 0.4185 |
| 78.125 | 0.3015 |
| 39.0625 | 0.2325 |
| 0 | 0.1755 |

Example 5

The Antibodies as Reported Herein as Calibration Standard in an Anti-Drug Antibody Assay A dilution series of the anti-PG Fc-region antibody or anti-AAA Fc-region antibody, respectively, was prepared as standard curve.

Biotinylated anti-VEGF/ANG2 antibody with the mutations P329G, L234A, L235A, I253A, H310A, and H435A and digoxigenylated anti-VEGF/ANG2 antibody with the mutations P329G, L234A, L235A, I253A, H310A, and H435A were pre-incubated with the diluted sample or standards overnight at room temperature. After pre-incubation, the samples were transferred to a streptavidin-coated multi-well plate and incubated for 1 hour at room temperature. Excess of unbound antibody was removed by washing. After a washing step the bound digoxigenylated complexes comprising biotinylated and digoxigenylated anti-VEGF/ANG2 antibody with the mutations P329G, L234A, L235A, I253A, H310A, and H435A as well as the anti-PG Fc-region antibody M1.3.17 (SEQ ID NO: 03 and 04) or anti-drug antibody, respectively, were detected with an horseradish peroxidase (HRP) labelled anti-digoxigenin-antibody. After a washing step and upon incubation with the respective substrate the HRP present in the formed complex catalyzes the conversion of ABTS into a colored product. The signal was measured by Elisa reader at 405 nm wavelength (reference wavelength: 490 nm). Absorbance values of each serum sample were determined in triplicates.

The following Table shows the extinction values determined for an anti-VEGF/ANG2 antibody with the mutations P329G, L234A, L235A, I253A, H310A, and H435A in serum as capture antibody (biotinylated) as well as as tracer antibody (digoxigenylated) with the anti-variant (human)

Fc-region antibody M1.3.17 (SEQ ID NO: 03 and 04) as reported herein as standard antibody.

| anti-PGLALA antibody M1.3.17 [ng/mL] | signal [OD405 nm] |
|---|---|
| 250 | 0.150 |
| 125 | 0.085 |
| 62.5 | 0.063 |
| 31.25 | 0.054 |
| 15.625 | 0.050 |
| 7.8125 | 0.047 |
| 3.90625 | 0.045 |
| 0 | 0.046 |

Example 6

Use of the Antibodies as Reported Herein to Deplete Target Antibodies from Samples

| depletion agent | concentration before depletion [µg/mL] | concentration after depletion [µg/mL] | recovery [%] |
|---|---|---|---|
| anti-PGLALA antibody M1.3.17-Bi | 1000.00 | 0.0169 | 0.002% |
| | 30.00 | 0.0080 | 0.027% |
| | 100.00 | 0.0173 | 0.017% |
| | 3.00 | 0.0023 | 0.078% |
| | 10.00 | 0.0017 | 0.017% |
| | 0.30 | 0.0002 | 0.065% |
| | 1.00 | 0.0007 | 0.067% |

| depletion agent | concentration before depletion [µg/mL] | concentration after depletion [µg/mL] | recovery [%] |
|---|---|---|---|
| anti-AAA antibody M1.6.22-Bi | 1000.00 | 0.0163 | 0.002% |
| | 30.00 | 0.0054 | 0.018% |
| | 100.00 | 0.0143 | 0.014% |
| | 3.00 | 0.0023 | 0.008% |
| | 10.00 | 0.0005 | 0.005% |
| | 0.30 | 0.0001 | 0.039% |
| | 1.00 | 0.0003 | 0.031% |

Example 7

The Antibodies as Reported Herein in the Detection of PGLALAAAA Antibodies

Biotinylated anti-PGLALA Fc-region antibody was bound to the wells of a streptavidin-coated multi-well plate (SA-MTP) to produce a capture plate. Excess of unbound antibody was removed by washing. Sample/standard antibodies spiked in human and cynomolgus monkey serum (10% final concentration) was added to wells of the SA-MTP multi-well plate coated with the capture plate and incubated for 1 hour at room temperature. After washing, the wells were incubated with digoxigenylated anti-human kappa antibody M1.7.10 (see e.g. WO 2011/048043, incorporated herein by reference). After washing the bound digoxigenylated anti-human kappa antibody complex was incubated with a horseradish peroxidase (HRP) labelled anti-digoxigenin antibody. After another washing step, an ABTS solution was added to the wells and incubated. The product of the color reaction was measured by Elisa reader at 405 nm wavelength (reference wavelength: 490 nm). Absorbance values of each sample or standard were determined in triplicates.

assay E: capture antibody: M1.7.24-Bi/M1.3.17-Bi
tracer antibody: 1.7.10-Dig
M1.7.10=anti-IgG1 kappa antibody
M1.7.24=anti-PGLALA variant Fc-region antibody
M1.3.17=anti-PGLALA variant Fc-region antibody
Samples:
  1) anti-VEGF/ANG2 antibody (IgG1 subclass with mutations P329G/L234A/L235A/I253A/H310A/H435A)
  2) anti-VEGF/ANG2 antibody (IgG1 subclass with mutations P329G/L234A/L235A)

| assay | capture | tracer | analyte | concentration [ng/mL] | signal [OD405 nm] |
|---|---|---|---|---|---|
| E | M1.7.24-Bi | M1.7.10-Dig | 1) | 100 | 2.312 |
| | | | | 50 | 1.942 |
| | | | | 25 | 1.553 |
| | | | | 12.5 | 1.057 |
| | | | | 6.25 | 0.640 |
| | | | | 3.124 | 0.363 |
| | | | | 1.5625 | 0.208 |
| | | | | 0 | 0.025 |
| E | M1.7.24-Bi | M1.7.10-Dig | 2) | 100 | 2.217 |
| | | | | 50 | 1.796 |
| | | | | 25 | 1.390 |
| | | | | 12.5 | 0.884 |
| | | | | 6.25 | 0.528 |
| | | | | 3.124 | 0.298 |
| | | | | 1.5625 | 0.172 |
| | | | | 0 | 0.028 |
| E | M1.3.17-Bi | M1.7.10-Dig | 1) | 100 | 2.287 |
| | | | | 50 | 1.951 |
| | | | | 25 | 1.602 |
| | | | | 12.5 | 1.093 |
| | | | | 6.25 | 0.677 |
| | | | | 3.124 | 0.383 |
| | | | | 1.5625 | 0.224 |
| | | | | 0 | 0.027 |
| E | M1.3.17-Bi | M1.7.10-Dig | 2) | 100 | 2.269 |
| | | | | 50 | 1.890 |
| | | | | 25 | 1.476 |
| | | | | 12.5 | 0.960 |
| | | | | 6.25 | 0.577 |
| | | | | 3.124 | 0.316 |
| | | | | 1.5625 | 0.187 |
| | | | | 0 | 0.027 |

Example 8

Measurement of Cynomolgus Study Samples—Comparison of the Anti-Drug Assay According to the Invention and Conventional Bridging Anti-Drug Antibody Assay
Bridging Format Anti-Drug Antibody Assay In a first step biotinylated effector function silent therapeutic antibody, sample from a human study using the effector function silent therapeutic antibody, as well as digoxigenylated effector function silent therapeutic antibody were pre-incubated overnight at room temperature (RT) on a microtiter plate (MTP) shaker (500 rpm, 1 µg/ml final capture and tracer concentration; 0-100 ng/ml sample concentration). In a second step pre-incubated samples were transferred to a streptavidin coated MTP (SA-MTP). The excess of unbound complex was removed by washing three times with 300 µL buffer each. After washing the complex-bound digoxigenylated effector function silent therapeutic antibody was detected with a horseradish peroxidase conjugated anti-digoxigenin antibody (incubation for 1 hour at room temperature, 500 rpm shaking). After a further washing step (three times 300 µL buffer) ABTS substrate was added. The signal was measured by ELISA reader at 405 nm wavelength (reference wavelength: 490 nm). Absorbance values of each serum sample were determined in triplicates.

| Sample dilution | 1 to 10 |
|---|---|
| Cut Point | Approx. 0.06 |
| Drug Tolerance | Low |
| IgM Detection | Yes |

Immune Complex Assay Format

Biotinylated anti-PGLALA antibody was bound to streptavidin-coated microtiter plates (SA-MTP) in the first step. Excess of unbound antibody was removed by washing. Samples comprising a complex of effector function silent therapeutic antibody and anti-drug antibody from a study in human serum was added to the wells and incubated for one hour. After washing, the wells were incubated with digoxigenylated human FcγRI. After washing the bound digoxigenylated human FcγRI was detected with a horseradish peroxidase (HRP) conjugated anti-digoxigenin antibody. After a further washing step, ABTS substrate was added. The signal was measured by ELISA reader at 405 nm wavelength (reference wavelength: 490 nm). Absorbance values of each serum sample were determined in duplicates.

| Sample dilution | 1 to 50 |
|---|---|
| Cut Point | Approx. 0.18 |
| Drug Tolerance | high |
| IgM Detection | No |

Study Sample Analysis Results:

| subject | time point cycle/hours | drug level [ng/ml] | bridging assay | immune complex assay |
|---|---|---|---|---|
| 1 | C1 24 h | 1620 | − | − |
|   | C1 72 h | 42.6 | − | − |
|   | C1 96 h | 6.09 | + | − |
|   | C1 120 h | 2.5 | + | − |
|   | C1 168 h | 2.11 | + | − |
|   | C2 24 h | 1310 | + | − |
|   | C2 168 h | b.l.q. | + | + |
|   | C3 pre | b.l.q. | + | + |
| 2 | C1 24 h | 2350 | − | − |
|   | C1 72 h | 94.4 | − | − |
|   | C1 96 h | 11.1 | + | − |
|   | C1 120 h | b.l.q. | + | + |
|   | C1 168 h | b.l.q. | + | + |
|   | C2 24 h | 1010 | + | + |
|   | C2 168 h | b.l.q. | + | + |
|   | C3 pre | b.l.q. | + | + |
| 3 | C1 24 h | 1130 | − | − |
|   | C1 72 h | 11.6 | − | − |
|   | C1 96 h | 5.46 | − | − |
|   | C1 120 h | 1.79 | + | − |
|   | C1 168 h | b.l.q. | + | + |
|   | C2 24 h | 1870 | − | − |
|   | C2 168 h | b.l.q. | − | + |
|   | C3 pre | 455 | + | + |
| 4 | C1 24 h | 6250 | − | − |
|   | C1 96 h | 218 | − | − |
|   | C1 120 h | 26.5 | + | − |
|   | C1 168 h | 2.01 | + | + |
|   | C2 24 h | 2430 | − | + |
|   | C2 168 h | b.l.q. | + | + |
|   | C3 pre | b.l.q. | + | + |
| 5 | C1 24 h | 1800 | − | − |
|   | C1 72 h | 69.6 | − | − |
|   | C1 96 h | 5.83 | − | − |
|   | C2 pre | b.l.q. | + | + |
|   | C2 24 h | 547 | + | + |
|   | C2 96 h | b.l.q. | + | + |
|   | C3 pre | b.l.q. | + | + |
|   | C3 24 h | 13.6 | + | + |
|   | C3 96 h | b.l.q. | + | + |
| 6 | C1 24 h | 2820 | − | − |
|   | C1 72 h | 262 | − | − |
|   | C1 96 h | 2.62 | + | − |
|   | C2 pre | b.l.q. | + | + |
|   | C2 24 h | 263 | − | + |
|   | C2 96 h | b.l.q. | + | + |
|   | C3 pre | b.l.q. | + | + |
| 7 | C1 24 h | 885 | − | − |
|   | C1 72 h | 3.41 | − | − |
|   | C1 96 h | 4.22 | + | − |
|   | C2 pre | 1.25 | + | + |
|   | C2 24 h | 144 | − | + |
|   | C2 96 h | b.l.q. | − | + |
|   | C3 pre | b.l.q. | + | + |
|   | C3 24 h | 176 | − | + |
|   | C3 96 h | 0.764 | − | + |
| 8 | C1 24 h | 212 | − | − |
|   | C1 96 h | 3.5 | − | − |
|   | C1 120 h | 2.57 | − | − |
|   | C1 168 h | 1.99 | − | − |
|   | C2 pre | b.l.q. | − | − |
|   | C2 24 h | 545 | − | − |
|   | C2 168 h | b.l.q. | − | + |
|   | C3 pre | b.l.q. | − | + |
| 9 | C1 24 h | 722 | − | − |
|   | C1 72 h | 61.5 | − | − |
|   | C1 96 h | 6.73 | − | − |
|   | C2 pre | b.l.q. | + | + |
|   | C2 96 h | 9.61 | + | + |
|   | C3 pre | 1.44 | + | − |
|   | C3 96 h | 8.13 | + | − |
| 10 | C1 24 h | 1210 | − | + |
|   | C1 96 h | 5.82 | − | + |
|   | C1 120 h | b.l.q. | + | + |
|   | C1 168 h | b.l.q. | + | + |
|   | C2 pre | 73.8 | + | + |
|   | C2 168 h | b.l.q. | + | + |
|   | C3 pre | b.l.q. | + | + |

Example 9

The Antibodies as Reported Herein as Capture Reagent for Drug-Target Complex Detection to Allow Differentiation of Target Bound and Total Drug 0.5 μg/mL biotinylated anti-PG antibody was bound to the wells of a streptavidin-coated multi-well plate (SA-MTP) to produce a capture plate. Excess of unbound antibody was removed by washing (3 times with 300 μL/well). 100 μL/well sample/standard antibodies were added to wells of the SA-MTP multi-well plate coated with the capture antibody and incubated for 1 hour at room temperature.

Samples include anti target X antibodies (I) with PG(LALA) modification and target X, both free and bound. The anti-target antibody (I) will be bound to that plate.

After washing (3 times with 300 μL/well), the wells were incubated with 100 μL/well of 0.5 μg/mL digoxigenylated anti-target antibody (II).

Anti-target antibodies (I) and (II) are able to bind target X simultaneously.

After washing (3 times with 300 μL/well) the bound digoxigenylated anti-target antibody (II) was incubated with a 100 μL/well of 50 mU/mL horseradish peroxidase (HRP) labelled anti-digoxigenin antibody. After another washing step, 100 μL/well of an ABTS solution was added to the wells. The product of the color reaction was measured by Elisa reader at 405 nm wavelength (reference wavelength:

490 nm). Absorbance values of each sample or standard were determined in triplicates.

Only complexes of drug and target will generate a signal in the assay (bound drug).

It is also possible to pre-incubate the sample with an excess of target to convert all available drug molecules to target bound drug before measurement in the assay to get total drug.

Figure 6:
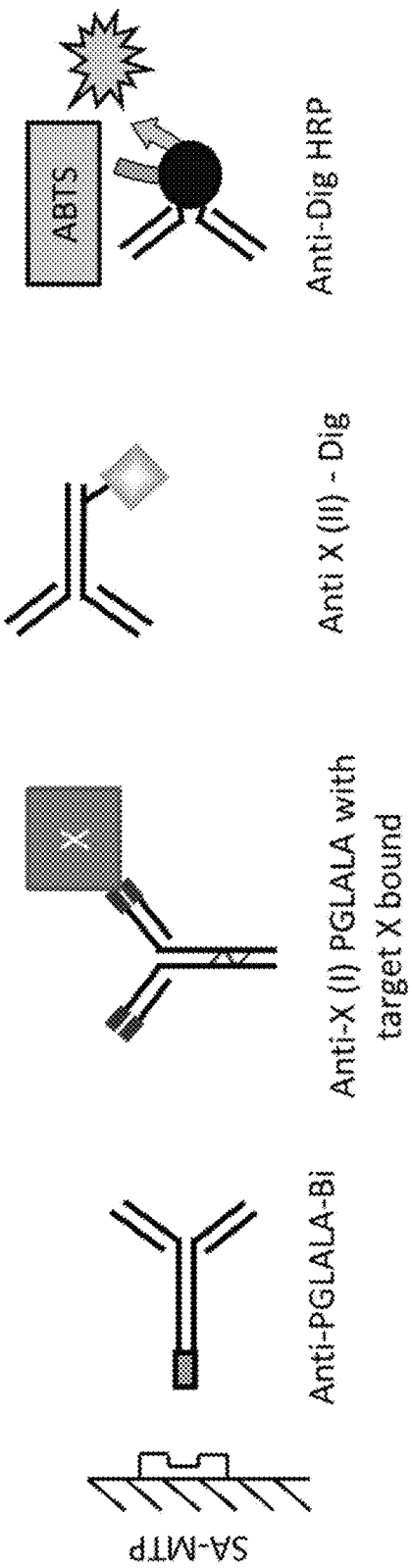
FIG. 6 Scheme of an immunoassay using the antibody as reported herein as capture antibody and an anti-target antibody as tracer antibody.

For a scheme of this assay see FIG. 6.

Although the foregoing invention has been described in some detail by way of illustration and example for purposes of clarity of understanding, the descriptions and examples should not be construed as limiting the scope of the invention. The disclosures of all patent and scientific literature cited herein are expressly incorporated in their entirety by reference.

The invention claimed is:

1. An isolated antibody comprising (a) a HVR-H1 comprising the amino acid sequence of SEQ ID NO: 20; (b) a HVR-H2 comprising the amino acid sequence of SEQ ID NO: 21; (c) a HVR-H3 comprising the amino acid sequence of SEQ ID NO: 22; (d) a HVR-L1 comprising the amino acid sequence of SEQ ID NO: 32; (e) a HVR-L2 comprising the amino acid sequence of SEQ ID NO: 34; and (f) a HVR-L3 comprising the amino acid sequence of SEQ ID NO: 35.

2. The antibody according to claim 1, wherein the antibody is a monoclonal antibody.

3. The antibody according to claim 1, wherein the antibody is a human, humanized, or chimeric antibody.

4. The antibody according to claim 1, wherein the antibody is an antibody fragment.

5. A conjugate comprising the antibody according to claim 1, conjugated to a detectable label.

6. A method of detecting in a biological fluid sample the presence of a therapeutic antibody of a IgGI or IgG4 subclass comprising a variant Fc-region with the mutation P329G or the mutations I253A/H310A/H435A, wherein the amino-acid positions are numbered according to Kabat, the method comprising
(a) contacting the biological fluid sample with the antibody of claim 1, wherein the antibody of claim 1 specifically binds the therapeutic antibody of the IgGI or IgG4 subclass comprising the variant Fc-region with the mutation P329G or the mutations I253A/H310A/H435A, to form a complex; and
(b) detecting the complex, wherein detection of the complex correlates to the presence of the therapeutic antibody of the IgGI or IgG4 subclass comprising the variant Fc-region with the mutation P329G or the mutations I253A/H310A/H435A.

* * * * *